US009018427B2

(12) United States Patent
Gadewar et al.

(10) Patent No.: US 9,018,427 B2
(45) Date of Patent: Apr. 28, 2015

(54) PRODUCTION OF HIGHER ALCOHOLS

(71) Applicant: Greenyug, LLC, Santa Barbara, CA (US)

(72) Inventors: Sagar B. Gadewar, Goleta, CA (US); Brian Christopher Vicente, Santa Barbara, CA (US); Peter K. Stoimenov, Goleta, CA (US); Vivek Julka, Fishkill, NY (US)

(73) Assignee: Greenyug, LLC, Santa Barbara, CA (US)

( * ) Notice: Subject to any disclaimer, the term of this patent is extended or adjusted under 35 U.S.C. 154(b) by 0 days.

(21) Appl. No.: 14/183,273

(22) Filed: Feb. 18, 2014

(65) Prior Publication Data

US 2014/0235901 A1    Aug. 21, 2014

Related U.S. Application Data

(60) Provisional application No. 61/912,235, filed on Dec. 5, 2013, provisional application No. 61/766,484, filed on Feb. 19, 2013.

(51) Int. Cl.
*C07C 29/34* (2006.01)
*B01J 23/00* (2006.01)
*C07C 67/00* (2006.01)

(52) U.S. Cl.
CPC ............... *B01J 23/00* (2013.01); *C07C 29/34* (2013.01); *C07C 67/00* (2013.01)

(58) Field of Classification Search
None
See application file for complete search history.

(56) References Cited

U.S. PATENT DOCUMENTS

| | | | |
|---|---|---|---|
| 1,992,480 A | 2/1935 | Fuchs et al. | |
| 2,525,829 A | 10/1950 | Royer et al. | |
| 3,714,236 A | 1/1973 | Wright, Jr. et al. | |
| 4,052,424 A | 10/1977 | Vanderspurt | |
| 4,220,803 A | 9/1980 | Marcinkowsky et al. | |
| 4,379,028 A | 4/1983 | Berg et al. | |
| 4,435,595 A | 3/1984 | Agreda et al. | |
| 4,440,946 A | 4/1984 | Summerville et al. | |
| 4,523,027 A | 6/1985 | Kummer et al. | |
| 4,569,726 A | 2/1986 | Berg et al. | |
| 4,645,570 A | 2/1987 | Sridhar et al. | |
| 4,825,013 A | 4/1989 | Quarderer et al. | |
| 4,996,007 A | 2/1991 | Chao et al. | |
| 5,194,675 A | 3/1993 | Joerg et al. | |
| 5,334,751 A | 8/1994 | Lemanski et al. | |
| 6,407,295 B1 | 6/2002 | Kaizik et al. | |
| 6,632,330 B1 | 10/2003 | Colley et al. | |
| 6,809,217 B1 | 10/2004 | Colley et al. | |
| 7,700,810 B2 | 4/2010 | Kourtakis et al. | |
| 7,700,811 B2 | 4/2010 | Kourtakis et al. | |
| 7,700,812 B2 | 4/2010 | Kourtakis et al. | |
| 7,700,813 B2 | 4/2010 | Kourtakis et al. | |
| 7,705,192 B2 | 4/2010 | Kourtakis et al. | |
| 7,745,672 B2 | 6/2010 | Kourtakis et al. | |
| 8,071,823 B2 | 12/2011 | Ozer et al. | |
| 8,080,684 B2 | 12/2011 | Hassan et al. | |
| 8,080,695 B2 * | 12/2011 | Tsuchida et al. | 568/902 |
| 8,304,587 B2 | 11/2012 | Warner et al. | |
| 8,318,989 B2 | 11/2012 | Kourtakis et al. | |
| 8,558,025 B2 | 10/2013 | Gadewar | |
| 8,562,921 B2 | 10/2013 | Gadewar | |
| 2013/0197266 A1 | 8/2013 | Gadewar et al. | |
| 2014/0012037 A1 | 1/2014 | Gadewar et al. | |

FOREIGN PATENT DOCUMENTS

| | | |
|---|---|---|
| BR | 9104652 A | 4/1993 |
| EP | 0101910 A1 | 3/1984 |
| EP | 0151886 A1 | 8/1985 |
| EP | 0201105 A1 | 11/1986 |
| EP | 0331021 A1 | 9/1989 |
| FR | 2743060 A1 | 7/1997 |
| GB | 287846 | 4/1929 |
| GB | 312345 | 8/1930 |
| GB | 470773 | 8/1937 |
| JP | 59025334 A | 2/1984 |
| JP | 5186392 A | 7/1993 |
| JP | 7053676 B2 | 6/1995 |
| SU | 362814 A1 | 12/1972 |
| WO | 2011131609 A2 | 10/2011 |
| WO | 2013055334 A1 | 4/2013 |
| WO | 2013116492 A1 | 8/2013 |

OTHER PUBLICATIONS

Filing receipt and specification for international application entitled "Ethyl acetate production," filed Oct. 20, 2010 as international application No. PCT/US2010/002806.
Filing receipt and specification for provisional patent application entitled "Production of butanols and ethyl acetate," by Sagar B. Gadewar, et al., filed Feb. 19, 2013 as U.S. Appl. No. 61/766,484.
Filing receipt and specification for provisional patent application entitled "Production of ethyl acetate and butyl acetates from ethanol," by Sagar B. Gadewar, et al., filed Dec. 4, 2013 as U.S. Appl. No. 61/911,832.
Filing receipt and specification for international application entitled "Production of higher alcohols," filed Feb. 18, 2014 as international application No. PCT/US2014/016957.
Filing receipt and specification for provisional patent application entitled "Production of higher alcohols from ethanol," by Brian Christopher Vicente, et al., filed Dec. 5, 2013 as U.S. Appl. No. 61/912,235.
Filing receipt and specification for provisional patent application entitled "Ethyl acetate production," by Sagar B. Gadewar, filed Oct. 20, 2009 as U.S. Appl. No. 61/253,349.

(Continued)

*Primary Examiner* — Brian J Davis

(74) *Attorney, Agent, or Firm* — Conley Rose, P.C.; Andrew M. Metrailer

(57) ABSTRACT

A reactive distillation method comprises introducing a feed stream to a reactive distillation column, contacting the feed stream with one or more catalysts in the reactive distillation column during a distillation, and removing one or more higher alcohols during the distillation from the reactive distillation column as a bottoms stream. The feed stream comprises one or more alpha hydrogen alcohols, and the feed stream reacts in the presence of the one or more catalysts to produce a reaction product comprising the one or more higher alcohols.

41 Claims, 12 Drawing Sheets

(56) References Cited

OTHER PUBLICATIONS

Foreign communication from a related counterpart application—International Search Report and Written Opinion, PCT/US2011/056015, May 24, 2012, 8 pages.

Foreign communication from a related counterpart application—International Preliminary Report on Patentability, PCT/US2011/056015, Apr. 15, 2014, 6 pages.

Foreign communication from a related counterpart application—International Search Report and Written Opinion, PCT/US2013/024104, May 30, 2013, 12 pages.

Inui, Kanichiro, et al., "Direct synthesis of ethyl acetate from ethanol carried out under pressure," Journal of Catalysis, 2002, pp. 207-215, vol. 212, Elsevier Science.

Inui, Kanichiro, et al., "Effective formation of ethyl acetate from ethanol over Cu—Zn—Zr—Al—O catalyst," Journal of Molecular Catalysis A: Chemical, 2004, pp. 147-156, vol. 216, Elsevier B.V.

Machine translation (9 pages) of French patent No. 2743060 A1 issued on Jul. 4, 1997.

Santacesaria, E., et al., "Ethanol dehydrogenation to ethyl acetate by using copper and copper chromite catalysts," Chemical Engineering Journal, 2012, pp. 209-220, vol. 179, Elsevier B.V.

Takeshita, Kenji, et al., "Reduced copper catalyzed conversion of primary alcohols into esters and ketones," Bulletin of the Chemical Society of Japan, Sep. 1978, pp. 2622-2627, vol. 51, No. 9.

Tsai, Reui-Chiang, et al., "Design and control of the side reactor configuration for production of ethyl acetate," Ind. Eng. Chem. Res., 2008, pp. 9472-9484, vol. 47, No. 23, American Chemical Society.

Yang, Ke Wu, et al., "One-step synthesis of n-Butanol from ethanol condensation over alumina-supported metal catalysts," Chinese Chemical Letters, 2004, pp. 1497-1500, vol. 15, No. 12.

Foreign communication from a related counterpart application—International Search Report and Written Opinion, PCT/US2014/016957, Jun. 27, 2014, 11 pages.

Foreign communication from a related counterpart application—International Search Report and Written Opinion, PCT/US2014/053894, Oct. 31, 2014, 9 pages.

\* cited by examiner

PRODUCTION OF HIGHER ALCOHOLS

CROSS-REFERENCE TO RELATED APPLICATIONS

This application claims the benefit of and priority to U.S. Provisional Patent Application No. 61/766,484, filed Feb. 19, 2013, entitled "Production of Butanols and Ethyl Acetate," and U.S. Provisional Patent Application No. 61/912,235, filed Dec. 5, 2013, entitled "Production of Higher Alcohols from Ethanol," each of which is incorporated herein by reference in its entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

N-Butanol and ethyl acetate are commercially significant organic compounds having use in a wide variety of applications and which are produced in quantities exceeding 1 million tons per year. N-Butanol can be produced from several different reactions. The most common method for making n-butanol is hydroformylation. Propylene reacts with syngas over cobalt or rhodium catalysts at high pressures to produce an aldehyde (butyraldehyde), which is then hydrogenated over a nickel catalyst to give the alcohol. The drawbacks of such a process include the high energy costs associated with the generation of syngas, the use of a potentially non-renewable feedstocks (propylene and syngas are typically sourced from petroleum and natural gas, respectively), and the complexity of the process which requires multiple reactors and, typically, homogenous hydroformylation catalysts.

N-Butanol can also be produced from an aldol condensation reaction followed by hydrogenation. This method converts acetaldehyde to butanols, although the high toxicity and limited availability of acetaldehyde make such a process unattractive. Some processes, for example U.S. Pat. Nos. 1,992,480 and 8,071,823 both of which are incorporated herein by reference in their entirety, utilize a gas phase reaction to provide butanol.

Direct fermentation of sugars is another process for production of n-butanol. As a bioprocess this method suffers from long process times and large separation requirements in addition to the need for specialized microbes necessary to make butanol directly from sugars.

Ethyl acetate can also be produced from several different reactions. The most common method for making ethyl acetate is the esterification of acetic acid and ethanol. This reaction requires two raw material supplies with the associated storage or production facilities. In locations without a sufficient supply of reliable, inexpensive acetic acid, this process may not be economically viable.

Ethyl acetate can also be produced from the oxidation of ethanol over supported precious metal catalysts. The high costs of precious metal catalyst can also make this option uneconomical.

The Tishchenko reaction (dimerization of aldehydes into esters) is another alternative process for production of ethyl acetate. Dimerization of acetaldehyde results in ethyl acetate, however, aldol condensation also occurs, resulting in by-products such as 2-butanone and 2-propanol, both of which form azeotropes with ethyl acetate. In addition, the Tishchenko reaction requires a supply of acetaldehyde, which may not be readily available and can be difficult to store and handle due to its high toxicity.

1-Hexanol and 1-octanol are both made industrially via oligomerization of ethylene using triethylaluminum, followed by oxidation of the alkylaluminum intermediate. In this process, the triethylaluminum does not serve as a catalyst, but rather is a reactant that is not easily regenerated. In particular, the reaction scheme starts with metallic aluminum and results in the formation of aluminum oxide and/or hydroxide upon completion of the reaction. The triethylaluminum is expensive since it requires metallic aluminum as a precursor. The triethylaluminum is also a pyrophoric material and presents hazards for using and storing. This process also requires a potentially non-renewable feedstock (ethylene) typically source from steam cracking of petroleum.

SUMMARY

In an embodiment, a reactive distillation method comprises introducing a feed stream to a reactive distillation column, contacting the feed stream with one or more catalysts in the reactive distillation column during a distillation, and removing one or more higher alcohols during the distillation from the reactive distillation column as a bottoms stream. The feed stream comprises one or more alpha hydrogen alcohols, and the feed stream reacts in the presence of the one or more catalysts to produce a reaction product comprising the one or more higher alcohols. The feed stream may further comprise water. The one or more alpha hydrogen alcohols may comprise one or more of ethanol, propanol, or butanol. The one or more alpha hydrogen alcohols may comprise only ethanol. The one or more higher alcohols may comprise a $C_4$-$C_{13}$ alcohol. The one or more higher alcohols may comprise at least one alcohol selected from the group consisting of: 1-butanol, 1-hexanol, 2-ethyl-1-butanol, 1-octanol, 2-ethyl-2-hexanol, heptanol, decanol, and dodecanols. The one or more catalysts may comprise a Guerbet reaction catalyst, a solid base multicomponent oxide catalyst, a solid acid/base bifunctional catalyst, a zeolite with alkali counterions, a magnesium oxide catalyst, an oxide powder catalyst, or any combination thereof. The one or more catalysts may comprise a dual function catalyst. The one or more catalysts may comprise a hydroxyapatite Guerbet reaction catalyst, a solid base Guerbet reaction catalyst, or a combination thereof. The one or more catalysts may comprise $CuO/SiO_2$, $CuO/SiO_2$—$Al_2O_3$, $CuO/ZnO$, $CuO/ZrO_2$, $CuO/SiO_2$—$ZrO_2$, $CuO/Al_2O_3$, $CuO/MgO$, $CuO/MgO/SiO_2$, $CuO/MgO/Al_2O_3$, $CuO/ZnO/SiO_2$, $CuO/ZrO_2/SiO_2$, $CuO/MgO/SiO_2$, $CuO/CaO/SiO_2$, $CuO/SrO/SiO_2$, $CuO/BaO/SiO_2$, $CuO/ZrO_2/Al_2O_3/SiO_2$ and $CuO/Na_2O/SiO_2$, $CuO/MgO/Al_2O_3/SiO_2$ $CuO/CeO2/MgO/Al_2O_3$, $CuO/ZnO/Al_2O_3$, $CuO/Cr_2O_3/Al_2O_3$, and $CuO/ZrO_2/Al_2O_3$, or any combination thereof. The one or more catalysts may comprise copper, and the copper may have a weight loading of between about 0.5% and about 80%. The one or more catalysts may comprise a catalyst component represented by the formula: $M/MgO/Al_2O_3$, where M can represent palladium, rhodium, platinum, silver, gold, nickel, or copper, or oxides thereof. The one or more catalysts may comprise a hydroxyapatite represented by the formula: $Ca_{10}(PO_4)_6(OH)_2$, where the ratio of calcium to phosphorus (Ca:P) can be between about 1.5 and about 1.8. The one or more catalysts may comprise an apatite structure satisfying the formula: $M_a(M'O_b)_cX_2$, where M represents calcium, strontium, magnesium, barium, lead, cadmium, iron, cobalt, nickel, zinc, or hydrogen, where M' represents phosphorus, vanadium, arsenic, carbon, or sulfur, where X represents a fluorine, chlorine, bromine, or a hydroxide, and where a is about 10, b is about 3, c is about 6, and the ratio of a to c is between about 1.5 and about 1.8. The one or more catalysts may comprise a calcium phosphate, a calcium phosphate carbonate, a calcium pyrophosphate, a magnesium phosphate, a magnesium phosphate carbonate, a magnesium pyrophosphate, magnesium oxide, magnesium hydroxide, magnesium phosphate hydrate ($Mg_3(PO_4)_2 \cdot 8H_2O$), calcium oxide, calcium hydroxide, calcium fluoride, calcium silicate (wollastonite), calcium sulfate dihydrate (gypsum), lithium phosphate, aluminum phosphate, titanium dioxide, fluorapatite ($Ca_{10}(PO_4)_6F_2$), tetracalcium phosphate ($Ca_4(PO_4)_2O$), hydrotalcite, talc, kaolin, sepiolite, or any combination thereof. The one or more catalysts may comprise at least one catalytic component selected from the group consisting of: copper, copper oxide, barium, barium oxide, ruthenium, ruthenium oxide, rhodium, rhodium oxide, platinum, platinum oxide, palladium, palladium oxide, rhenium, rhenium oxide, silver, silver oxide, cadmium, cadmium oxide, zinc, zinc oxide, zirconium, zirconium oxide, gold, gold oxide, thallium, thallium oxide, magnesium, magnesium oxide, manganese, manganese oxide, aluminum, aluminum oxide, chromium, chromium oxide, nickel, nickel oxide, iron, iron oxide, molybdenum, molybdenum oxide, sodium, sodium oxide, sodium carbonate, strontium, strontium oxide, tin, tin oxide, and any mixture thereof. The one or more catalysts may comprise a multi-component catalyst, and the multi-component catalyst may comprise a first catalyst component and second catalyst component. The first catalyst component may comprise a dehydrogenation catalyst component, and the second catalyst component may be configured to convert at least a portion of the one or more alpha hydrogen alcohols in the feed stream into the reaction product comprising the one or more higher alcohols and water. The one or more catalysts may comprise a support, and the support may comprise at least one support material selected from the group consisting of: carbon, silica, silica-alumina, alumina, zirconia, titania, ceria, vanadia, nitride, boron nitride, heteropolyacids, hydroxyapatite, zinc oxide, chromia, a zeolite, a carbon nanotube, carbon fullerene, and any combination thereof. The reactive distillation method may also include: removing a side stream from the reactive distillation column; contacting the side stream with a side reactor catalyst, where the side stream reacts in the presence of the side reactor catalyst to produce at least one of the one or more higher alcohols, and reintroducing the at least one of the one or more higher alcohols produced in the presence of the side reactor catalyst to the reactive distillation column. The side stream may comprise a vapor, and contacting the side stream with the side reactor catalyst may comprise contacting the vapor with the side reactor catalyst. The side stream may comprise a liquid, and contacting the side stream with the side reactor catalyst may comprise contacting the liquid with the side reactor catalyst. The reactive distillation method may also include adjusting a flow rate of the side stream to increase a production of the one or more higher alcohols.

The reactive distillation method may also include: removing a plurality of side streams from the reactive distillation column, introducing each of the plurality of side streams into a corresponding plurality of side reactors, where each of the plurality of side reactors comprise at least one side reactor catalyst, contacting each of the plurality of side streams with the at least one side reactor catalyst in the corresponding plurality of side reactors, where each of the plurality of side streams reacts in the presence of the one or more side reactor catalyst to produce a higher alcohol, and reintroducing the higher alcohol produced in the presence of the side reactor catalyst from each of the plurality of side reactors to the reactive distillation column. The reactive distillation method may also include adjusting a pressure of the reactive distillation column to increase a production of the one or more higher alcohols. The reactive distillation method may also include introducing a second feed stream comprising hydrogen to the reactive distillation column. The reactive distillation method may also include removing the bottoms stream from the reactive distillation column, where the one or more higher alcohols comprise one or more $C_6$-$C_{13}$ alcohols, and butanol, separating at least a portion of the one or more $C_6$-$C_{13}$ alcohols from one or more $C_2$-$C_5$ alcohols, and recycling the one or more $C_2$-$C_5$ alcohols to the reactive distillation column.

In an embodiment, a reactive distillation system comprises a reactive distillation column comprising: a catalyst located generally centrally in the column, an ethanol feed in fluid communication with the reactive distillation column and configured to pass ethanol over the catalyst, where the catalyst is configured to convert at least a portion of the ethanol feed into butanol in the reactive distillation column, an overhead product water removal passage, and a bottoms product higher alcohol removal passage; a product separation system comprising an inlet configured to receive the bottoms product from the reactive distillation column, a higher alcohol product removal passage, and an ethanol removal passage; and a recycle line coupling the ethanol removal passage from the product separation system and an inlet to the reactive distillation column. The reactive distillation column may comprise a continuous stirred-tank reactor (CSTR) configured to contact a liquid ethanol feed with the catalyst and remove water during the contacting of the liquid ethanol feed with the catalyst.

In an embodiment, a method of separating a mixed organic and aqueous phase stream, the method comprises: separating an inlet stream into an overhead stream and a bottoms stream in a separation unit, where the inlet stream comprises water, butanol, and an esters, where the overhead stream comprises the water and the ester, and where the bottoms stream comprises butanol, passing the overhead stream to a decanter, generating, in the decanter, an aqueous phase comprising substantially all of the water and an organic phase comprising the esters, removing the aqueous phase from the decanter as an aqueous stream, removing the organic phase from the decanter as an organics stream, separating the organics stream into a product stream and a recycle stream, where the product stream comprises the esters, and where the recycle stream comprises the water. The esters may comprise one or more of ethyl butyrate, ethyl acetate and butyl acetate. The separation unit may comprise one or more distillation columns.

In an embodiment, a method of separating a mixed organic and aqueous phase stream comprises: separating an inlet stream into an overhead stream and a bottoms stream in a separation unit, where the inlet stream comprises water, a plurality of higher alcohols, and an esters, where the overhead stream comprises the water the esters, and a first portion of the plurality of higher alcohols, and where the bottoms stream comprises a second portion of the plurality of higher alcohols, separating the bottoms stream into at least one product stream comprising a first higher alcohol of the first portion of the plurality of higher alcohols, passing the overhead stream to a decanter, generating, in the decanter, an aqueous phase comprising substantially all of the water and an organic phase comprising the esters and the second portion of the plurality of higher alcohols, removing the aqueous phase from the decanter as an aqueous stream, removing the organic phase from the decanter as an organics stream, and separating the organics stream into a first stream comprising the esters and a second stream comprising the second portion of the plurality of higher alcohols. Separating the bottoms stream into at least one product stream may comprise: separating the bottoms stream into a first product stream comprising butanol and a second product stream comprising the remainder of the first portion of the plurality of higher alcohols. Separating the bottoms stream into at least one product stream may further comprise: separating the remainder of the first portion of the plurality of higher alcohols into a third product stream comprising hexanol. Separating the organics stream into a first stream comprising the esters and a second stream comprising the second portion of the plurality of higher alcohols may comprise: separating the organics stream into a second overhead stream comprising the esters and water and a second bottoms stream comprising the second portion of the plurality of higher alcohols. Separating the organics stream into a first stream comprising the esters and a second stream comprising the second portion of the plurality of higher alcohols may further comprise: passing the second overhead stream to a second decanter, generating, in the second decanter, a second aqueous phase comprising substantially all of the water in the organics stream and a second organic phase comprising the esters, removing the second aqueous phase from the second decanter as a second aqueous stream, removing the second organic phase from the second decanter as a second organics stream, separating the second organics stream into an esters product stream comprising the esters. Separating the organics stream into a first stream comprising the esters and a second stream comprising the second portion of the plurality of higher alcohols may further comprise: separating the second bottoms stream into a third overhead stream and a third bottoms stream, where the third overhead stream comprises at least one higher alcohol of the second portion of the plurality of higher alcohols. Separating the second bottoms stream into a third overhead stream and a third bottoms stream may occur at a pressure greater than about 3 atmospheres. Separating the organics stream into the first stream comprising the esters and the second stream comprising the second portion of the plurality of higher alcohols may occur in a distillation system, and the distillation system may comprise a distillation column and at least one rectifiers or stripper in fluid communication with the distillation column.

In an embodiment, a method of separating an alcohol from butyl acetate, the method comprises adding water to an inlet stream to form a combined stream, where the inlet stream comprises an alcohol and butyl esters, distilling the combined stream to produce an overhead stream and a bottoms stream, where the overhead stream comprises a water and the ethyl acetate, and where the bottoms stream comprises a majority of the alcohol, condensing the overhead stream, and decanting an aqueous phase stream from an organic phase stream, where the aqueous phase stream comprises a majority of the water in the overhead stream, and where the organic phase stream comprises a majority of the butyl acetate in the overhead stream.

These and other features will be more clearly understood from the following detailed description taken in conjunction with the accompanying drawings and claims.

BRIEF DESCRIPTION OF THE DRAWINGS

For a more complete understanding of the present disclosure and the advantages thereof, reference is now made to the following brief description, taken in connection with the accompanying drawings and detailed description.

DETAILED DESCRIPTION

Figure 1A:
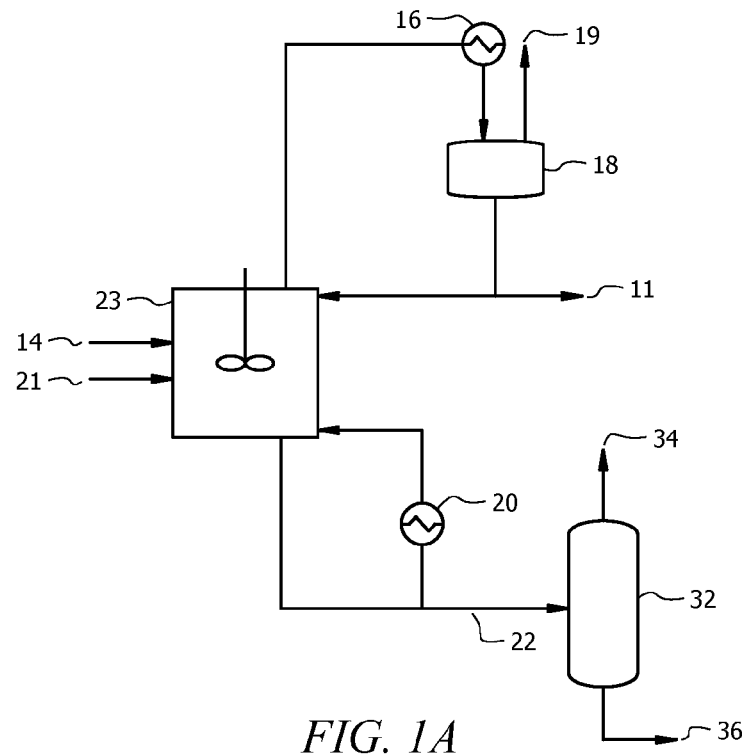
FIGS. 1(a) and 1(b) shows a simplified schematic of a reactive distillation system according to an embodiment.

A reactive distillation system and process are disclosed herein for producing higher linear and branched alcohols in a single reactor or a reactive distillation process from ethanol. As used herein, higher alcohols refer to alcohols have a higher molecular weight than the alcohol forming the reactant in the formation process. The higher alcohols can include n-butanol as well as significant amounts of 1-hexanol, 2-ethylbutanol, 1-octanol, 2-ethylhexanol, and other higher alcohol isomers (e.g., isomers of hexanol, octanol, etc.). This process is beneficial as it provides an improved commercial method of upgrading ethanol to higher alcohols such as n-butanol, which are more valuable products. This improved commercial process may be used where there is a supply and/or a surplus supply of ethanol. Further, this process reduces and/or eliminates the need for separate syngas and n-butyraldehyde plants to provide the precursors for the butanol production process, and reduces and/or eliminates reliance on syngas as a precursor, which is expensive to produce and requires a non-renewable resource when obtained from petroleum and natural gas. This process also reduces and/or eliminates the need for a separate acetaldehyde plant to provide the precursors for the butanol production process, and reduces and/or eliminates reliance on highly toxic acetaldehyde.

The raw material of this process may comprise only ethanol, which may present an advantage relative to other processes requiring multiple feedstocks. In addition, bio-derived ethanol may be used to allow the process to be operated from renewable ethanol sources. Further, the present system and method may utilize base-metal catalysts, which may be less expensive than the precious metal based catalysts of other butanol production routes and faster than microbial fermentation. Such catalysts can comprise copper, and may be composed of copper oxide mixed with one or more additional metals and/or metal oxides. The present systems and methods may allow for a one-step butanol production process, which may be advantageous relative to other processes that require a complex arrangement of reactors and catalysts or a complex separation scheme. Each of these advantages may be provided in a process that can also be less expensive than alternative processes by butanol production from ethanol.

Also disclosed herein is a reactive distillation system and process for co-producing high purity higher alcohols and ethyl acetate from ethanol. This process is beneficial as it provides an improved commercial method of upgrading ethanol to higher alcohols and/or ethyl acetate, which are more valuable products. The process may be tuned to allow the relative proportion of each product to be controlled, thereby allowing for the controlled selection of the product based on commercial considerations such as the cost of each product. Moreover, this commercial process may be used where there is a supply and/or a surplus supply of ethanol. Like the process for producing higher alcohols such as butanol, this process reduces and/or eliminates the need for a separate acetaldehyde, acetic acid, syngas, or n-butyraldehyde plant to provide the precursors for the process, and reduces and/or eliminates reliance on syngas and acetaldehyde precursors. While various alcohols can be used in the feed, the raw material may comprise only ethanol, which may present an advantage relative to other processes requiring multiple feedstocks. In addition, bio-derived ethanol may be used to allow the process to be operated from renewable ethanol sources.

This process is further beneficial in that higher alcohols and/or ethyl acetate may be produced in a single step from the same process equipment. This single step production may advantageously eliminate capital expenditures, operational costs, and additional space requirements that would otherwise be necessary if higher alcohols and ethyl acetate were produced separately. This single step production may also advantageously avoid costly plant shutdowns that would otherwise be necessary to switch from one product to the other in a process capable of producing only one product at a time. This process is also beneficial in that the relative amounts of higher alcohols and/or ethyl acetate can be adjusted during continuous operation to accommodate changes in market demand for one product relative to another. The present systems and methods may allow for a one-step higher alcohols and/or ethyl acetate production process, which may be advantageous relative to other processes that require further steps to purify the ethyl acetate-product, including a selective removal of 2-butanone, which forms a low boiling azeotrope with ethyl acetate. Each of these advantages may be provided in a process that can also be less expensive than alternative processes for ethyl acetate production from ethanol.

In an embodiment, the reaction to make higher alcohols from ethanol is believed to proceed through the Guerbet reaction mechanism. The initial step comprises a dehydrogenation of ethanol to form acetaldehyde. The acetaldehyde may then undergo an aldol condensation reaction to form an aldol intermediate that subsequently may be dehydrated to form crotonaldehyde. The crotonaldehyde can then be hydrogenated to butyraldehyde, which may further be hydrogenated to 1-butanol. Heavier alcohols can be generated in the same manner, only butyraldehyde, crotonaldehyde, or 1-hexanal participate in the aldol condensation reaction with acetaldehyde (or any other aldehyde present in the reaction mixture) resulting in 2-ethylalkyl alcohols (2-ethylbutanol, 2-ethylhexanol). An aldol condensation of the intermediate crotonaldehyde with acetaldehyde and butyraldehyde is the route that leads to 1-hexanol and 1-octanol respectively. Ethyl acetate may be produced by dehydration and dehydrogenation. These routes are capable of yielding high purity higher alcohols and/or ethyl acetate from alcohol feed streams (e.g., an ethanol feed stream) containing significant amounts of impurities. One issue in the production of higher alcohols and/or ethyl acetate is that the reaction product mixture is commonly a complex mixture including esters, alcohols, aldehydes and ketones. From a distillative separation point of view, the mixture is further complicated due to the presence of azeotropes. The reaction product mixtures may contain components with boiling points close to the produced higher alcohols that can include n-butanol (such as isobutanol), isomers of hexanol, octanol, and ethyl acetate (such as n-butyraldehyde, butan-2-one, or a combination thereof), including components which can form azeotropes with one or more of the higher alcohol products, ethyl acetate, other components of the mixture, or any combination thereof. This may present a challenge when one or more high purity higher alcohols and/or high purity ethyl acetate are desired.

In chemical processing, chemical reaction and the purification of the desired products by distillation may be carried out sequentially. The performance of this chemical process structure may be improved by the integration of reaction and distillation in a single multifunctional process unit. This integration concept is called "reactive distillation." The reaction may occur within the same vessel, or a second vessel in fluid communication with a separation vessel may be considered a reactive distillation. For example, a side reactor carrying out a reaction that is in fluid communication with a distillation column that removes at least a portion of the products would be considered a reactive distillation process. As advantages of this integration, chemical equilibrium limitations may be overcome, higher selectivities may be achieved, the heat of reaction may be used in situ for distillation, auxiliary solvents may be avoided, azeotropic and/or closely boiling mixtures may be more easily separated, or any combination thereof. Increased process efficiency and reduction in overall capital costs may result from the use of this approach.

A reactive distillation system comprises at least one separator (e.g., a distillation tower) in which a reaction is occurring. In general, suitable separators may include any process equipment suitable for separating at least one inlet stream into a plurality of effluent streams having different compositions, states, temperatures, and/or pressures. For example, the separator may be a column having trays, packing, or some other type of complex internal structure. Examples of such columns include scrubbers, strippers, absorbers, adsorbers, packed columns, and distillation columns having valve, sieve, or other types of trays. Such columns may employ weirs, downspouts, internal baffles, temperature control elements, pressure control elements, or any combination thereof. Such columns may also employ some combination of reflux condensers and/or reboilers, including intermediate stage condensers and reboilers. In an embodiment, the reactive distillation system described herein may comprise a distillation tower having at least one catalyst disposed therein.

As indicated above, the present systems and methods provide for the production of higher alcohols from ethanol and/or for the production of higher alcohols and/or ethyl acetate at a relatively low cost, along with plants or distillation systems with significantly reduced complexity using reactive distillation. The present disclosure further provides improved processes for the production of one or more high purity higher alcohols and for the production of high purity higher alcohols and/or ethyl acetate from a lighter alcohol feed or from a feedstock comprising a major proportion of a lighter alcohol feed and a minor proportion of impurities such as iso-propanol, iso-butanol, water, or any combination thereof. While not commonly present in alcohol feed streams, impurities that can poison the particular catalyst used should be limited, avoided and/or removed. For example, sulfur or nitrogen heterocyclic compounds can frequently act as catalyst poisons and, if present, should be removed before introducing the alcohol feed stream to the reactive distillation column. In an embodiment, the alcohol feed may comprise water. The presence of water in the alcohol feed does not severely reduce the performance of the catalysts, which can tolerate up to about 5% water by weight in the alcohol feed. Alcohol conversion is reduced when using an alcohol source with significant water content, but the reaction selectivity may increase for some products. The use of an alcohol feed comprising a small amount of water may be advantageous by allowing for the use a potentially less expensive alcohol source in the form of the alcohol/water azeotrope (e.g., about 4.4% water by weight in an ethanol feed). The effects of water are demonstrated in the Examples described herein.

Direct synthesis of higher alcohols from ethanol offers a potentially viable alternative to the hydroformylation process and ethylene oligomerization process described above. In the direct synthesis of higher alcohols from ethanol, the ethanol, which is a readily available and renewable feedstock, is converted to a mixture $C_4$-$C_{13}$ alcohols, and potentially higher alcohols. In an embodiment, the ethanol feedstock can be converted to one or more of n-butanol, 1-hexanol, 2-ethyl-1-butanol, 1-octanol, 2-ethyl-2-hexanol, decanols, dodecanols, and potentially longer chain alcohols in a single reactor or a reactive distillation apparatus over a solid catalyst. As noted above, the reaction to make higher alcohols from ethanol is generally believed to proceed through the Guerbet reaction mechanism.

As an example of a reaction mechanism for producing a higher alcohol, butanol may be produced from ethanol in the presence of one or more catalysts according to the following overall dehydration reaction:

$$C_2H_5OH + C_2H_5OH \leftrightarrows C_4H_9OH + H_2O \quad \text{(Eq. 1)}$$

While not intending to be limited by theory, it is believed that the overall reaction may proceed according to one or more of the following reactions in the presence of a catalyst:

$$C_2H_5OH \leftrightarrows CH_3CHO + H_2 \quad \text{(Eq. 2)}$$

$$CH_3CHO + CH_3CHO \leftrightarrows CH_3CH=CHCHO + H_2O \quad \text{(Eq. 3)}$$

$$CH_3CH=CHCHO + 2H_2 \leftrightarrows C_4H_9OH \quad \text{(Eq. 4)}$$

$$C_4H_8O + H_2 \leftrightarrows C_4H_9OH \quad \text{(Eq. 5)}$$

The production of butanol and/or ethyl acetate from ethanol can be produced according to the following dehydration and dehydrogenation reactions which can occur in the presence of one or more catalysts:

$$C_2H_5OH + C_2H_5OH \leftrightarrows C_4H_9OH + H_2O \quad \text{(Eq. 1)}$$

$$C_2H_5OH \leftrightarrows CH_3CHO + H_2 \quad \text{(Eq. 2)}$$

$$CH_3CHO + C_2H_5OH \leftrightarrows CH_3COOC_2H_5 + H_2 \quad \text{(Eq. 6)}$$

In an embodiment, ethanol reacts in a single continuous reactive distillation column which provides sufficient residence time to achieve a relatively high conversion of ethanol. In an embodiment, the reactive distillation column may be configured to provide a conversion of ethanol of at least about 10% and a selectivity of at least about 60%, as described in more detail herein.

As noted above, higher alcohols refer to one or more alcohols have a higher molecular weight than the alcohol forming the reactant in the formation process. For example, butanol would be considered a higher alcohol when produced from ethanol. As used herein, the term "butanol" may refer to n-butanol or mixtures of n-butanol in combination with 2-butanol, isobutanol, tert-butanol, or a combination thereof except when specifically indicated otherwise. In an various embodiments, butanol refers to n-butanol or mixtures of n-butanol in combination with 2-butanol, isobutanol, tert-butanol, or a combination thereof, wherein n-butanol is the majority component by weight. In addition to butanol, higher alcohols may generally comprise any $C_4$-$C_{13}$ alcohols, or even higher molecular weight alcohols.

With respect to the alcohol forming the reactant in the formation process, the present description is generally described in terms of ethanol. However, a number of alcohols can form the reactant. In some embodiments, the process is believed to occur with a feed comprising any alcohol comprising an alpha hydrogen in regard to the hydroxyl group (e.g., an alpha hydrogen alcohol) including, but not limited to, a primary or secondary alcohol. In an embodiment, the feed may comprise one or more alcohols other than methanol and may include any $C_2$-$C_5$ alpha hydrogen alcohols. In addition to ethanol, additional alcohols can be used in the reaction feed including, but not limited to, propanol, isopropanol, butanol, isobutanol, pentanol, etc.

The present systems and methods provide a reactive distillation system in which an alcohol feed comprising an alcohol having an alpha hydrogen is fed to a reactive distillation column. In an embodiment, ethanol may be the sole or primary component of the feed. Reference to a "single feed" to a reactive distillation column means that the column has only one chemical feed stream supplying intended reactant(s) to the column. Nonetheless, such a single feed distillation column may have multiple entry points for the reactant, or recycling feed streams where a part of the reactant liquid or a partial distillate is drawn from the column and fed back into the column at a different point, e.g., to achieve improved separation and/or more complete reaction.

The single feed may comprise a single reactant such as an alpha hydrogen alcohol (e.g., ethanol). A "single alcohol feed" refers to a feed stream of a single alpha hydrogen alcohol, and a "single ethanol feed" refers to a single feed stream in which ethanol is the sole or at least the primary constituent. The single feed may also comprise more than one reactant, such as a feed stream of ethanol and water, or a feed stream comprising a plurality of alpha hydrogen alcohols. A "single ethanol and water feed" thus refers to a single feed stream in which ethanol and water are the sole or at least the primary constituents. In contrast, the term "dual feed" in the context of a distillation column refers to two separate chemical feed streams. For example, in some of the present embodiments, dual feeds can include an ethanol feed stream and a separate hydrogen feed stream. As another example, in some embodiments, dual feeds can include an ethanol and water feed stream and a separate hydrogen feed stream. Analogously, the term "triple feed" in the context of a distillation column refers to three separate chemical feed streams. For example, in some of the present embodiments, three feeds are an ethanol feed stream (or, alternatively, an ethanol and water feed stream), a separate water feed stream, and a separate hydrogen feed stream. As a further example, in some of the present embodiments, three feeds can include an ethanol feed stream, a propanol feed stream, and a separate hydrogen feed stream.

The term "reactive distillation column" is used conventionally to refer to a distillation column in which and separation is performed while a reaction is occurring. The reaction may occur within the same distillation column, or a second vessel in fluid communication with a distillation column may still be considered a reactive distillation column. For example, a side reactor carrying out a reaction that is in fluid communication with a distillation column that removes at least a portion of the products would be considered a reactive distillation process occurring in a reactive distillation column.

In general, higher alcohols are produced by the addition of one or more lighter alcohols and/or side products. In embodiments where the production of butanol is desired, the primary and desired reaction is the conversion of two ethanol molecules to one butanol molecule with release of one water molecule. To this end, the present application provides systems and methods for the production of higher alcohols from an alpha hydrogen alcohol such as ethanol, which includes reacting one or more alpha hydrogen alcohols over a suitable catalyst in a reactive distillation column, thereby producing higher alcohols and water. In embodiments where the production of higher alcohols and/or ethyl acetate is desired, the primary and desired reactions include the conversion of two alpha hydrogen molecules to one higher alcohol molecule with release of one water molecule and the conversion of two ethanol molecules to one ethyl acetate molecule with release of two hydrogen molecules. To this end, the present application provides systems and methods for the production of higher alcohols and/or ethyl acetate from an alpha hydrogen alcohol, which includes reacting one or more alpha hydrogen alcohols over a suitable catalyst in a reactive distillation column, thereby producing one or more higher alcohols, ethyl acetate, water, and any combination thereof. In some embodiments byproducts may also be produced as described in more detail herein.

In an embodiment, a single reactive distillation column is used. Water is removed (e.g., continuously) from the top of the reactive distillation column as an overhead stream. In some embodiments, the overhead stream may comprise some amount of the alpha hydrogen alcohol(s) present in the feed such as ethanol. Higher alcohols can be removed (e.g., continuously) from the bottom of the column as a bottoms stream. Optionally, contaminating byproducts present following reaction of the alpha hydrogen alcohol(s) over the conversion catalyst can be reacted over a suitable hydrogenating catalyst in the lower part of the column or in a separate hydrogenation reactor. The hydrogenation can convert difficult to separate byproducts into species which are easier to separate from the higher alcohol(s). Consequently, the process can also include purifying the higher alcohols, including separating one or more higher alcohols, by distilling out resulting hydrogenated byproducts.

In some embodiment, a single reactive distillation column is used to co-produce higher alcohols and ethyl acetate. Hydrogen gas and liquid water are removed (e.g., continuously) from the top of the reactive distillation column as overhead streams. Higher alcohols and ethyl acetate are removed (e.g., continuously) from the bottom of the column as a bottoms product stream. After leaving the reactive distillation column, the bottoms product stream can be subjected to further separation to isolate the higher alcohols from the ethyl acetate, thus producing high purity product streams of each. Optionally, contaminating byproducts present following reaction of the alpha hydrogen alcohols over the conversion catalyst can be reacted over a suitable hydrogenating catalyst in the lower part of the column or in a separate hydrogenation reactor. The hydrogenation can convert difficult to separate byproducts into species which are easier to separate from the higher alcohols, the ethyl acetate, or a combination thereof. Consequently, the process may also include purifying the higher alcohols and ethyl acetate products by separating (e.g., distilling) resulting hydrogenated byproducts.

In an embodiment, the reactive distillation column is configured for the dehydration of an alpha hydrogen alcohol (e.g., ethanol) with the formation of a higher alcohol (e.g., butanol). The reaction is accomplished by passing the alpha hydrogen alcohol feed stream over a suitable catalyst under conditions where higher alcohols are formed, water and any unreacted alpha hydrogen alcohols are withdrawn as top products, and the higher alcohols can be withdrawn as a bottoms product. Such product draws drive the thermodynamics of the process toward the desired products. In its simplest form, a reactive distillation system may comprise a reactor vessel operating with a liquid phase reaction in which water and any unreacted alpha hydrogen alcohols are removed as the overhead product and a reaction product is removed as the bottoms product. The reactor vessel can comprise a continuous stirred-tank reactor (CSTR). Alternatively, such a system may comprise a batch reactor in which water and any unreacted alpha hydrogen alcohols are removed during the reaction and the liquid product is removed after completion of the reaction to a desired degree of conversion.

In an embodiment, the reactive distillation column is configured for the dehydration of an alpha hydrogen alcohol (e.g., ethanol) with the formation of higher alcohols (e.g., butanol) and the dehydrogenation of the alpha hydrogen alcohol (e.g., ethanol) with the formation of ethyl acetate. The reactions may be accomplished by contacting the alpha hydrogen feed stream with one or more suitable catalysts (e.g., a dehydrating and dehydrogenation catalyst) under conditions where higher alcohols and ethyl acetate are formed, water and hydrogen are withdrawn as top products, and the higher alcohols and ethyl acetate are withdrawn as bottoms products. By withdrawing the products from the distillation column, the thermodynamics of the process can be driven towards the desired products. In its simplest form, a reactive distillation system may comprise a reactor vessel operating with a liquid phase reaction in which water and/or other light gases are removed as the overhead product and a reaction product is removed as the bottoms product. Such a system may comprise a batch reactor in which water is removed during the reaction and the liquid product is removed after completion of the reaction to a desired degree of conversion.

In a simplistic form, as shown in FIG. 1(a), the reactive distillation system may comprise a continuous stirred-tank reactor (CSTR) charged with a catalyst that is coupled to a phase separator and configured for the dehydration of an alpha hydrogen alcohol with the formation of one or more higher alcohols, the dehydration and dehydrogenation of the alpha hydrogen alcohol with the formation of one or more higher alcohols and ethyl acetate (e.g., the production of higher alcohols and/or ethyl acetate), or a combination thereof. In an embodiment, production of higher alcohols may be accomplished by passing the feed stream 14, which comprises a feed of an alpha hydrogen alcohol or an alpha hydrogen alcohol and water, into the CSTR 23 wherein the feed mixes and contacts the dehydrating catalyst under conditions where higher alcohols and water are formed. As the conversions proceed, the resulting mixture may pass to a phase separator 32 from which the water leaves as distillate 34 and higher alcohols including any butanol or heavier alcohols can leave as a bottom product 36. Phase separator 32 may be any phase separator, which is a vessel that separates an inlet stream into a substantially vapor stream and a substantially liquid stream, such as a knock-out drum, flash drum, reboiler, condenser, or other heat exchanger. Such vessels also may have some internal baffles, temperature control elements, pressure control elements, or any combination thereof, but generally lack any trays or other type of complex internal structure commonly found in columns. In another embodiment, the production of higher alcohols and/or ethyl acetate may be accomplished by passing a feed stream 14, which comprises a feed of one or more alpha hydrogen alcohols or one or more alpha hydrogen alcohols and water, and, optionally, a hydrogen feed stream 21 into the CSTR 23 wherein the alpha hydrogen alcohols and any water and/or hydrogen mixes and contacts the conversion catalyst under conditions where one or more higher alcohols, ethyl acetate, water, and hydrogen are formed. As the conversions proceed, the resulting mixture may pass to a phase separator 32 where hydrogen, water, and any unreacted alpha hydrogen alcohols are removed as overhead product stream 34 while higher alcohols and ethyl acetate are removed as a bottoms product stream 36.

Figure 1B:
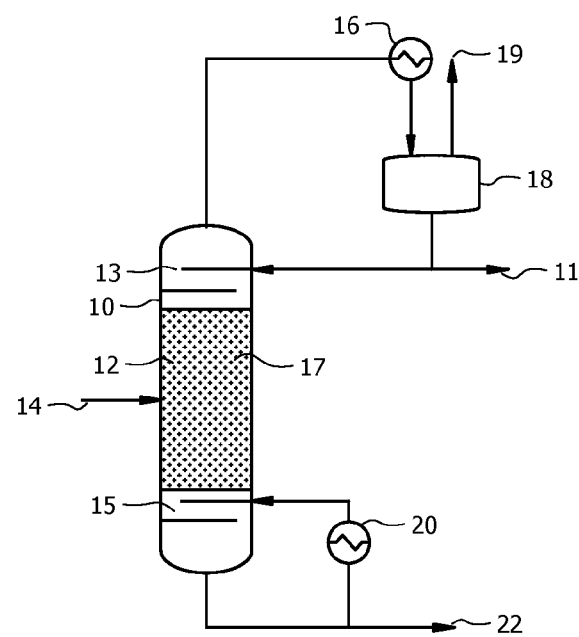

An embodiment of a reactive distillation column with a single alpha hydrogen feed, for example a single feed of ethanol, is shown schematically in FIG. 1(b). Column 10 contains a generally central catalyst zone 12, and usually will include a top stage or non-reactive rectifying section 13 and a bottom stage or non-reactive stripping section 15. The alpha hydrogen alcohol feed 14 may be fed to the middle part of the reactive distillation column. While illustrated as having the catalyst 17 disposed within the central portion of the column 10, the catalyst 17 may be located only above or below the alpha hydrogen alcohol feed location. In an embodiment, the catalyst 17 may be disposed only above the feed location, and the lower portion of the column 10 may comprise trays, packing, or the like to provide a stripping section. In some embodiments, the catalyst 17 may be disposed only below the feed location, and the upper portion of the column 10 may comprise trays, packing, or the like to provide a rectifying section.

Distillate removed at the top of the column is passed through a partial condenser 16, and water is separated from lower boiling constituents in reflux tank 18. Higher boiling constituents may leave the system as an overhead product stream 19, which in an embodiment may comprise trace amounts of water, the alpha hydrogen alcohols in the feed (e.g., ethanol), higher alcohols (e.g., butanol, 2-butanol, isobutanol, etc.), one or more reaction byproducts, or any combination thereof. The condensate (e.g., the reflux), or at least some portion thereof, can be cycled back to the column for further reaction and/or separation. Condensate not cycled back to the column leaves as overhead product stream 11. The condensate comprises water and, in some embodiments, the alpha hydrogen alcohols from the feed. The condensate may also comprise trace amounts of additional components including alpha hydrogen alcohol(s) from the feed, higher alcohols, one or more reaction byproducts, or any combination thereof. In an embodiment, a portion of the condensate comprising water and the alpha hydrogen alcohol may be dehydrated and returned to the column 10. The bottoms product can be passed through reboiler 20, where a portion of the bottoms product is converted to vapor and introduced back to the lower portion of the column. The remaining bottoms product may pass out of the system as product stream 22. Alternatively, only a portion of the bottoms product may be passed through reboiler 20, with the vapor portion passing back to the lower portion of the column and the remainder of the bottoms product being combined with any bottoms product bypassing the reboiler 20 and passing out of the system as product stream 22 for further processes and/or use as a final product. The product stream 22 may comprise the higher alcohols produced in the column along with potentially any side products produced by the reaction. Some trace amounts of the feed alpha hydrogen alcohols may be present in the bottom stream 22. In an embodiment, the bottoms stream may comprise butanols, pentanols, any $C_6$-$C_{13}$ alcohols, heavier alcohols or any combination thereof. The column reflux and reboil ratios may be maintained such that one or more essentially pure higher alcohols can be obtained as the bottoms product. In an embodiment, the bottoms product stream 22 may comprise greater than about 90%, greater than about 95%, greater than about 96%, greater than about 97%, greater than about 98%, greater than about 99%, or greater than about 99.5% higher alcohol(s) by weight. In some embodiments, the bottoms product stream 22 may comprise greater than about 90%, greater than about 95%, greater than about 96%, greater than about 97%, greater than about 98%, greater than about 99%, or greater than about 99.5% butanol by weight.

During operation, the reactants and products flow through the reactor/column reacting and flashing along the length of the reactor/column. In an embodiment, the reaction of the reactants and/or products may occur in the catalyst zone 12, and the reactions may occur in the vapor and/or liquid phase. Specific catalysts useful in the reactive distillation systems and methods disclosed herein are discussed in more detail below. In an embodiment, the reaction of alpha hydrogen alcohol over the catalysts can occur in a vapor phase in which the ethanol is passed over the catalyst for a given residence time consistent with the desired selectivity and/or conversion. In an embodiment, the reaction of ethanol over the catalysts can occur in a liquid phase reaction where the catalyst can be dispersed in a liquid reactant mixture and/or reactants contact the catalyst in condensed state. A vapor phase reaction and liquid phase reaction would generally occur at similar temperatures, and the pressure of each reaction would depend on the state (e.g., vapor and/or liquid) of the reactants contacting the catalyst(s).

One or more higher alcohols and water can be produced, along with potential side products, due to the reaction over the catalyst. The removal of the overhead stream 11 comprising water, which may occur by flashing, increases the extent of reaction. In general, the water concentration increases from the middle part of the column towards the top of the column. A partial condenser 16 allows water to be removed as a distillate and/or recycled back to the top of the reactive distillation column. At pressures of about 0.1 bar or higher, an azeotrope occurs between ethanol and water when ethanol is present in the alpha hydrogen alcohol feed that is introduced with the feed and/or formed from the reactants. This azeotrope may result in the overhead product 11 that leaves the top of the reactive distillation column 10 containing unreacted ethanol in addition to water. In an embodiment, any unreacted ethanol leaving condenser 16 as overhead stream 11 can be fed to a dehydration unit to produce a dehydrated ethanol stream, which can then be recycled back to column 10 as feed.

The column 10 can be operated at any suitable pressure between about 1 atm and about 80 atm. In an embodiment, the column 10 may be operated at a pressure ranging from about 1 atm to about 5 atm, about 5 atm to about 10 atm, about 10 atm to about 20 atm, about 15 atm to about 20 atm, about 15 atm to about 30 atm, about 20 atm to about 30 atm, about 20 atm to about 50 atm, about 30 atm to about 40 atm, about 40 atm to about 50 atm, or about 50 atm to about 60 atm, about 60 atm to about 70 atm, about 60 atm to about 80 atm, or about 70 atm to about 80 atm. The temperature profile in the column is dictated by the mixture boiling point along the height of the column. In an embodiment the temperature within the column may range from about 100° C. to about 400° C., about 150° C. to about 350° C., about 200° C. to about 325° C., about 230° C. to about 300° C., or about 260° C. to about 300° C. The column 10 may comprise any number of stages equivalent to a number of theoretical stages sufficient to effect the reaction and separation of the higher alcohols to a desired purity. In an embodiment, the number of stages or the number of height equivalents of a theoretical plate (HETP) may range from about 1 to about 100, including for example from about 1 to about 10, about 10 to about 20, about 10 to about 50, about 20 to about 30, about 20 to about 70, about 30 to about 40, about 30 to about 50, about 30 to about 100, about 50 to about 70, about 50 to about 100, or about 70 to about 100. As described in more detail below, a relatively high conversion of the alpha hydrogen alcohol(s) to products can be achieved by the counter-current flow of reactants and products in addition to overcoming the reaction equilibrium by removal of products through the concurrent distillation within the column 10.

In a reactive distillation process for making higher alcohols, the maximum temperature of the catalyst in the column can be controlled by adjusting the operating pressure of the column. By increasing the pressure, and therefore temperature, a greater yield of higher alcohols can be realized. The product distribution may also be pushed towards heavier molecular weight higher alcohols when the temperature increases. Similarly, by decreasing the operating pressure, and therefore temperature, the process can be adjusted to make less higher alcohols along with the product distribution being pushed towards lower molecular weight higher alcohols. Also, by selectively locating the catalyst section within the column 10, the temperature within the catalytic section can be controlled, thereby controlling the product distribution.

An alternative process for making higher alcohols directly from alpha hydrogen alcohols such as ethanol in a reactive distillation column with a single catalyst is to use multiple catalysts in a single process. In a reactive distillation column, the reactive sections could include both a catalyst for a first product (e.g., ethyl acetate, butanol, etc.) production and a catalyst for higher alcohols production. The catalysts in each section can be configured to react at the temperature in the portion of the column in which the catalyst(s) are located.

In an embodiment, the system of FIG. 1(b) can be used to co-produce butanol and ethyl acetate. In general, the process described above with respect to the production of one or more higher alcohols from a feed comprising one or more alpha hydrogen alcohols will be the same or similar when the coproduction of higher alcohols and ethyl acetate is desired. As a result, similar elements will not be described herein in the interest of brevity. The production of ethyl acetate along with higher alcohols may produce hydrogen as a reaction product. Distillate removed at the top of the column is passed through a partial condenser 16, and hydrogen is separated from higher boiling constituents in reflux tank 18. The hydrogen may leave the system as an overhead product stream 19, which in an embodiment may comprise trace amounts of additional components including the alpha hydrogen alcohol from the feed stream, ethyl acetate, one or more higher alcohols, water, one or more reaction byproducts, or any combination thereof. The bottoms product can be passed through reboiler 20, where a portion of the bottoms product is evaporated and added back to the lower portion of the column. The product stream 22 may comprise the higher alcohols and ethyl acetate produced in the column and potentially any portion of any side products produced by the reaction. The column reflux and reboil ratios can be maintained such that the bottoms product is essentially all higher alcohols and ethyl acetate. In an embodiment, the bottoms product stream 22 may comprise a combined amount of higher alcohols and ethyl acetate which accounts for greater than about 90%, greater than about 95%, greater than about 96%, greater than about 97%, greater than about 98%, greater than about 99%, or greater than about 99.5% of the total weight of the product stream 22.

In an embodiment, the ratio of higher alcohol(s) to ethyl acetate in product stream 22 may be affected by the catalyst used as well as the amount of water and/or hydrogen introduced to the column 10. With respect to the reactants, the ratio of higher alcohol(s) to ethyl acetate can be adjusted by adjusting an amount of water and/or hydrogen fed to column 10. An amount of water can be introduced with the alpha hydrogen alcohol feed as part of feed stream 14. An amount of hydrogen can be introduced with the alpha hydrogen alcohol, separately as feed stream 21, or a combination thereof. To increase the amount of higher alcohols produced relative to the amount of ethyl acetate produced, the amount of water introduced via feed stream 14 can be increased and/or the amount of hydrogen introduced to column 10 via feed stream 21 can be decreased. To increase the amount of ethyl acetate produced relative to the amount of higher alcohols produced, the amount of hydrogen introduced to column 10 via feed stream 21 can be increased and/or the amount of water introduced via feed stream 14 can be decreased.

In an embodiment, the systems and methods may also include hydrogenating contaminants or reaction byproducts in the bottoms stream or in the reacted fluid after it has passed over the higher alcohol conversion catalyst and separating the hydrogenated contaminants or byproducts from the higher alcohols. Species that may be produced as byproducts in the reaction may include aldehydes, such as acetaldehyde, n-butyraldehyde, and/or crotonaldehyde; ethers, such as ethyl ether and n-butyl ether; ethyl acetate. Various higher alcohols may also be produced including, but not limited to, isobutanol, 2-butanol, 2-ethylbutanol, n-hexanol, 2-ethylhexanol, 2-ethylbutanol, 1-octanol, other isomers of hexanol, and/or other isomers of octanol, and/or various higher alcohols and isomers thereof. Some of these byproducts boil at temperatures close to the boiling point of one or more desired higher alcohols and may be difficult to separate.

Figure 2:
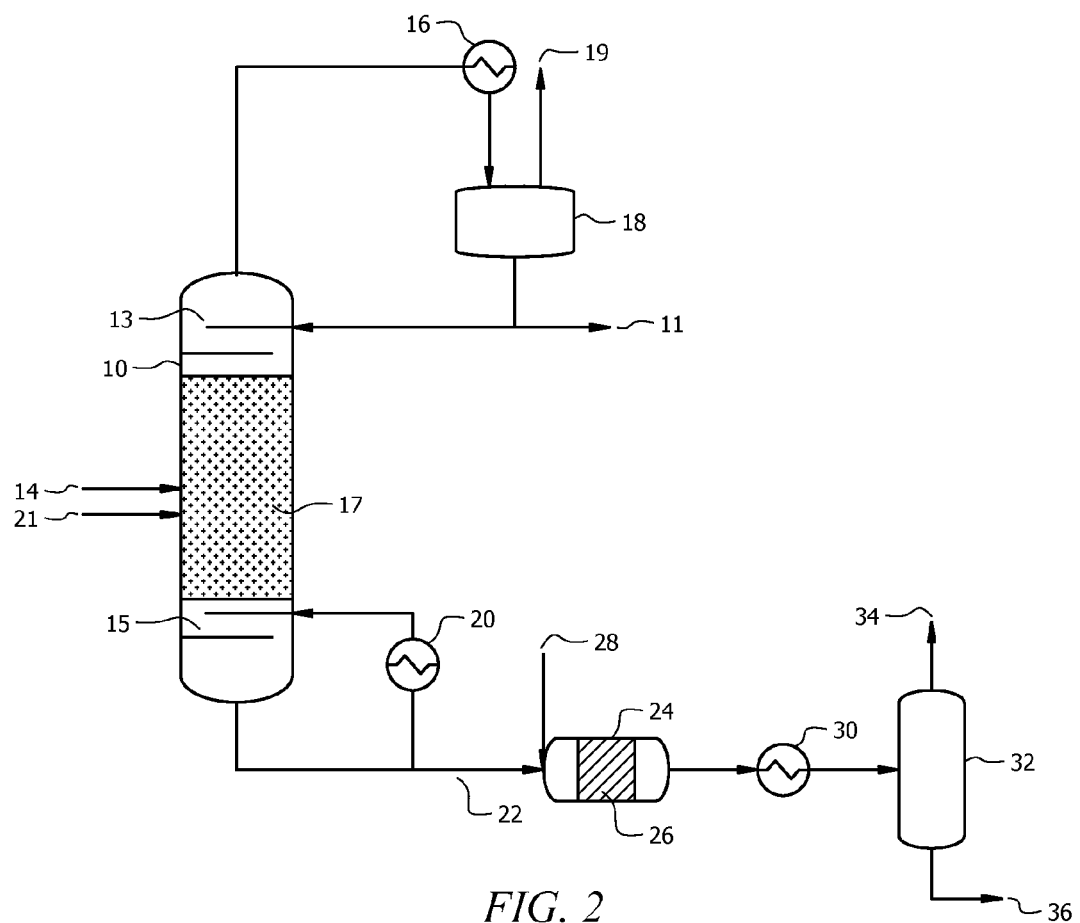
FIG. 2 shows a simplified schematic of a reactive distillation system according to still another embodiment.

FIG. 2 shows a process schematic where the bottoms product 22 from the reactive distillation column 10 illustrated in FIG. 1(b) is sent to a hydrogenation reactor 24 comprising a hydrogenating catalyst 26 with a hydrogen co-feed 28. Suitable hydrogenating catalyst(s) may comprise various components and are described in more detail herein. At least a portion of the byproducts can be hydrogenated, pass through heat exchanger 30, and can then be separated using a separator 32. The separator 32 may comprise any of the types of separators described herein with respect to the reactive distillation system. Alternatively or in addition to the separators already described, the separator 32 may be a phase separator, which is a vessel that separates an inlet stream into a substantially vapor stream and a substantially liquid stream, such as a knock-out drum, flash drum, reboiler, condenser, or other heat exchanger. Such vessels also may have some internal baffles, temperature control elements, pressure control elements, or any combination thereof, but generally lack any trays or other type of complex internal structure commonly found in columns. The separator also may be any other type of separator, such as a membrane separator. In a specific embodiment, the separator is a knockout drum. Finally, the separator may be any combination of the aforementioned separators arranged in series, in parallel, or combinations thereof. In an embodiment, separator 32 comprises a distillation column. The outlet of the hydrogenation reactor 24 may be passed through a heat exchanger 30 (e.g., a condenser) and cooled before entering the separator 32. The heat exchanger 30 may be any equipment suitable for heating or cooling one stream using another stream. Generally, the heat exchanger 30 is a relatively simple device that allows heat to be exchanged between two fluids without the fluids directly contacting each other. Examples of suitable heat exchangers 30 include, but are not limited to, shell and tube heat exchangers, double pipe heat exchangers, plate fin heat exchangers, bayonet heat exchangers, reboilers, condensers, evaporators, and air coolers. In the case of air coolers, one of the fluids comprises atmospheric air, which may be forced over tubes or coils using one or more fans.

The bottoms product stream 36 from the separator 32 may comprise one or more higher alcohols (e.g., butanols, pentanols, etc.) and may have a purity of greater than about 90%, greater than about 95%, greater than about 96%, greater than about 97%, greater than about 98%, greater than about 99%, or greater than about 99.5% by weight. Unconverted water and the hydrogenated byproducts may be removed as an overhead product 34, and may be used, for example, as fuel or a feed to one or more processes. In an embodiment, the separator 32 may be operated between a pressure of 1 atm and 80 atm.

In an embodiment, the bottoms product stream 36 may pass to another separator. The separator may then separate the bottoms product stream into a higher alcohols stream and a byproduct stream comprising one or more heavier hydrogenation products produced in the hydrogenation reactor 26. The components within a mixed higher alcohols stream can be further separated to produce one or more product streams comprising predominately individual higher alcohols. This separation scheme may allow for one or more resulting higher alcohol streams to have individual component purities of greater than about 90%, greater than about 95%, greater than about 96%, greater than about 97%, greater than about 98%, greater than about 99%, or greater than about 99.5% of the respective higher alcohol by weight. In an embodiment, the product stream may have a purity of greater than about 90%, greater than about 95%, greater than about 96%, greater than about 97%, greater than about 98%, greater than about 99%, or greater than about 99.5% n-butanol by weight.

In an embodiment, the system of FIG. 2 can also be used to co-produce one or more higher alcohols and ethyl acetate. In general, the process described above with respect to the production of one or more higher alcohols from a feed comprising one or more alpha hydrogen alcohols in FIG. 2 will be the same or similar when the coproduction of higher alcohols and ethyl acetate is desired. As a result, similar elements will not be described with reference to FIG. 2 in the interest of brevity. FIG. 2 shows a process schematic where the bottoms product 22 from the reactive distillation column 10 illustrated in FIG. 1(b) is sent to a hydrogenation reactor 24 comprising a hydrogenating catalyst 26 with a hydrogen co-feed 28. Suitable hydrogenating catalyst(s) may comprise various components and are described in more detail herein. At least a portion of the byproducts can be hydrogenated and can then be separated using a separator 32. The separator 32 may comprise any of the types of separators described herein with respect to the reactive distillation system, including those discussed above with respect to separator 32. In an embodiment, separator 32 comprises a distillation column. The outlet of the hydrogenation reactor 24 may be passed through a heat exchanger 30 (e.g., a condenser) and cooled before entering the separator 32. The heat exchanger 30 may be any equipment suitable for heating or cooling one stream using another stream, and may include any of those types of heat exchangers discussed herein.

The bottoms product stream 36 from the separator 32 may comprise one or more higher alcohols and ethyl acetate. The combined weight of the higher alcohols and the ethyl acetate may comprise greater than about 90%, greater than about 95%, greater than about 96%, greater than about 97%, greater than about 98%, greater than about 99%, or greater than about 99.5% of the total weight of the bottoms product stream. Unconverted water, hydrogen, and the hydrogenated byproducts may be removed as an overhead product 34, and may be used, for example, as fuel or a feed to one or more processes. In an embodiment, the separator 32 may be operated between a pressure of 1 atm and 80 atm.

In an embodiment, the bottoms product stream 36 may pass to another separator. The separator may then separate the bottoms product stream into a stream comprising one or more higher alcohols and ethyl acetate and a byproduct stream comprising one or more heavier hydrogenation products produced in the hydrogenation reactor 26. This separation scheme may allow the resulting stream of higher alcohols and ethyl acetate to comprise greater than about 90%, greater than about 95%, greater than about 96%, greater than about 97%, greater than about 98%, greater than about 99%, or greater than about 99.5% of the total weight of the stream of higher alcohols and ethyl acetate.

In an embodiment, the stream comprising the one or more higher alcohols and ethyl acetate may pass to another separator. The separator may then separate the stream of butanol and ethyl acetate into an overhead stream of ethyl acetate and a bottoms stream predominately comprising the one or more higher alcohols. This separation scheme may allow the resulting overhead stream of ethyl acetate to have a purity of greater than about 90%, greater than about 95%, greater than about 96%, greater than about 97%, greater than about 98%, greater than about 99%, or greater than about 99.5% ethyl acetate by weight. This separation scheme may allow the resulting bottoms stream comprising the one or more higher alcohols to have a purity of greater than about 90%, greater than about 95%, greater than about 96%, greater than about 97%, greater than about 98%, greater than about 99%, or greater than about 99.5% higher alcohols by weight. In an embodiment, the resulting bottoms stream may comprise butanol have a purity of greater than about 90%, greater than about 95%, greater than about 96%, greater than about 97%, greater than about 98%, greater than about 99%, or greater than about 99.5% butanol by weight.

Figure 3A:
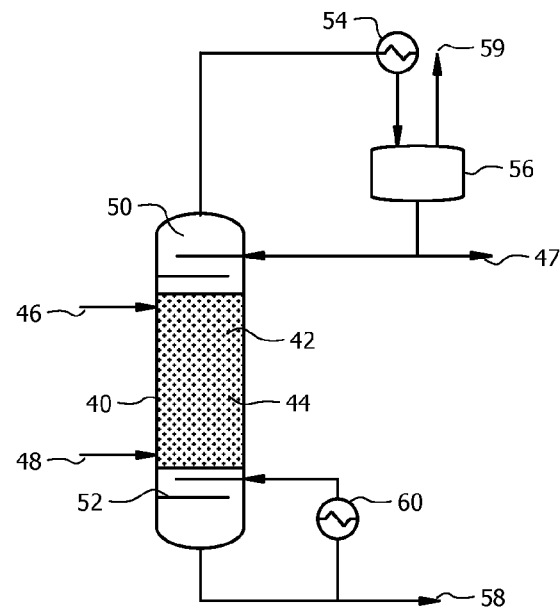
FIGS. 3(a) and 3(b) shows a simplified schematic of a reactive distillation system according to yet another embodiment.

In another embodiment of the invention, the reactive distillation column has two feeds. A schematic for the double feed reactive distillation column is schematically illustrated in FIG. 3(a). The feed stream comprising the alpha hydrogen alcohol feed may be fed to the upper part of the column (upper feed stream 46), and hydrogen may be fed to the lower part of the column (lower feed stream 48). This system includes column 40 containing catalyst 42 in catalyst zone 44, and commonly may include a top stage or non-reactive rectifying section 50 and a bottom stage or non-reactive stripping section 52. In the illustrated system, upper feed stream 46 is delivered at or near the top of the catalyst zone 44, and the lower feed stream 48 is delivered at or near the bottom of catalyst zone 44. In an embodiment, upper feed stream 46 comprises at least one alpha hydrogen alcohol and water. It should be recognized that columns can be designed with the upper feed stream 46 in other locations, e.g., within the catalyst zone 44 but above the lower feed stream 48, such as from the approximate middle of the catalyst zone 44 to the top of the column 40. Similarly, columns with the lower feed stream 48 in other locations can also be designed, e.g., with the lower feed stream 48 from the approximate middle of the catalyst zone 44 to the bottom of the column 40 or even higher within the catalyst zone 44 but below the upper feed stream 46. In an embodiment, the upper feed stream 46 and the lower feed stream 48 are separated sufficiently to allow byproduct hydrogenation to be substantially completed before hydrogen from the lower feed reaches substantial concentrations of the alpha hydrogen alcohol being dehydrogenated. The alpha hydrogen alcohol (e.g., ethanol) reacts over the catalyst producing one or more higher alcohols and water. Examples of conversion catalysts suitable for use in the production of one or more higher alcohols are described in more detail herein.

Due to boiling point differences, water tends to move towards the top of the column 40 and the higher alcohols tend to move towards the bottom of the column 40. Byproducts such as acetaldehyde, n-butyraldehyde, and ethyl ether may be produced during the reaction and may move up in the column 40. At least a portion of the byproducts, if present, can be condensed in condenser 54 (e.g., a partial condenser, or a total condenser), passed through reflux tank 56, and recycled back to column 40 as reflux. A product stream 47 comprising water is taken out as distillate from the reflux tank 56. In an embodiment, product stream 47 further may comprises unreacted alpha hydrogen alcohol(s) from the feed and can contain a portion of the byproducts (e.g., acetaldehyde, n-butyraldehyde, ethyl ether, crotonaldehyde, etc.). The product stream 47 comprising the alpha hydrogen alcohol and water can be fed to a dehydration unit to produce a dehydrated alpha hydrogen alcohol stream, which can then be recycled back to column 40 as feed. A portion of the bottom draw is taken out as the higher alcohol(s) product stream 58, while the remaining portion is passed through reboiler 60 to be recycled to the column 40. In an embodiment, the bottom draw may be passed through a reboiler (e.g., similar to reboiler 60) and optionally passed to a separator where the vapor portion may pass to the column 40 while at least a portion of the remainder is taken out as the higher alcohol(s) product stream 58. The stream passing through the reboiler 60 provides the evaporation effect and vapor flow for operating the column 40. In an embodiment, the product stream 58 may comprise the higher alcohol(s) produced in the column 40 and potentially any side products produced by the reaction.

Byproducts such as ethyl acetate and n-butyraldehyde produced in the reaction may have boiling points close to the boiling point of one or more higher alcohols such as butanol. The lower hydrogen feed 48 is useful in hydrogenating the by-products to produce components that can be more easily separated from the higher alcohol products. The ratio of the alpha hydrogen alcohol(s) feed to the hydrogen feed can beneficially be adjusted to minimize the amount of close boiling byproducts. In an embodiment, the molar ratio of the alpha hydrogen alcohol(s) to hydrogen ranges from about 1:10 to about 1000:1, e.g., from about 1:10 to about 1:1, from about 1:1 to about 5:1, from about 1:1 to about 10:1, from about 5:1 to about 25:1, from about 5:1 to about 50:1, from about 10:1 to about 50:1, from about 10:1 to about 100:1, from about 50:1 to about 200:1, from about 50:1 to about 400:1, from about 100:1 to about 500:1, from about 100:1 to about 1000:1, from about 200:1 to about 1000:1, or from about 500:1 to about 1000:1. Water product from the reaction leaves at the top of the column. In an embodiment, the column 40 may operate at any of the conditions (e.g., operating pressure, operating temperature, etc.) discussed herein with respect to column 10 in FIG. 1(*b*). In addition, the column 40 may have any number of stages, and in an embodiment have any number of stages as described with respect to column 10 in FIG. 1(*b*).

Figure 3B:
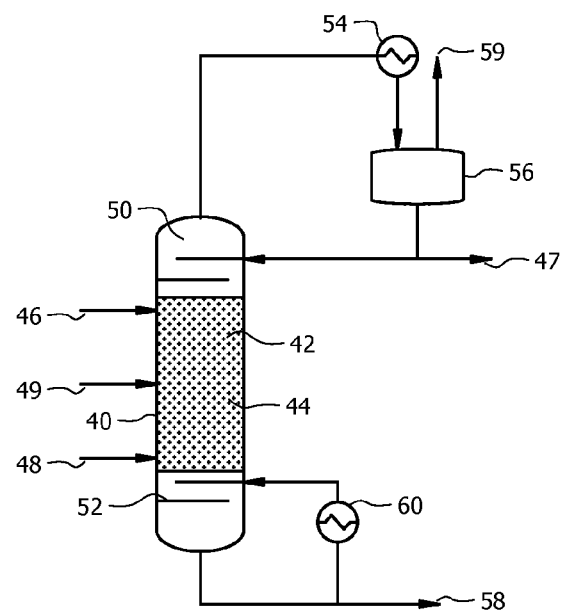

In another embodiment of the invention, the reactive distillation column comprises three feeds. A schematic for the triple feed reactive distillation column is schematically illustrated in FIG. 3(*b*). A feed 46 comprising at least one alpha hydrogen alcohol may be fed to the upper part of the column (upper feed stream), a feed stream 48 comprising hydrogen may be fed to the lower part of the column (lower feed stream), and an intermediate feed stream 49 may be fed to a part of the column between the upper and lower parts of the column. In an embodiment, the intermediate feed stream 49 may comprise water. This system includes column 40 containing catalyst 42 in catalyst zone 44, and commonly may include a top stage or non-reactive rectifying section 50 and a bottom stage or non-reactive stripping section 52. In the illustrated system, the upper feed stream 46 is delivered at or near the top of the catalyst zone 44, the lower feed stream 48 is delivered at or near the bottom of catalyst zone 44, and the feed stream 49 is delivered at or near the middle of the catalyst zone, between the upper feed stream 46 and the lower feed stream 48. In an embodiment, intermediate feed stream 49 comprises an alpha hydrogen alcohol and water. In some embodiments, the intermediate feed stream 49 may comprise an alpha hydrogen alcohol, which may be the same or different than the alpha hydrogen alcohol in the upper feed stream 46. It should be recognized that columns can be designed with the alpha hydrogen alcohol feed stream 46 in other locations, e.g., within the catalyst zone 44 but above the lower feed stream 48 and the intermediate feed stream 49, such as from the approximate middle of the catalyst zone 44 to the top of the column 40. Similarly, columns with the lower feed stream 48 in other locations, e.g., within the catalyst zone 44 but below the intermediate feed stream 49 and the upper feed stream 46, such as from the approximate middle of the catalyst zone 44 to the bottom of the column 40. Columns with the intermediate feed stream 49 in other locations can also be designed, e.g., with the intermediate feed stream 49 from the approximate middle of the catalyst zone 44 to the bottom of the column 40 but above the lower feed stream 48, or even higher within the catalyst zone 44 but below the upper feed stream 46. In an embodiment, the upper feed stream 46, the lower feed stream 48, and the intermediate feed stream 49 are separated sufficiently to allow byproduct hydrogenation to be substantially completed before the alpha hydrogen alcohol, and optionally water, or a combination thereof from the upper feed stream, the intermediate feed stream, or a combination thereof reaches substantial concentrations of hydrogen. The alpha hydrogen alcohol fed to the column reacts over the catalyst to produce one or more higher alcohols, ethyl acetate, water, and hydrogen. Examples of suitable hydration, dehydrogenation, and dimerization catalysts are described in more detail herein.

Due to boiling point differences, water and hydrogen tend to moves towards the top of the column 40 while the higher alcohols and any ethyl acetate tend to move towards the bottom of the column 40. Byproducts such as acetaldehyde, n-butyraldehyde, and ethyl ether may be produced during the reaction and may move up in the column 40. At least a portion of the byproducts, if present, can be condensed in condenser 54 (e.g., a partial condenser, or a total condenser), passed through reflux tank 56, and recycled back to column 40 as reflux. A product stream 59 comprising hydrogen is taken from the reflux tank 56. In an embodiment, product stream 59 further comprises ethyl ether. A product stream 47 comprising water may be taken from the reflux tank 56. In an embodiment, the product stream 47 may further comprise unreacted alpha hydrogen alcohol. The product stream 47 comprising the alpha hydrogen alcohol and water can be fed to a dehydration unit to produce a dehydrated alpha hydrogen alcohol stream, which can then be recycled back to column 40 as feed (e.g., as part of upper feed stream 46 and/or intermediate feed stream 49). A part of the bottom draw is taken out as the product stream of one or more higher alcohols and ethyl acetate 58, while the remaining part is passed through reboiler 60 to be recycled to the column 40. In an embodiment, the bottom draw may be passed through a reboiler (e.g., similar to reboiler 60) and optionally passed to a separator where the vapor portion may pass to the column 40 while at least a portion of the remainder is taken out as the product stream of the one or more higher alcohols and ethyl acetate 58. The stream passing through the reboiler 60 provides the evaporation effect and vapor flow for operating the column 40. The product stream 58 may comprise the one or more higher alcohols and ethyl acetate produced in the column along with unreacted alpha hydrogen alcohols and potentially any side products produced by the reaction.

Byproducts such as n-butyraldehyde and butan-2-one produced in the reaction may have boiling points close to the boiling points of one or more of the higher alcohols and ethyl acetate. The lower hydrogen feed stream 48 is useful in hydrogenating the by-products to produce components that can be separated from the higher alcohols. The ratio of the alpha hydrogen alcohol(s) feed to the water feed, the ratio of the alpha hydrogen alcohol(s) feed to the hydrogen feed, or a combination thereof, can beneficially be adjusted to minimize the amount of close boiling byproducts, while not excessively reducing the production of higher alcohols, ethyl acetate, or a combination thereof. In an embodiment, the molar ratio of the alpha hydrogen alcohol(s) to water ranges from about 1:10 to about 1000:1, e.g., from about 1:10 to about 1:1, from about 1:1 to about 5:1, from about 1:1 to about 10:1, from about 5:1 to about 25:1, from about 5:1 to about 50:1, from about 10:1 to about 50:1, from about 10:1 to about 100:1, from about 50:1 to about 200:1, from about 50:1 to about 400:1, from about 100:1 to about 500:1, from about 100:1 to about 1000:1, from about 200:1 to about 1000:1, or from about 500:1 to about 1000:1. In an embodiment, the molar ratio of the alpha hydrogen alcohol(s) to hydrogen ranges from about 1:10 to about 1000:1, e.g., from about 1:10 to about 1:1, from about 1:1 to about 5:1, from about 1:1 to about 10:1, from about 5:1 to about 25:1, from about 5:1 to about 50:1, from about 10:1 to about 50:1, from about 10:1 to about 100:1, from about 50:1 to about 200:1, from about 50:1 to about 400:1, from about 100:1 to about 500:1, from about 100:1 to about 1000:1, from about 200:1 to about 1000:1, or from about 500:1 to about 1000:1. In an embodiment, the column 40 may operate at any of the conditions (e.g., operating pressure, operating temperature, etc.) discussed herein with respect to column 10 in FIG. 1(b). In addition, the column 40 may have any number of stages, and in an embodiment have any number of stages as described with respect to column 10 in FIG. 1(b).

Figure 4:
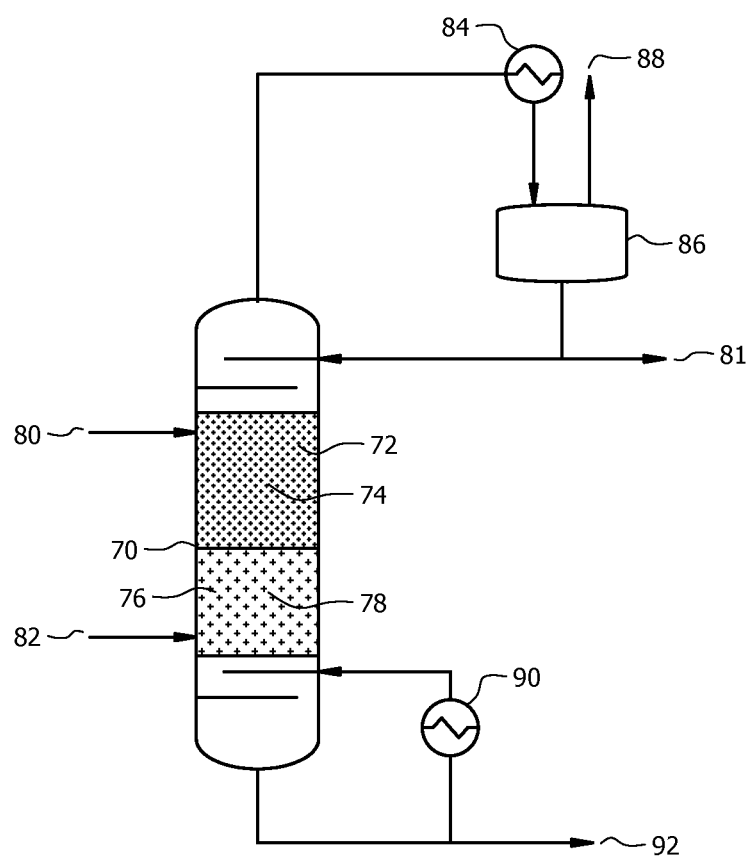
FIG. 4 shows a simplified schematic of a reactive distillation system according to yet another embodiment.

As schematically illustrated in FIG. 4, the reactive distillation column 70 has two feeds 80, 82 and uses two catalyst zones, identified as an upper zone 72 containing Catalyst A 74 and a lower catalyst zone 76 containing Catalyst B 78. Upper feed stream 80 is fed to the upper part of the column 70 (upper feed stream). The upper feed stream 80 may comprise one or more alpha hydrogen alcohols. A lower feed stream 82 is fed to the lower part of the column 70 (lower feed stream). The lower feed stream 82 may comprise hydrogen The molar ratio of the one or more alpha hydrogen alcohols to hydrogen may fall within any of the ranges described above with respect to FIG. 3(a) (e.g., from about 1:10 to about 1000:1, and all sub-ranges). The alpha hydrogen alcohol may react over the upper catalyst (Catalyst A 74) to produce one or more higher alcohols and water. Examples of suitable upper catalysts are described in more detail herein with respect to the higher alcohols conversion catalysts. As with previous schematic designs shown, the column 70 will usually include a top stage or non-reactive rectifying section 71 and a bottom stage or non-reactive stripping section 79.

Due to boiling point differences, water may move towards the top of the column 70 and the higher alcohols may move towards the bottom of the column 70. Byproducts such as acetaldehyde, n-butyraldehyde, and ethyl ether may be produced during the reaction and may move up in the column 70. At least a portion of the byproducts, if present, can be condensed in condenser 84 and recycled back to the reaction zone through reflux tank 86. Byproducts produced in the reaction may have boiling points close to the boiling point of one or more of the higher alcohols. The lower hydrogen feed stream 82 is useful in hydrogenating the by-products over the lower catalyst (Catalyst B) to produce components that can be separated easily from one or more of the higher alcohol products. Examples of hydrogenating catalysts (Catalyst B) are described in more detail herein. A product stream 81 comprising water from the reaction leaves at the top of the column 70. In an embodiment, product stream 81 may further comprise unreacted alpha hydrogen alcohol. The product stream 81 comprising the alpha hydrogen alcohol and water can be fed to a dehydration unit to produce a dehydrated alpha hydrogen alcohol stream, which can then be recycled back to column 70 as feed (e.g., as part of feed stream 80). A portion of the bottom draw is taken out as the product stream 92, while the remaining portion is passed through reboiler 90 to be recycled to the column 70. In an embodiment, the bottom draw may be passed through a reboiler (e.g., similar to reboiler 90) and optionally passed to a separator where the vapor portion may pass to the column 70 while at least a portion of the remainder is taken out as the higher alcohols product stream 92. The stream passing through the reboiler 90 provides the evaporation effect and vapor flow for operating the column 70. The product stream 92 may comprise the higher alcohols produced in the column along with unreacted alpha hydrogen alcohol(s) and potentially any byproducts produced by the reaction. Subsequent purification of product stream 92 comprising higher alcohols may be needed to remove the hydrogenated byproducts from the higher alcohols, e.g., using a separator such as that as shown in FIG. 2 as separator 32, which in an embodiment may comprise a distillation column.

In an embodiment, the column 70 may operate at any of the conditions (e.g., operating pressure, operating temperature, etc.) discussed herein with respect to column 10 in FIG. 1(b). In addition, the column 70 may have any number of stages, and in an embodiment the column 70 may have any number of stages as described with respect to column 10 in FIG. 1(b).

In the dual feed systems described above with respect to FIGS. 3(a) and 4, the hydrogen feed should be at a sufficiently low level that it does not significantly adversely affect the dehydration of the alpha hydrogen alcohol(s) in the zone above, while being effective to hydrogenate the undesirable close boiling point byproducts. Feed rates of hydrogen can be adjusted empirically to optimize this balance. Commonly, the ratio of the alpha hydrogen alcohol(s):hydrogen can be in a range of about 500:1 to 1:1 molar ratio, more commonly about 500:1 to 10:1 or 500:1 to 100:1.

In an embodiment, the system of FIG. 4 can also be used to co-produce one or more higher alcohols and ethyl acetate. In general, the process described above with respect to the production of one or more higher alcohols from a feed comprising one or more alpha hydrogen alcohols in FIG. 4 will be the same or similar when the coproduction of higher alcohols and ethyl acetate is desired. As a result, similar elements will not be described with reference to FIG. 4 in the interest of brevity. As schematically illustrated in FIG. 4, the reactive distillation column 70 comprises two feeds 80, 82 and uses two catalyst zones, identified as an upper zone 72 containing Catalyst A 74 and a lower catalyst zone 76 containing Catalyst B 78. Upper feed stream 80 is fed to the upper part of the column 70 (upper feed stream). Hydrogen feed stream 82 is fed to the lower part of the column 70 (lower feed stream). The alpha hydrogen alcohol(s) present in the upper feed stream 80 may react over the upper catalyst (Catalyst A 74) to produce one or more higher alcohols, ethyl acetate, water and hydrogen. Examples of suitable upper catalysts are described in more detail herein with respect to the conversion catalysts.

Due to boiling point differences, water and hydrogen may move toward the top of the column 70 while the higher alcohols and ethyl acetate may move toward the bottom of the column 70. Byproducts may move up in the column 70. A portion of the bottom draw is taken out as the product stream of higher alcohols and ethyl acetate 92, while the remaining portion is passed through reboiler 90 to be recycled to the column 70. In an embodiment, the bottom draw may be passed through a reboiler (e.g., similar to reboiler 90) and optionally passed to a separator where the vapor portion may pass to the column 70 while at least a portion of the remainder is taken out as the product stream of the higher alcohols and ethyl acetate 92. The product stream of the higher alcohols and ethyl acetate 92 may comprise the higher alcohols and ethyl acetate produced in the column along with unreacted alpha hydrogen alcohol(s) and potentially any side products produced by the reaction. Subsequent purification of product stream 92 comprising the higher alcohols and ethyl acetate may be needed to remove the hydrogenated byproducts from the higher alcohols and the ethyl acetate, e.g., using a separator such as that as shown in FIG. 2 as separator 32, which in an embodiment may comprise a distillation column.

In an embodiment, one or more side reactors can be connected to a reactive distillation column to increase the catalyst holdup for improved reactant conversion. In the side reactor embodiment, the side reactor feed is withdrawn from the distillation column and the reactor effluent is returned back to the same column. An adequate amount of catalyst may be arranged in a side reactor system where traditional reactor types and catalyst structures can be used. Also, the reaction conditions within the side reactor such as temperature can be adjusted independently of those prevailing in the distillation column by appropriate heat exchange. Further, the flow rates of the side reactors can be selectively controlled to provide a desired space velocity through the side reactor.

Figure 5A:
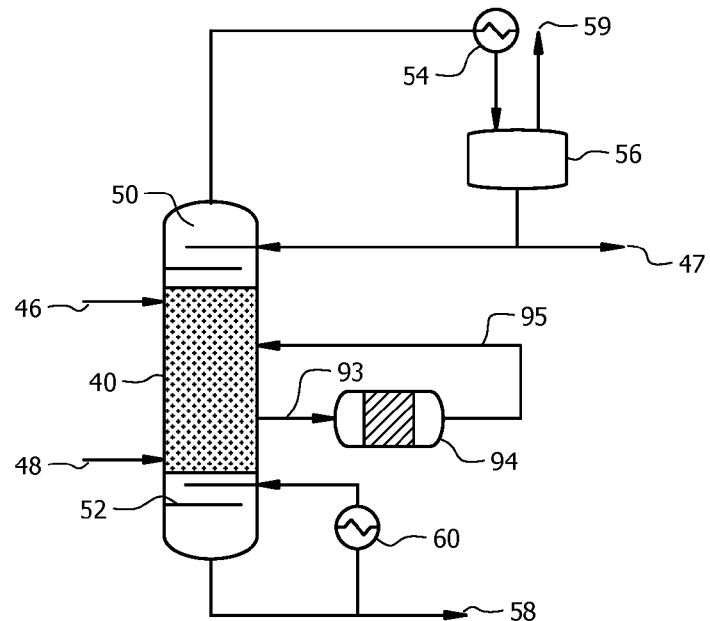
FIGS. 5(a) and 5(b) shows a simplified schematic of a reactive distillation system according to an embodiment.
Figure 5B:
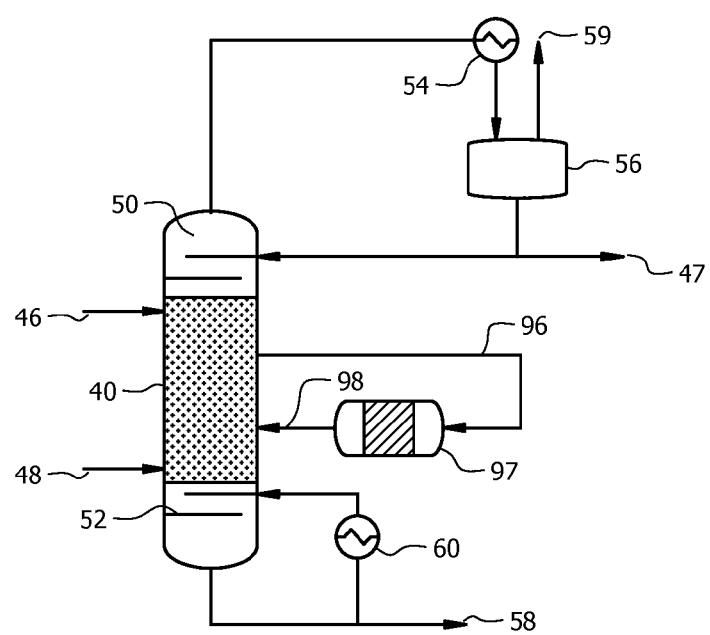

Schematics for a side reactor reactive distillation column with a single higher alcohol(s) conversion catalyst are shown in FIG. 5. A single side reactor is shown, however, multiple side reactors along the length of the reactive distillation column can be used. FIG. 5(a) shows a configuration where the feed stream 93 to the side reactor 94 is bottom up and vapor phase. In an embodiment, the alpha hydrogen alcohol(s) may react over the catalyst within the side reactor 94 in the vapor phase. The outlet from side reactor 94 is stream 95 which is sent back to the distillation column 40 at any location in the column 40 above the location of feed stream 93. FIG. 5(b) shows a configuration where the feed stream 96 to the side reactor 97 is top down and liquid phase. In an embodiment, the alpha hydrogen alcohol(s) may react over the catalyst within the side reactor 97 in the liquid phase. The outlet from side reactor 97 is stream 98 which is sent back to the distillation column 40 at any location in the column 40 below the location of feed stream 96. The side reactors 94 and 97 each contain one or more higher alcohols conversion catalyst for converting the alpha hydrogen alcohol(s) into one or more higher alcohols. Examples of suitable higher alcohols conversion catalysts are described in more detail herein. In some embodiments, only one or more of the side reactors may comprise a catalyst, and there may not be a catalyst located within the reactive distillation column 40.

The use of a side reactor using a liquid feed may allow for the reaction to occur in the liquid phase. While not intending to be limited by theory, it is believed that the dehydration of an alpha hydrogen alcohol (e.g., ethanol) to produce a higher alcohol (e.g., butanol) may occur over the higher alcohols conversion catalysts described herein in the liquid phase. The use of a liquid phase reaction may allow for reactive distillation to be effectively used for converting the alpha hydrogen alcohol into one or more higher alcohols and water.

While illustrated as a bottom up vapor phase design and a top down liquid phase design in FIGS. 5(a) and 5(b), the side reactors 94, 97 may also operate bottom up using a liquid phase draw from the column 40 and top down using a vapor phase draw from the column with the appropriate equipment such as pumps, compressors, valves, piping, etc. In an embodiment, the side reactors 94, 97 may be implemented as a single reactor vessel, or as a plurality of reactor vessels arranged in series and/or parallel. In an embodiment, a plurality of side reactors may be implemented as shown in FIGS. 5(a) and 5(b) along the length of the column as needed. In addition, when both the column 40 and the side reactor 94 comprise catalysts, the higher alcohol conversion catalyst in both the column 40 and the side reactor 94 may convert the alpha hydrogen alcohol(s) into one or more higher alcohols, though the specific higher alcohol conversion catalysts (e.g., catalyst compositions, catalyst forms, catalyst component loadings, or any combination thereof) in each of the column 40 and the side reactor 94, 97 may be the same or different. Suitable higher alcohol conversion catalysts for converting the alpha hydrogen alcohol(s) into the higher alcohols may be selected based on the expected operating conditions, which may vary between the column 40 and the side reactor 94, 97. In some embodiments, the product selection can be tuned through the use of the catalyst selection in the column 40 and the side reactor 94, 97. For example, the higher alcohol conversion catalyst in the column 40 may be configured to produce one or more isomers of butanol, and the higher alcohol conversion catalyst in the side reactor 94, 97 may be configured to produce an alcohol having a molecular weight heavier than butanol. By controlling the flow of the fluids within the column, the product distribution can be tuned to produce more or less butanol, or correspondingly, more or less of the heavier molecular weight alcohols.

In an embodiment, each of the systems of FIGS. 5(a) and 5(b) can be used to co-produce a higher alcohol and/or ethyl acetate by including the conversion catalysts described herein. In general, the process described above with respect to the production of one or more higher alcohols from a feed comprising one or more alpha hydrogen alcohols in FIG. 5 will be the same or similar when the coproduction of higher alcohols and ethyl acetate is desired. As a result, similar elements will not be described with reference to FIG. 5 in the interest of brevity. In general, the production system may be the same as the system for producing higher alcohols from the alpha hydrogen alcohol feed, except that the catalyst may be used to co-produce one or more higher alcohols and ethyl acetate from the alpha hydrogen alcohol feed. In an embodiment, the side reactors 94 and 97 may contain conversion catalyst for converting the alpha hydrogen alcohol in the feed into one or more higher alcohols and/or ethyl acetate. Examples of suitable conversion catalysts are described in more detail herein. In some embodiments, the side reactors 94, 97 may comprise a plurality of catalysts to produce one or more higher alcohols and ethyl acetate. For example, the side reactors 94, 97 may comprise a higher alcohols conversion catalysts and an ethyl acetate conversion catalyst. In some embodiments, the catalyst in the column 40 or the side reactors 94, 97 may be the same or different. In some embodiments, only one or more of the side reactors may comprise a catalyst, and there may not be a catalyst located within the reactive distillation column. Suitable conversion catalysts for converting ethanol into butanol and ethyl acetate may be selected based on the expected operating conditions, which may vary between the column 40 and the side reactor 94, 97.

Figure 6A:
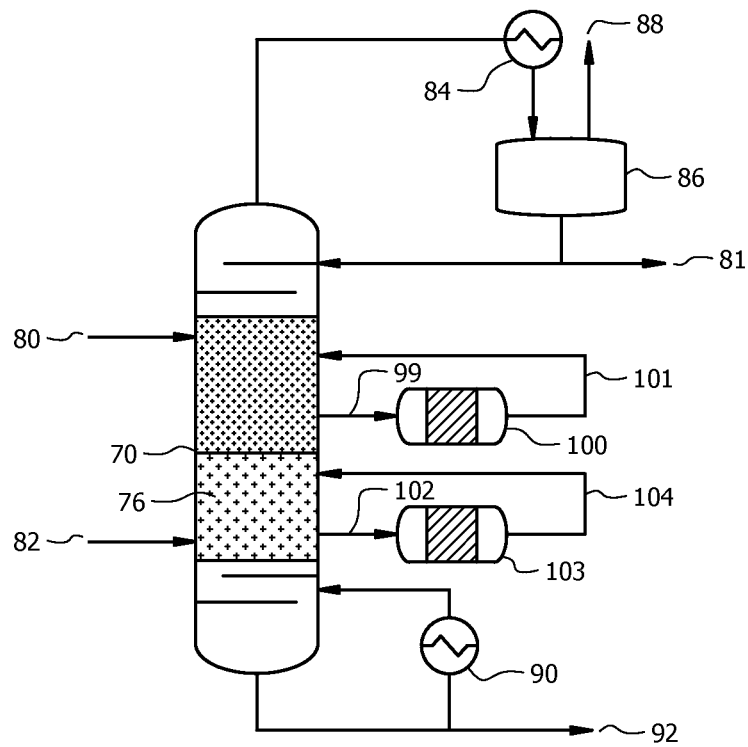
FIGS. 6(a) and 6(b) shows a simplified schematic of a reactive distillation system according to another embodiment.

Schematics for a side reactor reactive distillation with two feeds and using two catalyst zones are shown in FIG. 6. In this embodiment, an upper feed 80 of the alpha hydrogen alcohol(s) may be fed to the upper catalyst zone, and a lower feed 82 of hydrogen may be fed to the lower catalyst zone. A single side reactor is shown for each catalyst zone in the reactive distillation column 70, however, multiple side reactors along the length of the reactive distillation column 70 can be used for each catalyst zone. FIG. 6(a) shows a configuration where the top zone feed stream 99 to the side reactor 100 is bottom up and vapor phase. The bottom zone feed stream 102 to another side reactor 103 is also bottom up and vapor phase. The outlet from side reactor 100 is stream 101 which is sent back to the distillation column at any location in the column above the location of feed stream 99. The outlet from side reactor 103 is stream 104 which is sent back to the distillation column at any location in the column above the location of feed stream 102.

Figure 6B:
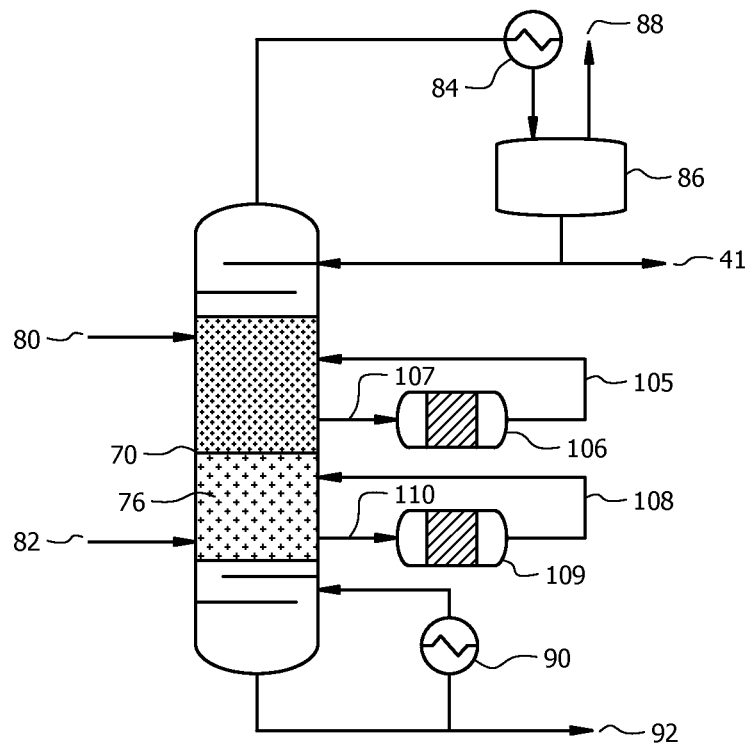

FIG. 6(b) shows a configuration where the top zone feed stream 105 to the side reactor 106 is top down and liquid phase. The bottom zone feed stream 108 to another side reactor 109 is also top down and liquid phase. The outlet from side reactor 106 is stream 107 which is sent back to the distillation column at any location in the column below the location of feed stream 105. The outlet from side reactor 109 is stream 110 which is sent back to the distillation column at any location in the column below the location of feed stream 108. Examples of suitable catalysts for side reactors 100 and 106 may include any of the higher alcohol conversion catalysts described in more detail herein. Examples of hydrogenating catalysts for side reactors 103 and 109 include any of the hydrogenating catalysts described in more detail herein. In some embodiments, only one or more of the side reactors may comprise a catalyst, and there may not be a catalyst located within the reactive distillation column.

While illustrated as a bottom up vapor phase design and a top down liquid phase design in FIGS. 6(a) and 6(b), the side reactors 100, 103, 106, 109 may also operate bottom up using a liquid phase draw from the column 70 and top down using a vapor phase draw from the column 70 with the appropriate equipment such as pumps, compressors, valves, piping, etc. In an embodiment, the side reactors 100, 103, 106, 109 may be implemented as a single reactor vessel, or as a plurality of reactor vessels arranged in series and/or parallel. In an embodiment, a plurality of side reactors may be implemented as shown in FIGS. 6(a) and 6(b) along the length of the column as needed. In addition, the respective higher alcohols conversion catalysts in both the column 70 and the side reactors 100, 106 may convert a feed comprising the alpha hydrogen alcohol into one or more higher alcohols, though the specific higher alcohols conversion catalysts (e.g., catalyst compositions, catalyst forms, catalyst component loadings, or any combination thereof) in each of the column 40 and the side reactors 100, 106 may be the same or different. A suitable higher alcohols conversion catalyst for converting the alpha hydrogen alcohol into the higher alcohols may be selected based on the expected operating conditions, which may vary between the column 40 and the side reactors 100, 106. Similarly, the respective catalysts in both the column 70 and the side reactors 103, 109 may comprise hydrogenating catalysts, though the specific catalysts (e.g., catalyst compositions, catalyst forms, catalyst component loadings, or any combination thereof) in each of the column 70 and the side reactors 103, 109 may be the same or different. Suitable hydrogenating catalysts may be selected based on the expected operating conditions, which may vary between the column 70 and the side reactors 100, 106.

In an embodiment, each of the systems of FIGS. 6(a) and 6(b) can be used to co-produce one or more higher alcohols and/or ethyl acetate by including a conversion catalysts described herein. Schematics for a side reactor reactive distillation with two feeds and using two distinct catalyst zones are shown in FIG. 6. In general, the process described above with respect to the production of one or more higher alcohols from a feed comprising one or more alpha hydrogen alcohols in FIG. 6 will be the same or similar when the coproduction of higher alcohols and ethyl acetate is desired. As a result, similar elements will not be described with reference to FIG. 6 in the interest of brevity. In general, the system may be the same as the system for producing higher alcohols from the alpha hydrogen alcohol feed, except that the catalyst may be used to produce one or more higher alcohols and/or ethyl acetate from the alpha hydrogen alcohol feed. Examples of suitable catalysts for side reactors 100 and 106 may include any of the conversion catalysts described in more detail herein. Examples of hydrogenating catalysts for side reactors 103 and 109 include any of the hydrogenating catalysts described in more detail herein. In some embodiments, only one or more of the side reactors may comprise a catalyst, and there may not be a catalyst located within the reactive distillation column.

In the reactive distillation systems of FIGS. 5(a), 5(b), 6(a), and 6(b), the composition of product stream 58, 92 may be adjusted by controlling the flow rate between the reactive distillation column 40, 70 and the side reactors 94, 97, 100, 103, 106, 109. In an embodiment, a system for the production of higher alcohols and/or ethyl acetate comprises a reactive distillation column 40, 70 charged with one or more higher alcohol conversion catalysts and one or more side reactors 94, 97, 100, 106 charged with one or more conversion catalysts. During continuous operation, flow rates 93/95, 96/98, 99/101, 105/107 between the column 40, 70 and the one or more side reactors 94, 97, 100, 106 may be adjusted to achieve a desired composition of the product stream 58, 92. The flow rates 93/95, 96/98, 99/101, 105/107 between the column 40, 70 and the one or more side reactors 94, 97, 100, 106 may be increased to decrease the production of one or more higher alcohols relative to ethyl acetate (e.g., the ratio of higher alcohols to ethyl acetate), or decreased to increase the production of the higher alcohols relative to ethyl acetate. Alternatively, the flow between the column 40, 70 and the one or more side reactors 94, 97, 100, 106 may be cut off to produce a product stream 58, 92 of pure or substantially pure higher alcohols. In an embodiment, adjustments to the flow rates 3/95, 96/98, 99/101, 105/107 are made by a control system.

In another embodiment, a system for the production of one or more higher alcohols (e.g., butanol) and/or ethyl acetate comprises a reactive distillation column 40, 70 charged with one or more conversion catalysts and one or more side reactors 94, 97, 100, 106 are charged with one or more conversion catalysts. During continuous operation, flow rates 3/95, 96/98, 99/101, 105/107 between the column 40, 70 and the one or more side reactors 94, 97, 100, 106 may be adjusted to achieve a desired composition of the product stream 58, 92. The flow rates 3/95, 96/98, 99/101, 105/107 between the column 40, 70 and the one or more side reactors 94, 97, 100, 106 may be increased to increase the production of a higher alcohol relative to ethyl acetate or decreased to decrease the production of higher alcohol relative to ethyl acetate. When the flow rates 3/95, 96/98, 99/101, 105/107 between the column 40, 70 and the one or more side reactors 94, 97, 100, 106 are cut off the production of ethyl acetate relative to the production of one or more of the higher alcohols is maximized. In an embodiment, adjustments to the flow rates 3/95, 96/98, 99/101, 105/107 may be made by a control system.

In an embodiment, a system for the production of one or more higher alcohols may comprise a reactive distillation column 40, 70 charged with a higher alcohol conversion catalyst suitable for use with a feed of pure or substantially pure alpha hydrogen alcohol and one or more side reactors 94, 97, 100, 106 charged with a higher alcohol conversion catalyst suitable for use with a feed of one or more alpha hydrogen alcohol and water. Alternatively, the reactive distillation column 40, 70 may be charged with a higher alcohol conversion catalyst suitable for use with a feed of the alpha hydrogen alcohol(s) and water and one or more side reactors 94, 97, 100, 106 may be charged with a higher alcohol conversion catalyst suitable for use with pure or substantially pure alpha hydrogen alcohol. If the feed is pure or substantially pure alpha hydrogen alcohol, the flow rates 3/95, 96/98, 99/101, 105/107 between the column 40, 70 and the side reactors 94, 97, 100, 106 may be adjusted to maximize the higher alcohol(s) production by increasing flow through the reactor(s) having the catalyst suitable for use with pure or substantially pure alpha hydrogen alcohol(s), decreasing the flow through the reactor having the catalyst suitable for use with the alpha hydrogen alcohol(s) and water, or a combination thereof. If the feed comprises the alpha hydrogen alcohol(s) and water, the flow rates 3/95, 96/98, 99/101, 105/107 between the column 40, 70 and the side reactors 94, 97, 100, 106 may be adjusted to maximize the higher alcohol(s) production by increasing flow through the column or reactor(s) having the catalyst suitable for use with the alpha hydrogen alcohol(s) and water, decreasing the flow through the column or reactor(s) having the catalyst suitable for use with pure or substantially pure alpha hydrogen alcohol(s), or a combination thereof. In an embodiment, adjustments to the flow rates 3/95, 96/98, 99/101, 105/107 can be made by a control system. In an embodiment, the flow rates 102/104, 108/110 may be increased or decreased to reduce or eliminate one or more undesirable byproducts from the product stream 58, 92. In an embodiment, adjustments to the flow rates 102/104, 108/110 are made by a control system.

As a general proposition, the number of side reactors and the type of catalyst with which the column and each side reactor are individually charged can be selected to accommodate a desired variety of feedstocks, a desired range of product compositions, or a combination thereof during operation of the reactive distillation column. During continuous operation, the flow rates between the side reactors and the column can be adjusted (e.g., selectively tuned) to respond to changes in feedstock, to achieve a desired product composition, or a combination thereof. The ability to adjust the flow rates between the side reactors and the column advantageously allows feedstocks to be changed when market fluctuations in price and availability favor the use of a feedstock having a different composition (e.g. lower quality, higher water content, different mix of alpha hydrogen alcohols, etc.). The ability to adjust the flow rates between the side reactors and the column advantageously allows feed quality to be maintained despite fluctuations in feedstock composition during continuous operation. The ability to adjust and/or control the flow rates between the side reactors and the column may also allow for the reduction or elimination of undesirable byproducts to advantageously increase the purity of the desired products.

Figure 7A:
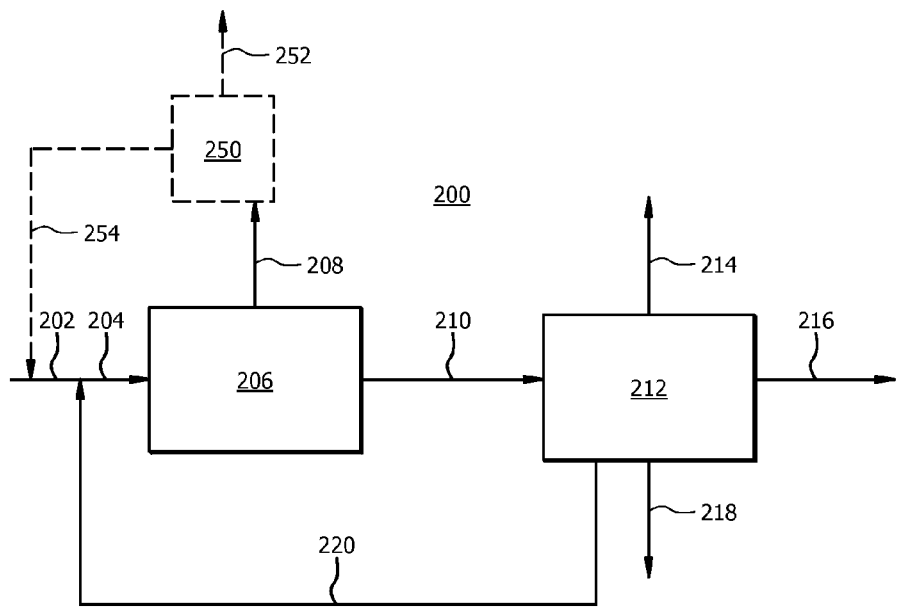
FIGS. 7(a) and 7(b) illustrates a schematic flow diagram of a reactive distillation system with a recycle according to an embodiment.

As schematically illustrated in FIG. 7(a), a higher alcohols production process may comprise a products separation section 212 for use in separating the product stream and allowing at least a portion of any unreacted ethanol to be recycled to the inlet of the process. The products separation section may be configured to provide at least one product stream comprising a single reaction product such as a higher alcohol (e.g., propanol, butanol, hexanol, etc.), ethyl acetate, butyl acetate, or another reaction product having a purity of greater than about 90%, greater than about 95%, greater than about 96%, greater than about 97%, greater than about 98%, greater than about 99%, or greater than about 99.5% by weight. In an embodiment, a separation train may be used to produce a plurality of streams that each predominately comprise a single reaction product such as a higher alcohol (e.g., propanol, butanol, hexanol, etc.), ethyl acetate, butyl acetate, or another reaction product having a purity of greater than about 90%, greater than about 95%, greater than about 96%, greater than about 97%, greater than about 98%, greater than about 99%, or greater than about 99.5% by weight. At least one additional stream may be produced comprising the remaining components of the product stream from the reactive distillation column. In an embodiment, a plurality of streams are produced in the separation section comprising a stream predominantly comprising butanol, a stream predominantly comprising propanol, a stream predominantly comprising hexanol, a stream predominantly comprising ethyl acetate, a stream comprising water, a stream comprising ethanol, a heavies stream comprising one or more reaction products with boiling points above the boiling point of hexanol, or any combination thereof. In an embodiment, a stream comprising ethanol, if present, may be recycled to the reactive distillation column. In an embodiment, at least a portion of the stream comprising water may be recycled to the reactive distillation column to provide at least a portion of the water feed.

As schematically illustrated in FIG. 7(a), a system 200 for producing one or more higher alcohols may comprise a feed stream 202 comprising an alpha hydrogen alcohol that may be optionally combined with a recycle stream 220 comprising an alpha hydrogen alcohol to form the inlet stream 204 to the reactive distillation system 206. The system 200 may be useful for embodiments in which there is an incomplete conversion of an alpha hydrogen alcohol in the reactive distillation system 206. While illustrated as being combined prior to introduction to the reactive distillation system 206, the feed stream 202 and the recycle stream 220 may be fed individually to the reactive distillation system 206. In an embodiment, the reactive distillation system 206 may comprise any of the reactive distillation systems described with respect to FIGS. 1-6 herein. The reactive distillation system 206 may produce an overhead product stream 208 and a bottoms product stream 210. The overhead product stream 208 may comprise water, hydrogen, unreacted alpha hydrogen alcohol(s), or a combination thereof and may generally correspond to any of the streams 11, 47, and/or 81 as illustrated in FIGS. 1-6. Similarly, the bottoms product stream 210 may comprise higher alcohols (e.g., butanol, 1-hexanol, 1-octanol, 2-ethyl-1-butanol, 2-ethyl-1-hexanol, butanediol, etc.), ethyl acetate, butyl acetate, ethyl butyrate, 2-pentanone, propanol, additional reaction products, possibly water, and/or any combination thereof. In an embodiment, the bottoms product stream 210 may correspond to any of the streams 22, 36, 58, and/or 92 as illustrated in FIGS. 1-6.

An optional overhead separation section 250 may receive the overhead product stream 208 from the reactive distillation system 206. The overhead separation section 250 may be configured to separate water from any alpha hydrogen alcohol(s) (e.g., ethanol) in the overhead product stream 208, which may be present at a water-alcohol azeotrope such as a water-ethanol azeotrope, to allow the feed alpha hydrogen alcohol to be recycled to the system while removing the water to drive the reaction within the reactive distillation system 206. The overhead separation section 250 may comprise any number or type of separation units, which may employ pressure- and/or temperature-swing distillation, pressure- and/or temperature-swing adsorption, membrane-based separation, molecular sieve separation, any other suitable separation technology, or any combination thereof, all of which may be used to remove a desired amount of water from the overhead product stream 208. The overhead separation section 250 may produce a recycle stream 254 comprising one or more alpha hydrogen alcohols and an outlet stream 252 comprising water. The recycle stream 254 may comprise the alpha hydrogen alcohol(s) for use as a feed for the reactive distillation system 206. In some embodiments, the alpha hydrogen alcohol stream 254 may not be recycled to the reactive distillation system, but rather may exit the system 200 as a separate product stream. While illustrated as being combined prior to introduction to the reactive distillation system 206, the feed stream 202 and the recycle stream 254 (as well as recycle stream 220) may be fed individually to the reactive distillation system 206.

A products separation section 212 may receive the bottoms product stream 210 from the reactive distillation system 206, and, in some embodiments, the overhead product stream 208. The products separation section 212 may comprise any number or type of separation units, which may employ pressure- and/or temperature-swing distillation, pressure- and/or temperature-swing adsorption, membrane-based separation, cryogenic distillation, any other suitable separation technology, or any combination thereof, all of which may be used to generate a desired product distribution. The products separation section 212 may generally produce one or more product streams such as product stream 216. The higher alcohol product stream 216 may comprise a higher alcohol having a purity of greater than about 90%, greater than about 95%, greater than about 96%, greater than about 97%, greater than about 98%, greater than about 99%, or greater than about 99.5% by weight. In addition to the higher alcohol product stream 216, one or more additional streams may be produced by the products separation section 212. In an embodiment, a lights product stream 214 may be produced. The lights product stream 214 may comprise water, any alpha hydrogen alcohol from the feed, ethyl acetate, other light components, or any combination thereof. In an embodiment, a heavies product stream 218 may comprise one or more reaction products (e.g., one or more aldehydes, ketones, heavy alcohols, any combination thereof, etc.). In an embodiment, a recycle stream 220 may be produced. The recycle stream may comprise one or more alpha hydrogen alcohols for use as a feed for the reactive distillation system 206. In some embodiments, the alpha hydrogen alcohol(s) stream may not be recycled to the reactive distillation system, but rather may exit the system 200 as a separate product stream. Each of the potential product streams 214, 216, 218, and/or 220 may exit the system as separate product stream and/or exit the system 200 for use as fuel and/or as a feed to additional downstream processes. While illustrated as separate streams 214, 216, 218, and/or 220, one or more of these streams may exit the system 200 as a combined product stream.

Figure 7B:
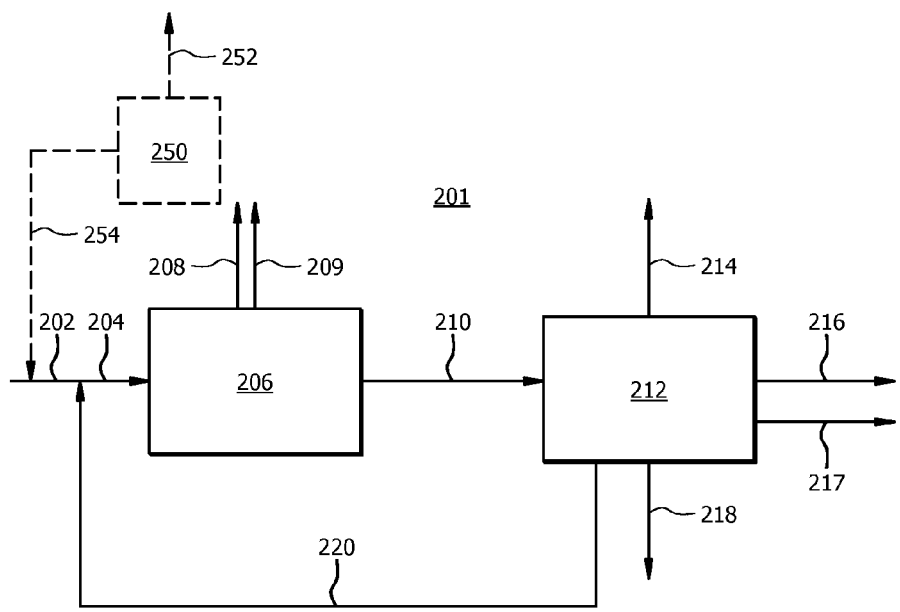

As schematically illustrated in FIG. 7(b), a higher alcohol(s) and ethyl acetate production process may comprise a products separation section for use in separating the product stream and allowing at a least a portion of any unreacted alpha hydrogen alcohol(s) in the feed to be recycled to the inlet of the process. The products separation section may be configured to provide at least one product stream comprising a higher alcohol and at least one product stream comprising ethyl acetate. The product stream comprising the higher alcohol can have a purity of greater than about 90%, greater than about 95%, greater than about 96%, greater than about 97%, greater than about 98%, greater than about 99%, or greater than about 99.5% by weight. The product stream comprising ethyl acetate can have a purity of greater than about 90%, greater than about 95%, greater than about 96%, greater than about 97%, greater than about 98%, greater than about 99%, or greater than about 99.5% ethyl acetate by weight. At least one additional stream may be produced comprising the remaining components of the product stream from the reactive distillation column. In an embodiment, a plurality of streams are produced in the separation section comprising one or more streams predominantly comprising individual higher alcohol(s), a stream predominantly comprising ethyl acetate, a stream comprising water, a stream comprising hydrogen, a stream comprising one or more alpha hydrogen alcohols, a heavies stream comprising one or more reaction products with boiling points above the boiling points of the separated higher alcohol(s) and/or ethyl acetate, or any combination thereof. In an embodiment, the stream comprising the alpha hydrogen alcohol(s) may be recycled to the reactive distillation column. In an embodiment, at least a portion of the stream comprising water may be recycled to the reactive distillation column to provide at least a portion of a water feed. In an embodiment, at least a portion of the stream comprising hydrogen may be recycled to the reactive distillation column to provide at least a portion of the hydrogen feed.

As schematically illustrated in FIG. 7(b), a system 201 for producing higher alcohol(s) and ethyl acetate may comprise a feed stream 202 comprising one or more alpha hydrogen alcohols that may be combined with a recycle stream 220 comprising at least one alpha hydrogen alcohol to form the inlet stream 204 to the reactive distillation system 206. The system 201 may be useful for embodiments in which there is an incomplete conversion of the alpha hydrogen alcohol(s) in the reactive distillation system 206. While illustrated as being combined prior to introduction to the reactive distillation system 206, the feed stream 202 and the recycle stream 220 may be fed individually to the reactive distillation system 206. In an embodiment, the reactive distillation system 206 may comprise any of the reactive distillation systems described with respect to FIGS. 1-6 herein. The reactive distillation system may produce overhead product streams 208 and 209 and a bottoms product stream 210. The overhead product stream 208 may comprise water, hydrogen, and at least a portion of any unreacted alpha hydrogen alcohol(s), and may generally correspond to any of the streams 11, 47, and/or 81 as illustrated in FIGS. 1-6. The overhead product stream 209 may comprise hydrogen and may generally correspond to any of the streams 19, 59, and/or 88 as illustrated in FIGS. 1-6. The bottoms product stream 210 may comprise the higher alcohol(s), ethyl acetate, additional reaction products, or any combination thereof, and the bottoms product stream 210 may generally correspond to any of the streams 22, 36, 58, and/or 92 as illustrated in FIGS. 1-6.

An optional overhead separation section 250 may receive the overhead product stream 208 from the reactive distillation system 206. The overhead separation section 250 may be configured to separate water from any alpha hydrogen alcohol(s) in the overhead product stream 208, which may be present at a water-alcohol azeotrope, to allow any alpha hydrogen alcohol(s) to be recycled to the system while removing the water to drive the reaction within the reactive distillation system 206. The overhead separation section 250 may comprise any number or type of separation units, which may employ pressure- and/or temperature-swing distillation, pressure- and/or temperature-swing adsorption, membrane-based separation, molecular sieve separation, any other suitable separation technology, or any combination thereof, all of which may be used to remove a desired amount of water from the overhead product stream 208. The overhead separation section 250 may produce a recycle stream 254 comprising any alpha hydrogen alcohol(s) and an outlet stream 252 comprising water. The recycle stream 254 may comprise an alpha hydrogen alcohol for use as a feed for the reactive distillation system 206. In some embodiments, the alpha hydrogen alcohol stream 254 may not be recycled to the reactive distillation system, but rather may exit the system 200 as a separate product stream. While illustrated as being combined prior to introduction to the reactive distillation system 206, the feed stream 202 and the recycle stream 254 (as well as recycle stream 220) may be fed individually to the reactive distillation system 206.

A products separation section 212 may receive the bottoms product stream 210 from the reactive distillation system 206, and, in some embodiments, the overhead product stream 208. The products separation section 212 may comprise any number or type of separation units, which may employ pressure- and/or temperature-swing distillation, pressure- and/or temperature-swing adsorption, membrane-based separation, cryogenic distillation, any other suitable separation technology, or any combination thereof, all of which may be used to generate a desired product distribution. The products separation section 212 may generally produce one or more higher alcohol product streams 216, an ethyl acetate product stream 217, or a combination thereof. The one or more higher alcohol product streams 216 may each comprise an individual higher alcohol having a purity of greater than about 90%, greater than about 95%, greater than about 96%, greater than about 97%, greater than about 98%, greater than about 99%, or greater than about 99.5% by weight. The ethyl acetate product stream 216 may comprise ethyl acetate having a purity of greater than about 90%, greater than about 95%, greater than about 96%, greater than about 97%, greater than about 98%, greater than about 99%, or greater than about 99.5% ethyl acetate by weight. In addition to the one or more higher alcohol product streams 216 and the ethyl acetate product stream 217, one or more additional streams may be produced by the products separation section 212. In an embodiment, a lights product stream 214 may be produced. The lights product stream 214 may comprise water, hydrogen, an alpha hydrogen alcohol, other light components, or any combination thereof. In an embodiment, a heavies product stream 218 may comprise one or more reaction products (e.g., one or more aldehydes, ketones, other alcohols, any combination thereof, etc.). In an embodiment, a recycle stream 220 may be produced. The recycle stream may comprise an alpha hydrogen alcohol for use as a feed for the reactive distillation system 206. In some embodiments, the alpha hydrogen alcohol stream may not be recycled to the reactive distillation system, but rather may exit the system 200 as a separate product stream. Each of the potential product streams 214, 216, 217, 218, and/or 220 may exit the system as separate product stream and/or exit the system 200 for use as fuel and/or as a feed to additional downstream processes. While illustrated as separate streams 214, 216, 217, 218, and/or 220, one or more of these streams may exit the system 220 as a combined product stream.

The higher alcohols production process, with or without the production of ethyl acetate, may produce a variety of products. For example, the process may produce one or more higher alcohols such as butanol, propanol, 1-hexanol, 1-octanol, 2-ethyl-1-butanol, 2-ethyl-1-hexanol, butanediol, and heavier alcohols. The process may also produce various additional products such as ethyl acetate, butyl acetate, ethyl butyrate, 2-pentanone, propanol, and/or water. Various side products may also be produced that can result in a complex mixture of components that can be difficult to separate. This complex mixture may exhibit a number of binary azeotropes, ternary azeotropes, and possibly azeotropes containing four or more components. Some of the azeotropes can be homogeneous, while others can be heterogeneous. These azeotropes can give rise to distillation boundaries in the composition space that, along with the azeotropes, act as barriers for distillation and limit the ability to achieve high recovery and/or purity of the desired products using distillation alone. When water is present in a sufficient amount, the system may also comprise a multiple liquid phase region, with vapor-liquid-liquid and/or liquid-liquid equilibrium tie-lines that cross some of these boundaries. In some embodiments, a product separation system can exploit this characteristic of the system and comprise a separation sequence comprising distillation columns and decanters. This system may be capable of producing one or more high purity product streams such as one or more high purity higher alcohol stream, an ethyl acetate stream, and potentially one or more other valuable byproduct streams.

Figure 8:
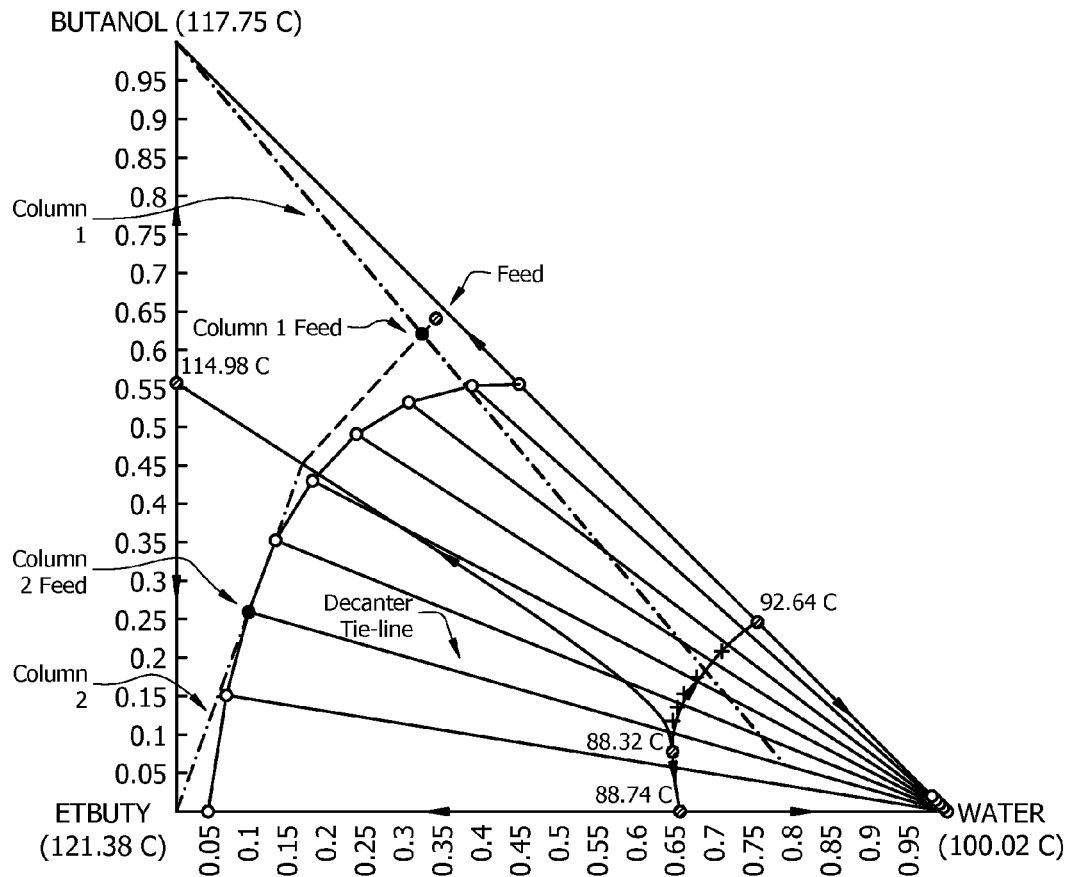
FIG. 8 illustrates a residue curve map for a mixture of butanol, ethyl butyrate, and water.

In an embodiment, a separation process may be designed to separate ethyl butyrate, a valuable reaction byproduct, from a mixture of a higher alcohol such as butanol and water. The residue curve map for the mixture is illustrated in FIG. 8, and shows that such as a system exhibits three minimum boiling binary azeotropes, of which two (water-butanol and water-ethyl butyrate) are heterogeneous, while the third binary azeotrope (butanol-ethyl butyrate) is homogeneous. The system also exhibits a ternary minimum boiling heterogeneous azeotrope. These azeotropes give rise to three distillation boundaries, which divide the composition space into three distinct regions. The system also exhibits a heterogeneous region, and some of the liquid-liquid equilibrium tie-lines cross one or more of the distillation boundaries. In this embodiment, the feed to the separation system may predominantly comprise butanol, and the feed therefore lies in the upper distillation region as shown in FIG. 8. While distillation could be used recover high purity butanol from this mixture, the presence of the distillation boundaries restricts the overall recovery of butanol, as well as ability to recover high purity ethyl butyrate.

Figure 9:
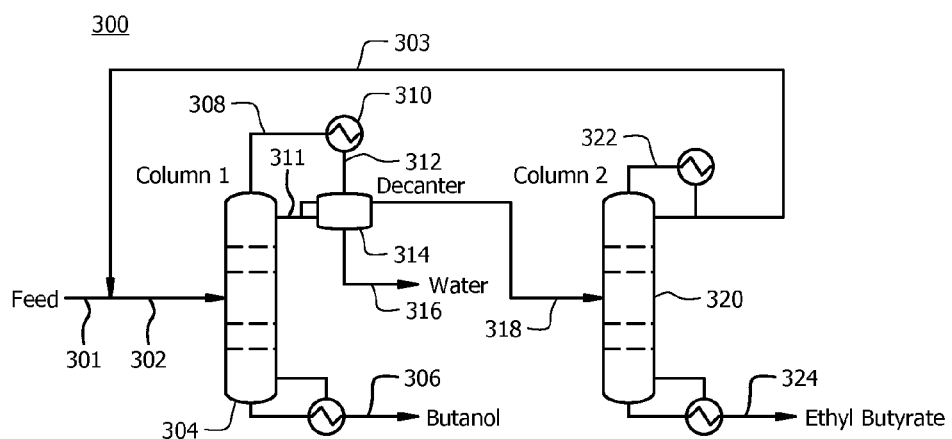
FIG. 9 illustrates a schematic flow diagram of a product separation system according to an embodiment.

Various separation schemes can then be used to separate a complex mixture such as the product stream from the reactive distillation process described herein. An embodiment of a separation sequence for recovering high purity butanol, high purity ethyl butyrate, and water containing only small amounts of the organic components is schematically illustrated in FIG. 9. An inlet stream 301 comprising butanol, ethyl butyrate, and water may be combined with a recycle stream 303 to form the combined stream 302. In this embodiment, ethyl butyrate is included a representative species of other esters (e.g., ethyl esters, butyl esters, etc.) in terms of the vapor-liquid behavior, and additional esters (e.g., butyl acetate, ethyl acetate, etc.) may also be present in the system and can be expected to behave similarly. The presence of water in the inlet stream 301 may aid in the separation of the butanol from the ethyl butyrate, and water can be added to the inlet if a sufficient amount of water is not present. The combined inlet stream 302 can be fed to a first distillation column 304. The distillation column 304 may comprise any of the types of distillation columns described herein. The distillation column 304 may operate at a pressure ranging from about 0.1 atm to about 80 atm, or about 0.5 atm to about 40 atm. The distillation column 304 may produce an overhead stream 308 and a bottoms stream 306. The bottoms stream 306 may comprise high purity butanol. For example, the butanol recovered in the bottoms stream may have a purity of greater than about 90%, greater than about 95%, greater than about 96%, greater than about 97%, greater than about 98%, greater than about 99%, or greater than about 99.5% butanol by weight. While described as butanol, other higher alcohols, if present, may also be recovered in the bottoms stream 306.

The overhead stream 308 from the first distillation column 304 may pass through a heat exchanger 310 to at least partially condense the overhead stream 308 and pass the condensed stream 312 to a decanter 314. Heat exchanger 310 may comprise any of the heat exchanger types described herein. The decanter 314 generally comprises any device capable of provided a liquid-liquid separation. Decanters can utilize devices such as weirs, downspouts, settling chambers, internal heat exchangers, and the like to effect the liquid-liquid separation. In some embodiments, a decanter may also provide an outlet vapor stream or the vapor, if present, may leave with one of the liquid streams. In this embodiment, the decanter 314 may provide a separation of a liquid phase predominately comprising water from an organic phase comprising the ethyl butyrate. A fraction of the organic phase and possibly a fraction of the aqueous phase can be refluxed to the column from the decanter 314 as reflux stream 311. The remainder of the aqueous phase, which may comprise water and a relatively minor amount of dissolved organics, can be recovered and discharged from the system as water stream 316. The portion of the organic phase not refluxed to the distillation column 304 may be passed to a second distillation column 320. The second distillation column 320 may comprise any of the types of distillation columns described herein, and the second distillation column 320 may operate at a pressure ranging from about 0.1 atm to about 80 atm, or about 0.5 atm to about 40 atm. The second distillation column 320 may produce an overhead stream 322 and a bottoms stream 324. A portion of the bottoms stream 324 may pass through an exchanger to provide a vapor feed to the column, and the remaining portion may comprise high purity ethyl butyrate. For example, the ethyl butyrate recovered in the bottoms stream 324 may have a purity of greater than about 90%, greater than about 95%, greater than about 96%, greater than about 97%, greater than about 98%, greater than about 99%, or greater than about 99.5% ethyl butyrate by weight. The overhead stream 322 may comprise water and butanol. A portion of the overhead stream 322 can be condensed and refluxed to the second distillation column 320, and the remaining portion can be recycled as recycle stream 303 to join the inlet stream 301 and/or pass into the first distillation column 304. The resulting material balance lines for this separation sequence are shown in FIG. 8.

Figure 10:
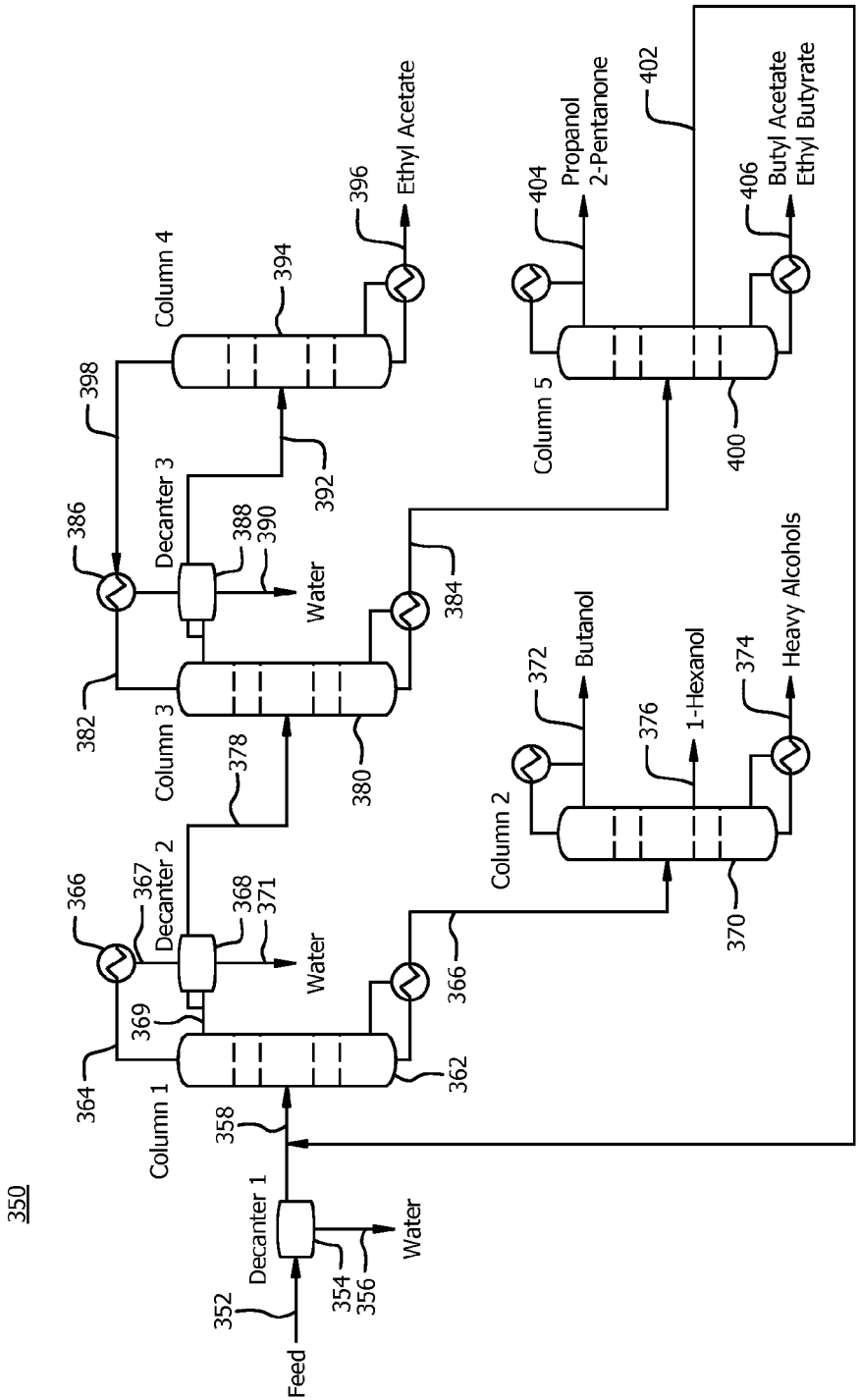
FIG. 10 illustrates a schematic flow diagram of a product separation system according to another embodiment.

Another embodiment of a separation scheme 350 for separating the components of a complex mixture is illustrated in FIG. 10. In this embodiment, the separation sequence may be used to recover one or more high purity higher alcohol streams, an ethyl acetate stream, and optionally one or more other valuable byproduct streams. In this embodiment, an inlet stream 352 may first be passed to a decanter 354. In an embodiment, the inlet stream 352 may be the product stream from any of the reactive distillation processes described herein. The inlet stream 352 may comprise a number of components including any of the products produced in the reactive distillation process described herein. In an embodiment, the inlet stream 352 to the separation sequence 350 comprise one or more higher alcohols (e.g., propanol, butanol, 1-hexanol, 1-octanol, 2-ethyl-1-butanol, 2-ethyl-1-hexanol, butanediol, octanol, decanol, dodecanol, and heavier alcohols, etc.), ethyl acetate, butyl acetate, ethyl butyrate, 2-pentanone, and possibly water. The inlet stream 352 can be passed through an optional inlet decanter 354 to remove any excess water that forms a separate liquid phase. The resulting water stream 356 comprising water and relatively minor amounts of dissolved organics can be passed out of the decanter 354 and discharged from the process. When the decanter 354 is used, the decanter 354 may be operated close to the bubble point of the inlet stream 352 mixture in order to minimize the amount of dissolved organics such as propanol and/or butanol in the aqueous phase.

The organic phase can exit the decanter 354 as liquid stream 358. The liquid stream 358 may be combined with a recycle stream 360 and the combined stream can be fed to a first distillation column 362. The first distillation column 362 may comprise any of the types of distillation columns described herein, and the first distillation column 362 may operate at a pressure ranging from about 0.1 atm to about 80 atm, or about 0.5 atm to about 40 atm. The first distillation column 362 may produce an overhead stream 364 and a bottoms stream 366. A portion of the bottoms stream 366 may pass through an exchanger to provide a vapor feed to the column 362, and the remaining portion may comprise one or more higher alcohols such as butanol, 1-hexanol, and/or the other higher alcohols.

The bottoms stream 366 from the first distillation column 362 can be further separated using one or more distillation columns to recover one or more high purity product streams. In an embodiment, the product streams can include product streams predominately comprising a single higher alcohol. For example, a further separation may produce product streams predominately comprising butanol and/or possibly 1-hexanol, and the remaining heavy alcohols can be produced individually or as a combined stream. In the embodiment shown in FIG. 10, the bottoms stream 366 can pass to a second distillation column 370. The second distillation column 370 may comprise any of the types of distillation columns described herein, and the second distillation column 370 may operate at a pressure ranging from about 0.1 atm to about 80 atm, or about 0.5 atm to about 40 atm. The second distillation column 370 may produce a plurality of product streams. In an embodiment, the second distillation column 370 may produce a butanol product stream 372 as the overhead product, an intermediate side stream 376 predominately comprising hexanol, and a bottoms stream comprising one or more higher alcohols having a boiling point higher than that of hexanol (e.g., 1-hexanol). In an embodiment, the butanol recovered in the butanol product stream 372 may have a purity of greater than about 90%, greater than about 95%, greater than about 96%, greater than about 97%, greater than about 98%, greater than about 99%, or greater than about 99.5% butanol by weight. In some embodiments, one or more of additional distillation columns may be combined with the first distillation column 362, and/or used to further purify the product streams from the second distillation column 370. For example, a further distillation column could be used to further separate out individual components of the bottoms product stream 374 from the second distillation column 370. In any of these columns, the desired products may be recovered as one or more side streams. In some embodiments, side rectifier or side stripper columns may also be used with the first distillation column 362 and/or the second distillation column 370 to improve the purity of the side stream products.

The overhead stream 364 from the first distillation column 362 may pass through a heat exchanger 366 to at least partially condense the overhead stream 364. The heat exchanger 368 may comprise any of the heat exchanger types described herein. The at least partially condensed stream 367 may pass to a decanter 368. In some embodiments, the decanter 368 may comprise a series of decanters operating at the same or different temperatures. The decanter(s) 368 may generate an aqueous stream and an organic stream. A fraction of the organic stream, and possibly a fraction of the aqueous stream, can be refluxed to the first distillation column 362. For example, the stream 369 may comprise a portion of the organic stream, and optionally, a portion of the aqueous stream. The remainder of the aqueous stream 369, which may comprise water with a relatively small amount of dissolved organics, may be recovered and discharged from the system. As noted above, the presence of water may be important in facilitating the separation of two or more of the organic components in the inlet stream 352. Consequently, a fraction of the aqueous stream 369 may also be recycled to either the first distillation column 362 and/or to the inlet stream 352 of the separation system 350, and/or combined stream 358. Additional water may be added to the first distillation column 362 and/or the inlet stream 352 or the combined stream 358 to facilitate the separation. The organic product stream 378 from the decanter 368 may comprise one or more higher alcohols and additional side products. In an embodiment, the organic product stream 378 may comprise one or more higher alcohols such as propanol and/or butanol as well as one or more additional organic components such as ethyl acetate, butyl acetate, ethyl butyrate, and/or 2-pentanone. The organic product stream 378 may also comprise water.

A number of alternative separation sequences may be used to recover any ethyl acetate, any remaining butanol, and potentially some of the valuable byproducts such as butyl acetate in the organic product stream 378. In the embodiment illustrated in FIG. 10, the organic product stream 378 can be sent to a distillation sequence comprising a decanter. The organic product stream 378 may first pass to a third distillation column 380. The third distillation column 380 may comprise any of the types of distillation columns described herein, and the third distillation column 380 may operate at a pressure ranging from about 0.1 atm to about 80 atm, or about 0.5 atm to about 40 atm. The third distillation column 380 may produce an overhead stream 382 and a bottoms stream 384.

The overhead stream 382 from the third distillation column 380 can be condensed in a heat exchanger 386 to at least partially condense the overhead stream 382. The heat exchanger 386 may comprise any of the heat exchanger types described herein. The at least partially condensed stream may pass a decanter 388, or possibly a series of decanter operating at the same or different temperatures. The decanter 388 may produce at least an organic phase stream and an aqueous phase stream. At least a portion of the organic phase stream, and also possibly a fraction of the aqueous phase, can be refluxed to the third distillation column 380. The remainder of the aqueous phase stream 390, which may comprise water with a relatively minor amount of dissolved organics, can be recovered and discharged from the system. The remainder of the organic phase stream 392, which can comprise organics including, but not limited to, ethyl acetate in addition to a minor amount of water, can be further separated to recover high purity ethyl acetate. In some embodiments, the organic phase stream 392 can be recycled to one or more reactors as a reactant.

The separation of the organic phase stream 392 may be achieved using a single distillation column (e.g., a fourth distillation column 4) as shown in FIG. 10. The fourth distillation column 394 may comprise any of the types of distillation columns described herein, and the fourth distillation column 394 may operate at a pressure ranging from about 0.1 atm to about 80 atm, or about 0.5 atm to about 40 atm. The fourth distillation column 394 may produce an overhead stream 398 and a bottoms stream 396. The bottoms stream 396 can comprise high purity ethyl acetate. In an embodiment, the ethyl acetate recovered in the bottoms stream may have a purity of greater than about 90%, greater than about 95%, greater than about 96%, greater than about 97%, greater than about 98%, greater than about 99%, or greater than about 99.5% ethyl acetate by weight. The overhead stream 398 can be passed to the heat exchanger 386, where at least a portion of the overhead stream 398 can be condensed and passed to at least one of the decanter 388 and/or the third distillation column 380.

The bottoms stream 384 from the third distillation column 380 can be passed to a fifth distillation column 400. The bottoms stream 384 may generally comprise a mixture of organics, which can include, but is not limited to, butyl acetate, ethyl butyrate, propanol, 2-pentanone, butanol, butyl acetate, and/or ethyl butyrate. The fifth distillation column 400 may comprise any of the types of distillation columns described herein, and the fifth distillation column 400 may operate at a pressure ranging from about 0.1 atm to about 80 atm, or about 0.5 atm to about 40 atm. The fifth distillation column 400 may produce a plurality of streams comprising an overhead stream 404, a bottoms stream 406, and/or one or more side product streams 402. The bottoms stream 406 may comprise butyl acetate and/or ethyl butyrate. The overhead stream may comprise propanol and/or 2-pentanone. The side product stream 402 may primarily comprise butanol, butyl acetate, and/or ethyl butyrate. The side product stream 402 can be recycled to the first distillation column 362, the feed 352, the combined stream 358, and/or to the decanter 368. In some embodiments, the fourth distillation column 394 and the fifth distillation column 400 may be combined into a single column operating at a pressure greater than about 3 atm, and the butanol can be recovered as a side product with an optional side rectifier used to improve the purity of the butanol product.

Figure 11:
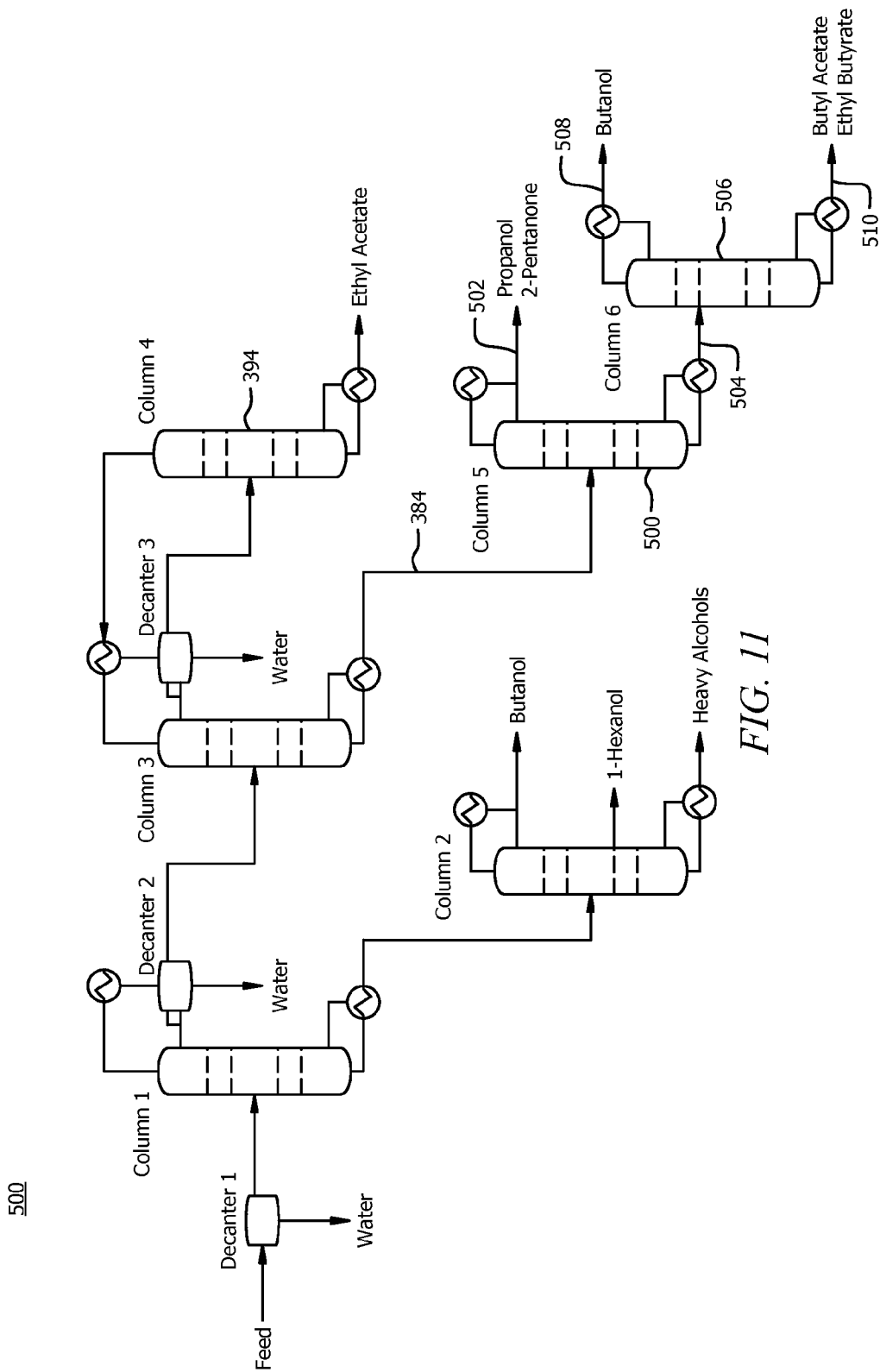
FIG. 11 illustrates a schematic flow diagram of a product separation system according to another embodiment.

Another embodiment of a separation process 500 is illustrated in FIG. 11. The separation process 500 is similar to the separation process 350 illustrated in FIG. 10 with the exception that the bottoms product stream 384 from the third distillation column 380 may pass to a different series of separation units. The remaining components of the separation process 500 may be the same or similar to those described with respect to FIG. 10, and the similar components will not be described with respect to FIG. 11 in the interest of brevity. In this embodiment, the bottoms stream 384 can pass to a fifth distillation column 500. The fifth distillation column 500 may comprise any of the types of distillation columns described herein, and the fifth distillation column 500 may operate at a pressure ranging from about 0.1 atm to about 80 atm, or about 0.5 atm to about 40 atm. The fifth distillation column 500 may produce an overhead stream 502 and a bottoms stream 504. The overhead stream 502 may comprise propanol and/or 2-pentanone.

The bottoms stream 504 from the fifth distillation column 500 can comprise butanol, ethyl butyrate, and/or butyl acetate, and the bottoms stream 504 can pass to a sixth distillation column 506, which may operate at a pressure of greater that about 3 atm. The sixth distillation column 506 may comprise any of the types of distillation columns described herein, and the sixth distillation column 506 may operate at a pressure ranging from about 3 atm to about 80 atm. In general, a butanol-butyl acetate azeotrope may limit the purity of any butanol recovered using distillation in a mixture of butanol and butyl acetate. However, the azeotrope is pressure sensitive and is not present at a pressure greater than about 3 atm. Operating the sixth distillation column at a pressure greater than about 3 atm can allow the overhead stream to comprise high purity butanol. In an embodiment, the butanol recovered in the overhead stream 508 may have a purity of greater than about 90%, greater than about 95%, greater than about 96%, greater than about 97%, greater than about 98%, greater than about 99%, or greater than about 99.5% butanol by weight. The bottoms stream 510 may comprise butyl acetate and/or ethyl butyrate. In some embodiments, the fourth distillation column 394 and the fifth distillation column 500 may be combined into a single column operating at a pressure greater than about 3 atm, and the butanol can be recovered as a side product with an optional side rectifier used to improve the purity of the butanol product.

Figure 12:
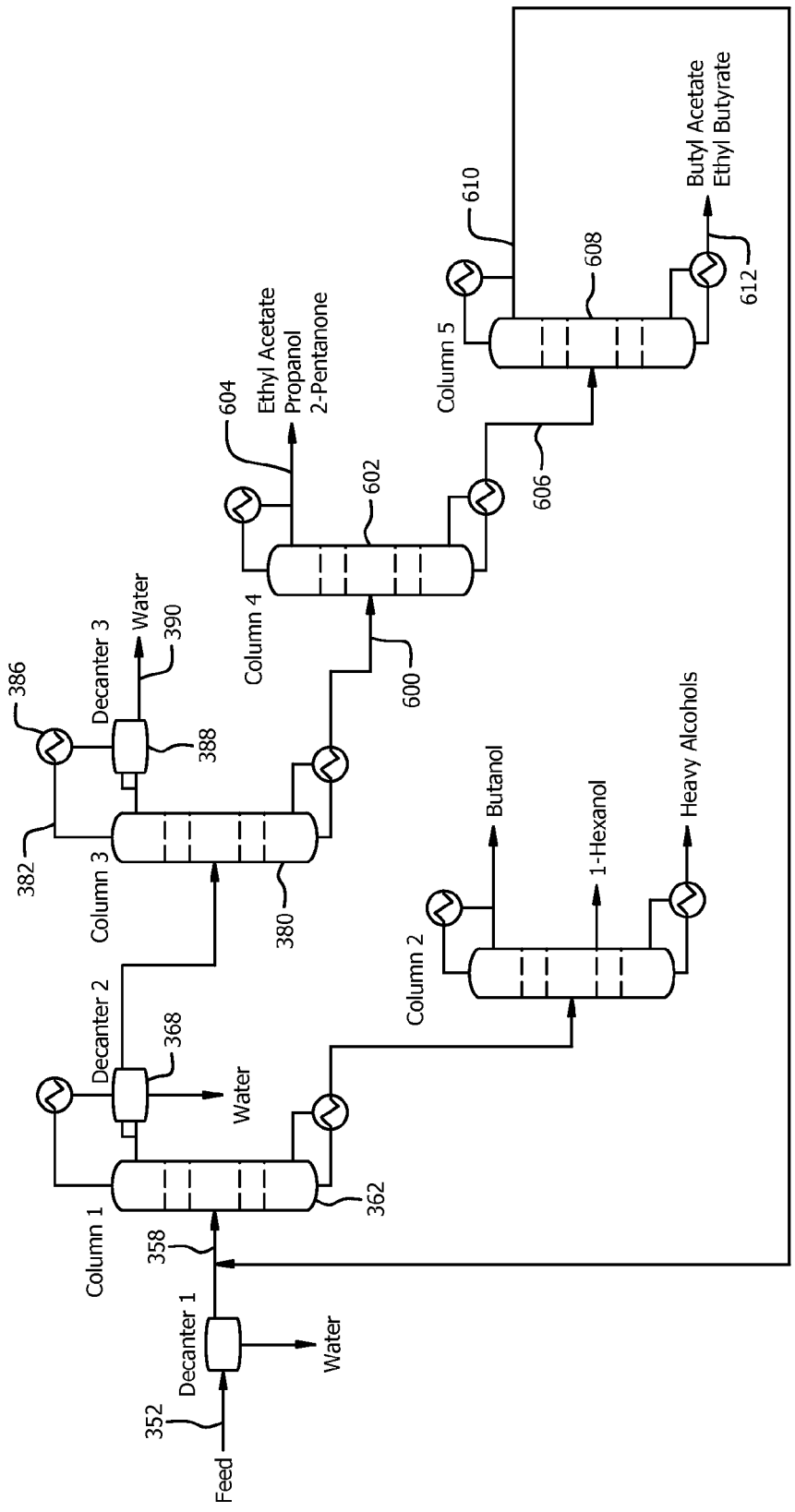
FIG. 12 illustrates a schematic flow diagram of a product separation system according to another embodiment.

Another embodiment of a separation process 600 is illustrated in FIG. 12 for recovering a higher alcohol such as butanol from the organic phase stream from the decanter 368. The separation process 600 is similar to the separation process 350 illustrated in FIG. 10 with the exception that the organic phase stream from the decanter 388 is recycled to the third distillation column 380 and the bottoms stream 600 from the third distillation column 380 may pass to a different series of separation units. The remaining components of the separation process 600 may be the same or similar to those described with respect to FIG. 10, and the similar components will not be described with respect to FIG. 12 in the interest of brevity.

In this embodiment, the overhead stream from the third distillation column 380 can be at least partially condensed in the heat exchanger 386 and pass to the decanter 388. The organic phase, and optionally a fraction of the aqueous phase, can be refluxed to the third distillation column 380. The remainder of the aqueous phase can pass out of the decanter 388 and be discharged from the process as the aqueous phase stream 390. The aqueous phase stream 390 may predominately comprise water with a minor amount of dissolved organics.

In this embodiment, the bottoms stream 600 from the third distillation column 380 can pass to a fourth distillation column 602, where the bottoms stream 600 comprises organics that are substantially free of water. The fourth distillation column 602 may comprise any of the types of distillation columns described herein, and the fourth distillation column 602 may operate at a pressure ranging from about 0.1 atm to about 80 atm, or about 0.5 atm to about 40 atm. The fourth distillation column 602 may produce an overhead stream 604 and a bottoms stream 606. The bottoms stream 606 may comprise butanol, butyl acetate, and/or ethyl butyrate, while the remainder of the feed, which may potentially be added to a gasoline pool, can be recovered as the overhead stream 604.

In an embodiment, the overhead stream 604 can comprise ethyl acetate, propanol, and/or 2-pentanone.

The bottoms stream 606 from the fourth distillation column 602 can be further separated in a fifth distillation column 608. The fifth distillation column 608 may comprise any of the types of distillation columns described herein, and the fifth distillation column 608 may operate at a pressure ranging from about 0.1 atm to about 80 atm, or about 0.5 atm to about 40 atm. The fifth distillation column 608 may produce an overhead stream 610 and a bottoms stream 612. The bottoms stream 612 may comprise butyl acetate and/or ethyl butyrate as the bottoms product. The overhead stream 610, depending on the pressure at which the fifth distillation column 608 is operating, may comprise high purity butanol (e.g., when the pressure is greater than about 3 atm) or mixture comprising predominantly of butanol, butyl acetate, and/or ethyl butyrate (e.g., when the pressure is below about 3 atm). The overhead stream 610 can be recycled to the first distillation column 362, or inlet stream 352. In some embodiments, two or more of the columns (e.g., the third distillation column 380, the fourth distillation column 602, and/or the fifth distillation column 608) may be combined into a single column, with the desired streams recovered as side streams. In addition, side rectifiers/strippers may be used to enhance the purity of the side stream products.

The selection of the appropriate separation scheme may be based on the composition of the inlet mixture 352, the composition of the desired products (e.g., one or more high purity streams and/or one or more mixed streams), and/or the economics of the overall process. In addition, various modifications and alterations are contemplated when the relative proportion and compositions of the higher alcohols change. For example, the heavier alcohol stream 374 may be further separated in one or more separation steps when individual higher product alcohol streams are desired.

Suitable higher alcohol(s) conversion catalysts and combinations thereof are capable of converting at least a portion of the one or more alpha hydrogen alcohol(s) (e.g., primary or secondary alcohol(s) such as ethanol) in a feed stream to a higher valued product such as one or more higher alcohols. As noted above, higher alcohols refer to alcohols have a higher molecular weight than the alcohol forming the reactant in the formation process (e.g., $C_6$-$C_{13}$ alcohols, or higher alcohols). The higher alcohols can include n-butanol and other isomers of butanol as well as significant amounts of 1-hexanol, 2-ethylbutanol, 1-octanol, 2-ethylhexanol, and other higher alcohol isomers (e.g., isomers of hexanol, octanol, decanol, dodecanol, etc.).

Suitable higher alcohol conversion catalysts may comprise any catalyst capable of carrying out a dehydration, dehydrogenation, and dimerization aldol condensation reaction, and may be used alone or in combination with additional catalytic materials in the reactors. In an embodiment, suitable higher alcohol conversion catalysts can generally comprise metals, oxides, or salts, or any combination thereof, of copper, barium, ruthenium, rhodium, platinum, palladium, rhenium, silver, cadmium, zinc, zirconium, gold, thallium, magnesium, manganese, aluminum, chromium, nickel, iron, molybdenum, sodium, strontium, tin, and mixtures thereof. In many cases, the butanol conversion catalyst material will be provided on a support material. The higher alcohol conversion catalyst can be treated with a carbonate (e.g., sodium carbonate), reduced with hydrogen, and/or other suitable treatments prior to use.

In general, catalysts for the production of one or more higher alcohols may produce only higher alcohol(s) or both higher alcohol(s) and ethyl acetate. Suitable catalysts for producing higher alcohol(s) with only trace amounts of by-products include Guerbet reaction catalysts, including but not limited to hydroxyapatite and solid base Guerbet reaction catalysts, solid base multicomponent oxide catalysts, zeolites with alkali counterions, magnesium oxide, or any combination thereof.

The higher alcohol(s) conversion catalyst may comprise nickel or nickel oxide supported on alumina, and the butanol conversion catalyst may have a nickel weight loading of between about 2% and about 20%. The higher alcohol(s) conversion catalyst may comprise co-precipitated catalysts represented by the formula:

$$M/MgO/Al_2O_3,$$

wherein M represents palladium, rhodium, nickel, or copper, or oxides thereof.

The higher alcohol(s) conversion catalyst may comprise oxide powders of copper, lead, zinc, chromium, molybdenum, tungsten, manganese, lead, salts thereof, and any combination thereof. In an embodiment, the higher alcohol(s) conversion catalyst may comprise a zeolite with an alkali metal.

The higher alcohol(s) conversion catalyst may comprise solid base catalysts and solid acid/base bifunctional catalysts. The higher alcohol(s) conversion catalyst may comprise a hydroxyapatite represented by the formula $$Ca_{10}(PO_4)_6(OH)_2$$

wherein the ratio of calcium to phosphorus (Ca:P) is between about 1.5 and about 1.8 for nonstoichiometric hydroxyapatites. The higher alcohol(s) conversion catalyst may comprise an apatite structure satisfying the formula:

$$M_a(M'O_b)_cX_2,$$

wherein M represents calcium, strontium, magnesium, barium, lead, cadmium, iron, cobalt, nickel, or zinc, M' represents phosphorus, vanadium, arsenic, carbon, or sulfur, and X represents a fluorine, chlorine, bromine, or a hydroxide. In one embodiment, a, b, and c are whole numbers that balance the valence requirements of M, M', and X. In another embodiment, a is 10, b is 3, and c is 6. In another embodiment, $M_a(M'O_b)_cX_2$ is a non-stoichiometric apatite, and a is about 10, b is about 3, c is about 6, and the ratio of a to c (a:c) is between about 1.5 and about 1.8. The higher alcohol(s) conversion catalyst may comprise a basic a calcium and/or magnesium phosphate compound including calcium and/or magnesium phosophates, phosphate carbonates, pyrophosphates, or the like. In an embodiment, the higher alcohol(s) conversion catalyst may also comprise magnesium oxide, magnesium hydroxide, magnesium phosphate hydrate ($Mg_3$ $(PO_4)_2.8H_2O$), calcium oxide, calcium hydroxide, calcium fluoride, calcium silicate (wollastonite), calcium sulfate dihydrate (gypsum), lithium phosphate, aluminum phosphate, titanium dioxide, fluorapatite ($Ca_{10}(PO_4)_6F_2$), tetracalcium phosphate (e.g. $Ca_4(PO_4)_2O$), hydrotalcite, talc, kaolin, sepiolite, or any combination thereof.

In certain embodiments, the higher alcohol(s) conversion catalyst may include a catalyst support. The catalyst support stabilizes and supports the catalyst. The type of catalyst support used depends on the chosen catalyst and the reaction conditions. Suitable supports may include, but are not limited to, carbon, silica, silica-alumina, alumina, zirconia, titania, ceria, vanadia, boron nitride, heteropolyacids, hydroxyapatite, zinc oxide, chromia, zeolites, carbon nanotubes, carbon fullerenes, and any combination thereof.

The higher alcohol(s) conversion catalyst can be employed in any of the conventional types or structures known to the art. It may be employed in the form of extrudates, pills, pellets, granules, broken fragments, or various special shapes. In an embodiment, consideration of the use of the higher alcohol(s) conversion catalyst in the reactive distillation system and/or as a mass transfer surface within the distillation column may be taken into account when determining a suitable shape. For example, the higher alcohol(s) conversion catalyst may have a shape similar to structured packing material or suitable for insertion in a structured packing. When the higher alcohol(s) conversion catalyst is used with one or more side reactors, the catalyst may be disposed within a reaction zone, and the feed may be passed therethrough in the liquid, vapor, or mixed phase, and in either upward or downward, or inward or outward flow.

In an embodiment, the higher alcohol(s) conversion catalyst described herein may be capable of achieving a relatively high conversion and/or selectivity of an alpha hydrogen alcohol to one or more higher alcohols such as butanol (e.g., n-butanol and/or 2-butanol), hexanol, octanol, decanol, dodecanols, etc. As used herein, the "conversion" of an alpha hydrogen alcohol to a higher alcohol (HA) refers to the amount of the alpha hydrogen alcohol (AHA) consumed in the conversion reaction as represented by the formula:

$$X_{AHA} = 100\left(\frac{n_{AHA} - n_{AHA,0}}{n_{AHA,0}}\right) \quad \text{(Eq. 7)}$$

where $n_{AHA}$ represents the molar flow rates of the alpha hydrogen alcohol in the reactor effluent (e.g., the product stream comprising the higher alcohol), and $n_{AHA,0}$ represents the molar flow rate of the alpha hydrogen alcohol into the reactor inlet. As used herein, the "higher alcohol selectivity" of the conversion refers to the amount of the alpha hydrogen alcohol that is consumed in the conversion reaction that is converted to one or more higher alcohols as represented by the formula:

$$S_{HA} = 100\left(\frac{2n_{HA}}{n_{AHA} - n_{AHA,0}}\right) \quad \text{(Eq. 8)}$$

where $n_{HA}$ and $n_{AHA}$ represent the molar flow rate of the higher alcohol(s) and the alpha hydrogen alcohol(s) in the reactor effluent (e.g., the product stream comprising the butanol), respectively, and the remaining terms are the same as described above with respect to the conversion of the alpha hydrogen alcohol(s). In an embodiment, the higher alcohol(s) conversion catalyst described herein may be capable of achieving a conversion of the alpha hydrogen alcohol(s) in the reactive distillation process described herein of at least about 10%, at least about 20%, at least about 30%, at least about 40%, or at least about 50%. In an embodiment, the higher alcohol conversion catalyst described herein may be capable of achieving a selectivity of higher alcohol(s) ($S_{HA}$) in the reactive distillation process described herein of at least about 60%, at least about 70%, at least about 80%, at least about 85%, at least about 90%, or at least about 95%. The catalyst may be produced using a variety of techniques as described in more detail below.

Suitable conversion catalysts and combinations thereof are capable of converting at least a portion of the alcohol (e.g., the alpha hydrogen alcohol) in a feed stream to two or more higher valued products. For example, suitable conversion catalysts, and combinations thereof are capable of producing one or more higher alcohols and/or ethyl acetate from the alpha hydrogen alcohol(s) (e.g., ethanol). Suitable conversion catalysts may comprise any catalyst capable of carrying out a dehydration, dehydrogenation, and dimerization aldol condensation reaction, a dehydrogenation and dimerization reaction, or a combination thereof, and may be used alone or in combination with additional catalytic materials in the reactors. In an embodiment, suitable conversion catalysts can generally comprise metals, oxides, or salts, or any combination thereof, of copper, barium, ruthenium, rhodium, platinum, palladium, rhenium, silver, silicon, calcium, cadmium, zinc, zirconium, gold, thallium, magnesium, manganese, aluminum, chromium, nickel, iron, molybdenum, sodium, strontium, tin, and mixtures thereof. In many cases, the conversion catalysts material will be provided on a support material. The conversion catalysts can be treated with a carbonate (e.g., sodium carbonate), reduced with water, and/or other suitable treatments prior to use.

Examples of suitable conversion catalysts include, but are not limited to, $CuO/SiO_2$, $CuO/SiO_2$—$Al_2O_3$, $CuO/ZnO$, $CuO/ZrO_2$, $CuO/SiO_2$—$ZrO_2$, $CuO/Al_2O_3$, or any combination thereof. In an embodiment, the $CuO/SiO_2$, $CuO/SiO_2$—$Al_2O_3$, $CuO/ZnO$, $CuO/ZrO_2$, $CuO/SiO_2$—$ZrO_2$, $CuO/Al_2O_3$, or any combination thereof may be prepared via impregnation of an oxide catalyst, such as, for example, by the impregnation techniques disclosed herein and described in more detail below.

Examples of suitable conversion catalysts also include, but are not limited to, $CuO/ZnO/SiO_2$, $CuO/ZrO_2/SiO_2$, $CuO/MgO/SiO_2$, $CuO/CaO/SiO_2$, $CuO/SrO/SiO_2$, $CuO/BaO/SiO_2$, $CuO/ZrO_2/Al_2O_3/SiO_2$, $CuO/Na_2O/SiO_2$, $CuO/MgO/Al_2O_3/SiO_2$ $CuO/CeO_2/MgO/Al_2O_3$ or any combination thereof. In an embodiment, the $CuO/ZnO/SiO_2$, $CuO/ZrO_2/SiO_2$, $CuO/MgO/SiO_2$, $CuO/CaO/SiO_2$, $CuO/SrO/SiO_2$, $CuO/BaO/SiO_2$, $CuO/ZrO_2/Al_2O_3/SiO_2$, $CuO/Na_2O/SiO_2$, or any combination thereof may be prepared via co-impregnation of a silica catalyst support, such as, for example, by the co-impregnation techniques disclosed herein and described in more detail below. In an another embodiment, the $CuO/ZnO/SiO_2$, $CuO/ZrO_2/SiO_2$, $CuO/MgO/SiO_2$, $CuO/CaO/SiO_2$, $CuO/SrO/SiO_2$, $CuO/BaO/SiO_2$, $CuO/ZrO_2/Al_2O_3/SiO_2$, $CuO/Na_2O/SiO_2$, $CuO/K_2O/SiO_2$, $CuO/Rb_2O/SiO_2$, $CuO/Cs_2O/SiO_2$, or any combination thereof may be prepared via sequential impregnation of a silica catalyst support, such as, for example, by the sequential impregnation techniques disclosed herein and described in more detail below.

Examples of suitable conversion catalysts also include, but are not limited to, $CuO/ZnO/Al_2O_3$, $CuO/Cr_2O_3/Al_2O_3$, $CuO/ZrO_2/Al_2O_3$, or any combination thereof. In an embodiment, the $CuO/ZnO/Al_2O_3$, $CuO/Cr_2O_3/Al_2O_3$, $CuO/ZrO_2/Al_2O_3$, or any combination thereof may be prepared via co-impregnation of an alumina support, such as, for example, by the co-impregnation techniques disclosed herein and described in more detail below.

Suitable conversion catalysts include Guerbet reaction catalysts, including but not limited to hydroxyapatite and solid base Guerbet reaction catalysts, solid base multicomponent oxide catalysts, zeolites with alkali counterions, magnesium oxide, or any combination thereof capable of converting at least a portion of the alpha hydrogen alcohol(s) (e.g., ethanol) in a feed stream to two or more higher valued products, the production of one or more higher alcohols (via a dehydration mechanism) and/or ethyl acetate (via a dehydrogenation mechanism) for example.

The conversion catalyst may comprise nickel or nickel oxide supported on alumina, and the conversion catalyst may have a nickel weight loading of between about 2% and about 60%. The conversion catalyst may comprise co-precipitated catalysts represented by the formula:

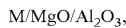

$M/MgO/Al_2O_3$, wherein M represents palladium, rhodium, nickel, copper, or oxides thereof.

The conversion catalyst may comprise oxide powders of copper, lead, zinc, chromium, molybdenum, tungsten, manganese, lead, salts thereof, and any combination thereof. In an embodiment, the conversion catalyst may comprise a zeolite with an alkali metal.

The conversion catalyst may comprise solid base catalysts and solid acid/base bifunctional catalysts. The conversion catalyst may comprise a hydroxyapatite represented by the formula

$Ca_{10}(PO_4)_6(OH)_2$ wherein the ratio of calcium to phosphorus (Ca:P) is between about 1.5 and about 1.8 for nonstoichiometric hydroxyapatites. The conversion catalyst may comprise an apatite structure satisfying the formula:

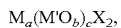

$M_a(M'O_b)_cX_2$, wherein M represents calcium, strontium, magnesium, barium, lead, cadmium, iron, cobalt, nickel, or zinc, M' represents phosphorus, vanadium, arsenic, carbon, or sulfur, and X represents a fluorine, chlorine, bromine, or a hydroxide. In one embodiment, a, b, and c are whole numbers that balance the valence requirements of M, M', and X. In another embodiment, a is 10, b is 3, and c is 6. In another embodiment, $M_a(M'O_b)_cX_2$ is a non-stoichiometric apatite, and a is about 10, b is about 3, c is about 6, and the ratio of a to c (a:c) is between about 1.5 and about 1.8. The conversion catalyst may comprise a basic a calcium and/or magnesium phosphate compound including calcium and/or magnesium phosophates, phosphate carbonates, pyrophosphates, or the like. In an embodiment, the conversion catalyst may also comprise magnesium oxide, magnesium hydroxide, magnesium phosphate hydrate ($Mg_3(PO_4)_2.8H_2O$), calcium oxide, calcium hydroxide, calcium fluoride, calcium silicate (wollastonite), calcium sulfate dihydrate (gypsum), lithium phosphate, aluminum phosphate, titanium dioxide, fluorapatite ($Ca_{10}(PO_4)_6F_2$), tetracalcium phosphate ($Ca_4(PO_4)_2O$), $Ca_2P_2O_7$, hydrotalcite, talc, kaolin, sepiolite, or any combination thereof.

In certain embodiments, the conversion catalyst may include a catalyst support. The catalyst support stabilizes and supports the catalyst. The type of catalyst support used depends on the chosen catalyst and the reaction conditions. Suitable supports may include, but are not limited to, carbon, silica, silica-alumina, alumina, zirconia, titania, ceria, vanadia, nitride, boron nitride, heteropolyacids, hydroxyapatite, zinc oxide, chromia, zeolites, carbon nanotubes, carbon fullerenes, and any combination thereof.

The conversion catalyst can be employed in any of the conventional types or structures known to the art. It may be employed in the form of extrudates, pills, pellets, granules, broken fragments, or various special shapes. In an embodiment, consideration of the use of the conversion catalysts in the reactive distillation system and/or as a mass transfer surface within the distillation column may be taken into account when determining a suitable shape. For example, the conversion catalysts may have a shape similar to structured packing material or suitable for insertion in a structured packing. When the hydrogenating catalyst is used with one or more side reactors, the catalyst may be disposed within a reaction zone, and the feed may be passed therethrough in the liquid, vapor, or mixed phase, and in either upward or downward, or inward or outward flow.

The conversion catalyst may typically have a range of metal loadings. In an embodiment, the conversion catalysts may have a copper oxide weight loading (i.e., weight percentage) of between about 0.5% and about 80%, between about 10% and about 70%, between about 20% and about 65%, between about 30% and about 60%, or about 40% and about 50%. In an embodiment, the conversion catalysts may have an a aluminum oxide weight loading of between about 20% and about 60%, between about 30% and about 50%, or between about 40% and about 50%. In an embodiment, the conversion catalysts may have a zirconium dioxide weight loading of between about 20% and about 60%, or between about 30% and about 50%.

In an embodiment, the conversion catalysts may comprise $CuO/Al_2O_3$ disposed on a zirconium dioxide support. In this embodiment, the conversion catalysts may have a copper oxide weight loading of between about 0.5% and about 80%, between about 10% and about 70%, between about 20% and about 65%, between about 30% and about 60%, or about 40% and about 50%, and the alumina and zirconium dioxide may comprise the balance of the weight. In an embodiment, the conversion catalysts may comprise $CuO/ZrO_2$ disposed on an alumina support. In this embodiment, the conversion catalysts may have a copper oxide weight loading of between about 0.5% and about 80%, between about 10% and about 70%, between about 20% and about 65%, between about 30% and about 60%, or about 40% and about 50%, and the alumina and zirconium dioxide may comprise the balance of the weight.

In an embodiment, the catalysts for co-producing higher alcohol(s) and ethyl acetate from ethanol described herein may be capable of achieving a relatively high conversion and/or selectivity of the alpha hydrogen alcohol(s) to one or more higher alcohols and ethyl acetate. As used herein, the "conversion" of the alpha hydrogen alcohol to the higher alcohol(s) and ethyl acetate refers to the amount of the alpha hydrogen alcohol(s) consumed in the conversion reaction as represented by the formula:

$$X_{AHA} = 100\left(\frac{n_{AHA} - n_{AHA,0}}{n_{AHA,0}}\right) \quad \text{(Eq. 6)}$$

where $n_{AHA}$ represents the molar flow rates of the alpha hydrogen alcohol(s) in the reactor effluent (e.g., the product stream comprising the higher alcohol(s)), and $n_{AHA,0}$ represents the molar flow rate of the alpha hydrogen alcohol(s) into the reactor inlet. As used herein, the "total selectivity" of the conversion refers to the amount of the alpha hydrogen alcohol that is consumed in the conversion reaction that is converted to the one or more higher alcohol(s) and ethyl acetate and as represented by the formula:

$$S_{total} = 100\left(\frac{2n_{EtOAc} + 2n_{HA} + 2n_{AcH}}{n_{AHA} - n_{AHA,0}}\right) \quad \text{(Eq. 8)}$$

where $n_{AHA}$, $n_{HA}$, and $n_{AcH}$ represent the molar flow rate of the alpha hydrogen alcohol(s), the one or more higher alcohols, and acetaldehyde in the reactor effluent (e.g., the product stream comprising the higher alcohols), respectively, and the remaining terms are the same as described above with respect to the conversion of the alpha hydrogen alcohol(s). Acetaldehyde is an intermediate product in the reaction to make ethyl acetate (and possibly for the reaction to make one or more of the higher alcohols) and is therefore included in the total selectivity calculation. In an embodiment, the conversion catalyst described herein may be capable of achieving a conversion of the alpha hydrogen alcohol(s) in the reactive distillation process described herein of at least about 10%, at least about 20%, at least about 30%, at least about 40%, or at least about 50%. In an embodiment, the conversion catalyst described herein may be capable of achieving a total selectivity ($S_{total}$) in the reactive distillation process described herein of at least about 60%, at least about 70%, at least about 80%, at least about 85%, at least about 90%, or at least about 95%.

It is to be understood that the catalysts for the coproduction of the higher alcohol(s) and ethyl acetate may include a blend of one or more catalysts that convert the alpha hydrogen alcohol(s) to pure or substantially pure higher alcohol(s) with one or more catalysts that convert the alpha hydrogen alcohol(s) to pure or substantially pure ethyl acetate. Catalysts that convert the alpha hydrogen alcohol(s) to pure or substantially pure ethyl acetate include, but are not limited to, the catalysts disclosed in U.S. Patent Publication No. 2013/0197266 entitled "Ethyl Acetate Production," to Gadewar, et al, which is incorporated herein by reference in its entirety. Various catalysts of U.S. Patent Publication No. 2013/0197266 suitable for use in the production of higher alcohol(s) and/or ethyl acetate are further described in Examples 5-8 of the present application. The catalysts of Examples 5-8, however, are not intended to be a complete listing of all catalysts from U.S. Patent Publication No. 2013/0197266 suitable for use in the higher alcohol(s) and/or ethyl acetate production processes, systems, and methods of the present application. The conversion catalysts may be produced using a variety of techniques as described in more detail below.

The hydrogenating catalyst generally can include a Group VIII metal and/or a Group VI metal. Examples of such a catalyst can include, but is not limited to, Cu, Re, Ni, Fe, Co, Ru, Pd, Rh, Pt, Os, Ir, and alloys, oxides (e.g., $PtO_2$), or any combination thereof, either alone or with promoters such as W, Mo, Au, Ag, Cr, Zn, Mn, Sn, B, P, Bi, and alloys, oxides (e.g., $Cr_2O_3$, $Cu_2Cr_2O_5$), or any combination thereof. Other effective hydrogenating catalyst materials include either supported nickel or ruthenium modified with rhenium. In an embodiment, the hydrogenating catalyst also includes any one of the supports described below, depending on the desired functionality of the catalyst. The hydrogenating catalysts may be prepared by methods known to those of ordinary skill in the art.

In an embodiment, the hydrogenating catalyst includes a supported Group VIII metal catalyst and a metal sponge material (e.g., a sponge nickel catalyst such as Raney nickel). Raney nickel provides an example of an activated sponge nickel catalyst suitable for use in this invention. In an embodiment, the hydrogenation reaction in the invention is performed using a catalyst comprising a nickel-rhenium catalyst or a tungsten-modified nickel catalyst. One example of a suitable catalyst for the hydrogenation reaction of the invention is a carbon-supported nickel-rhenium catalyst.

In an embodiment, a suitable Raney nickel catalyst may be prepared by treating an alloy of approximately equal amounts by weight of nickel and aluminum with an aqueous alkali solution, e.g., containing about 25 wt % of sodium hydroxide. The aluminum is selectively dissolved by the aqueous alkali solution resulting in a sponge shaped material comprising mostly nickel with minor amounts of aluminum. The initial alloy includes promoter metals (e.g., molybdenum or chromium) in the amount such that 1 to 2 wt % remains in the formed sponge nickel catalyst. In another embodiment, the hydrogenating catalyst is prepared using a solution of ruthenium(III) nitrosylnitrate or ruthenium (III) chloride in water to impregnate a suitable support material. The solution is then dried to form a solid having a water content of less than 1% by weight. The solid is then reduced at atmospheric pressure in a hydrogen stream at 300° C. (uncalcined) or 400° C. (calcined) in a rotary ball furnace for 4 hours. After cooling and rendering the catalyst inert with nitrogen, 5% by volume of oxygen in nitrogen is passed over the catalyst for 2 hours.

In certain embodiments, the hydrogenating catalyst may include a catalyst support, which may be the same or different than a catalyst support used with the conversion catalyst. In an embodiment, any of the catalyst supports discussed herein may be used to support a hydrogenating catalyst. The hydrogenating catalyst can be employed in any of the conventional types or structures known to the art. In an embodiment, any of the catalyst shapes and/or types discussed herein with respect to the conversion catalyst may be used with the hydrogenating catalyst.

Any of the materials useful as catalysts, may be synthesized using a variety of methods. In an embodiment, the catalyst may be prepared via wet impregnation of a catalyst support. Using the wet-impregnation technique, a metal salt (e.g., a metal nitrate, acetate, etc.) dissolved in a suitable solvent may be used to prepare the catalyst, however any soluble compound would be suitable. A sufficient amount of solvent should be used to fully dissolve the metal nitrate and appropriately wet the support. In one embodiment, copper nitrate and ethanol and/or water may be mixed in an amount sufficient such that the copper nitrate dissolves. Additional metal nitrates may also be added to provide a catalyst with additional components. The solute may then be combined with a suitable support material of appropriate particle size. The mixture may then be refluxed at a temperature of approximately 100° C. for approximately several hours (e.g., three to five hours) and then allowed to dry at a temperature of about 110° C. The dried material may then be heated to 200° C. to at least partially decompose the nitrates to the corresponding oxides, and then the materials may be calcined at about 400° C. to about 600° C. at a heating rate of about one to ten ° C./min over a period of about 2 to about 10 hours to fully remove the $NO_x$ component. The amount of metal nitrate used in the wet-impregnation technique can be adjusted to achieve a desired final metal weight loading of the catalyst support.

When multiple components are used to provide a catalyst disposed on a support, each component can be added via the wet-impregnation technique. The appropriate salts can be dissolved and impregnated on a support in a co-impregnation process or a sequential process. In a co-impregnation process, measured amount of the appropriate plurality of metal salts may be dissolved in a suitable solvent and used to wet the desired catalyst support. The impregnated support can then be dried and calcined to provide a final catalyst with a desired weight loading. In the sequential impregnation process, one or more measured amounts of salts may be dissolved in a suitable solvent and used to wet the desired catalyst support. The impregnated support can then be dried and calcined. The resulting material can then be wetted with one or more additional salts that are dissolved in a suitable solvent. The resulting material can then be dried and calcined again. This process may be repeated to provide a final catalyst material with a desired loading of each component. In an embodiment, a single metal may be added with each cycle. The order in which the metals are added in the sequential process can be varied. Various metal weight loadings may be achieved through the wet-impregnation technique. In an embodiment, the wet-impregnation technique may be used to provide a catalyst having a copper weight loading ranging from about 0.5% and about 50%, with one or more additional components having a weight loading between about 0.1% and about 40% each.

The catalysts may also be prepared via a co-precipitation technique. In this technique, a measured amount of one or more appropriate metal nitrates are dissolved in de-ionized water. The total metal concentration can vary and may generally be between about 0.01 M and about 3 M. The metal-nitrate solution may then be precipitated through the drop-wise addition of the solution to a stirred, equal volume of a sodium hydroxide solution at room temperature. The sodium hydroxide solution may generally have a concentration of about 4M, though other concentrations may also be used as would be known to one of skill in the art with the benefit of this disclosure. In some embodiments, the solutions may be combined in the opposite order. For example, the metal salt solution may be prepared and added (e.g., added drop-wise) to a basic solution such as a sodium hydroxide solution. The order of the addition (e.g., metal salt solution to the basic solution or the basic solution to the metal salt solution) may affect the composition of the precipitate formed during the precipitation process.

After addition of the metal nitrate solution or vice versa, the suspension may then be stirred over a period of about 1 to about 24 hours. The resulting suspension can then be filtered and washed with de-ionized water. The filtered solids can be dried overnight, for example, at a temperature of about 110° C., and then the materials may, optionally, be calcined at about 220° C. to about 500° C. at a heating rate of about one to ten ° C./min. The resulting mixed metal oxide can then be processed to a desired particle size. For example, the resulting mixed metal oxide can be pressed to a desired form, ground, and then sieved to recover a catalyst material with a particle size in a desired range. Catalysts prepared using the co-precipitation technique may have higher metal loadings than the catalysts prepared using the wet-impregnation technique.

Catalysts prepared via the co-precipitation technique may be used in the prepared form and/or a catalyst binder can be added to impart additional mechanical strength. In an embodiment, the prepared catalyst may be ground to a fine powder and then stirred into a colloidal suspension (e.g., a colloidal suspension of silica and/or alumina) in an aqueous and/or organic solution. The resulting suspension may be stirred while being heated and allowed to evaporate to dryness. The heating may take place at about 80° C. to about 130° C. The resulting solid can then be processed to a desired particle size. For example, the resulting solid can be extruded or pressed to a desired form, ground, and then sieved to recover a catalyst material with a particle size in a desired range. Alternatively, the colloidal suspension may be added to the 4M sodium hydroxide precipitation solution prior to addition of the metal nitrate solution in the co-precipitation technique. Other metal salts, such as acetates chlorides, sulfates, and the like can be used in place of the metal nitrates.

Various metal weight loadings may be achieved through the co-precipitation technique. In an embodiment, the co-precipitation technique may be used to provide a catalyst having a copper weight loading ranging from about 2% to about 80%, with one or more additional component having a weight loading between about 2% and about 40%.

The resulting catalyst from either the wet-impregnation technique and/or the co-precipitation technique may be further treated prior to use in the reactive distillation system disclosed herein. In an embodiment, the catalyst may be treated with a basic solution such as a sodium carbonate solution or a diluted sodium hydroxide solution for a period of time to improve the selectivity of the catalyst. In this process, the catalyst may be soaked in an aqueous solution of sodium carbonate for a period of time ranging from about 1 hour to about 48 hours, or alternatively about 2 hours to about 24 hours. In an embodiment, the sodium carbonate solution may have a concentration of about 0.2 M. The catalyst may then be filtered and allowed to dry at about room temperature. In an embodiment, the sodium carbonate may comprise from about 0.2 to about 3.0 weight percent of the catalyst after being contacted with the sodium carbonate solution.

In another treatment process, the catalyst may be reduced with hydrogen prior to use. In this embodiment, the catalyst may be heated and contacted with hydrogen, which may be flowing over the catalyst, for a period of time sufficient to reduce the catalyst to a desired degree. In an embodiment, the catalyst may be contacted with hydrogen at a temperature of about 150° C. to about 240° C. The hydrogen treatment may be conducted in combination with the sodium carbonate treatment, and may be performed prior to and/or after the sodium carbonate treatment.

Without intending to be limited by theory, it is believed that the production of hydrogen during the dehydrogenation and dimerization reaction within the process may result in contact between the conversion catalyst and a hydrogen stream sufficient to at least partially reduce the catalyst. Thus, the process described herein may have the potential for the in-situ reduction of the catalyst during use. This may result in an initial break-in period in which the catalyst conversion and selectivity may change before reaching a steady state conversion and selectivity. This in-situ reduction may be taken into account when considering the degree to which a catalyst should be pre-reduced with hydrogen.

In some embodiments, the catalyst used to produce one or more higher alcohol(s) and/or ethyl acetate comprises a multi-component catalyst: a first dehydrogenation catalyst component and a second solid base catalyst component. While not intending to be limited by theory, it is believed that the dehydrogenation catalyst component may catalyze reaction equations 2, 4 and 5 presented above, and the solid base catalyst component may catalyze reaction 4 presented above. The first component of the multi-component catalyst may comprise any of the catalysts elements described herein with respect to the hydrogenation catalysts. The second component of the multi-component catalyst may comprise any of the catalysts elements described herein with respect to the catalysts for producing one or more higher alcohols and/or any of the catalysts elements described herein with respect to the catalysts for producing higher alcohol(s) and ethyl acetate.

The relative amount of each of the first and second component may vary in the multi-component catalyst to achieve the desired dehydrogenation/hydrogenation performance. In an embodiment, the amount of the first catalyst component may generally be less than about 30% by volume, less than about 25% by volume, less than about 20% by volume, less than about 15% by volume, less than about 10% by volume, or less than about 5% by volume. The amount of the first catalyst component may be greater than about 0.1% by volume, greater than about 1% by volume, greater than about 2% by volume, greater than about 3% by volume, greater than about 4% by volume, or greater than about 5% by volume. In an embodiment, the ratio of the volume of the first catalyst component to the volume of the second catalyst component may range from about 1:2 to about 1:100, from about 1:5 to about 1:90, or from about 1:10 to about 1:80.

In an embodiment, optional components such as binders and/or supports may also be present in the multi-component catalyst. The multi-component catalyst can be employed in any of the conventional types or structures known to the art. It may be employed in the form of extrudates, pills, pellets, granules, broken fragments, or various special shapes. In an embodiment, consideration of the use of the multi-component catalyst in the reactive distillation system and/or as a mass transfer surface within the distillation column may be taken into account when determining a suitable shape. For example, the multi-component catalyst may have a shape similar to structured packing material or suitable for insertion in a structured packing. In some embodiments, the catalyst may comprise a particular material that is dispersed in the reactants.

In some embodiments, the first catalyst component that catalyzes hydrogenation-dehydrogenation could be any common hydrogenation catalyst for example Cu, Pd, Pt, $Cr_2O_3$, $PtO_2$, and/or $Cu_2Cr_2O_5$ (e.g., a Lazier catalyst). Copper may be beneficial because of its lower cost and low byproduct formation. In some embodiments, the second catalyst component of the multi-component catalyst may be one or more of MgO, $Mg(OH)_2$, magnesium carbonates and calcium phosphates (e.g. $Ca_5(OH)(PO_4)_3$, $Ca_2P_2O_7$ and other calcium phosphates), layered double hydroxide minerals either natural or synthetic such as hydrotalcite, kaolinite as well as the products of their interaction with alkaline earth oxides or hydroxides such as MgO, $Mg(OH)_2$, CaO, $Ca(OH)_2$ or their carbonates at high temperatures. Strontium and barium oxides, hydroxides and phosphates can be potentially used in the process as solid base components as well.

The activity of the second component of the multi-component catalyst was found to depend on the method of preparation. The multi-component catalyst can be prepared by any of the methods described herein for preparing a catalyst, including, but not limited to, physically mixing the two components, sol-gel co-precipitation, or loading the dehydrogenation catalyst on the base catalyst component by impregnation. Each of these methods was found to lead to the creation of active catalyst. Physical mixing may be beneficial due to its simplicity, while an impregnation process resulted in higher performance.

In an embodiment, the second catalyst component of the multi-component catalyst may comprise MgO. As illustrated in the Examples accompanying this disclosure, the activity of a catalyst comprising MgO was observed to vary depending on its source, method of preparation and pretreatment. For example, purchased MgO was found to have conversions less than about 5%, high surface area MgO (available from Nanoscale Materials Inc. of Manhattan, Kans.) was found to have conversions up to about 26%, and MgO made from hydroxide and carbonate decomposition as described herein was found to have conversions up to about 65%.

Accordingly, the present application discloses the use of reactive distillation for the production of one or more higher alcohols from one or more alpha hydrogen alcohols, wherein the higher alcohol(s) are the primary reaction product. The present application discloses the use of Guerbet reaction catalysts and other catalysts in a reactive distillation process to produce higher alcohol(s) from the alpha hydrogen alcohol(s). The present application also discloses the production of higher alcohol(s) and/or ethyl acetate from the alpha hydrogen alcohol(s) in a single reactor. The present application discloses the use of reactive distillation for the production of ethyl acetate and/or higher alcohol(s). Still further, the present application discloses the use of supported catalysts, particularly $CuO/ZrO_2$ supported on $Al_2O_3$ and $CuO/Al_2O_3$ supported on $ZrO_2$, for the production of ethyl acetate and/or the higher alcohol(s).

EXAMPLES

The disclosure having been generally described, the following examples are given as particular embodiments of the disclosure and to demonstrate the practice and advantages thereof. It is understood that the examples are given by way of illustration and are not intended to limit the specification or the claims in any manner.

Examples 1-4

Examples 1-4 relate to catalysts useful for the production of butanol, the production butanol and/or ethyl acetate, or a combination thereof in various systems and methods described in the present application.

Example 1

Wet-Impregnation Catalyst Preparation $CuO/SiO_2$, $CuO/SiO_2$—$Al_2O_3$, $CuO/ZnO$, $CuO/ZrO_2$, $CuO/SiO_2$—$ZrO_2$ and $CuO/Al_2O_3$ catalysts were prepared via impregnation of an oxide catalyst support. In a typical co-impregnation, a measured amount of $Cu(NO_3)_2.2.5H_2O$ is dissolved in an appropriate amount of de-ionized water to fill the pore volume of the support. The solution is added to the support and agitated until the liquid is fully absorbed. The impregnated support is then dried in air at 110° C., followed by calcination in air at 400 to 600° C. for 2 to 10 hours. The amount of $Cu(NO_3)_2.2.5H_2O$ can be adjusted to achieve a desired final Cu weight loading. Typical Cu loadings are between 0.5 and 50 wt %.

Example 2

Co-Impregnation and Sequential Impregnation Catalyst Preparation $CuO/ZnO/SiO_2$, $CuO/ZrO_2/SiO_2$, $CuO/MgO/SiO_2$, $CuO/CaO/SiO_2$, $CuO/SrO/SiO_2$, $CuO/BaO/SiO_2$, $CuO/ZrO_2/Al_2O_3/SiO_2$ and $CuO/Na_2O/SiO_2$ catalysts were prepared via co-impregnation and sequential impregnation of a silica catalyst support. In a typical co-impregnation, measured amounts of $Cu(NO_3)_2.2.5H_2O$ and $M(NO_3)_x.YH_2O$ (M=Zn, ZrO, Mg, Ca, Sr, Ca, Al or Na; X=1, 2, 4; Y=2-6) is dissolved in an appropriate amount of de-ionized water to fill the pore volume of the silica support. The solution is added to the silica support and stirred until well mixed. The impregnated silica is then dried in air at 110° C., followed by calcination in air at 400-600° C. for 2-10 hours. Typical catalyst loadings range from 1-50 wt % CuO and 2 to 40 wt % $M_iO_j$.

$CuO/ZnO/Al_2O_3$, $CuO/Cr_2O_3/Al_2O_3$, and $CuO/ZrO_2/Al_2O_3$ catalysts were prepared via co-impregnation of an alumina support. A sample in which Cu, Zr and Al oxides were supported on alumina ($CuO/ZrO_2/Al_2O_3/Al_2O_3$) was also prepared. In a typical co-impregnation, measured amounts of $Cu(NO_3)_2.2.5H_2O$ and $M(NO_3)_x.YH_2O$ (M=Zn, ZrO, or Cr; X=1, 2, 3; Y=6 or 9) is dissolved in an appropriate amount of de-ionized water to fill the pore volume of the alumina support. The solution is added to the alumina support and agitated until the liquid is fully absorbed. The impregnated alumina is then dried in air at 110° C., followed by calcination in air at 400-600° C. for 2-10 hours. Typical catalyst loadings range from 1 to 50 wt % CuO and 2 to 40 wt % $M_iO_j$.

$CuO/MgO/Al_2O_3/SiO_2$ and $CuO/MgO/Al_2O_3/Al_2O_3$ catalysts were prepared via co-impregnation and sequential impregnation of a silica or alumina catalyst support. In a typical co-impregnation, measured amounts of $Cu(NO_3)_2.2.5H_2O$ and $M(NO_3)_x.YH_2O$ or $M(CH_3COO)_x.YH_2O$ (M=Mg, Al; X=2, 4; Y=2-6) is dissolved in an appropriate amount of de-ionized water. The solution is added to the silica or alumina support slowly and gradually to achieve good solids distribution on the support (incipient wetting). The impregnated silica or alumina is then dried in air at 110° C., followed by calcination in air at 400-600° C. for 2-10 hours. Typical catalyst loadings range from 1-50 wt % CuO and 2 to 40 wt % $M_iO_j$. An example of final product is 1.5 wt. % Cu, 13 wt. % MgO and 2 wt. % $Al_2O_3$ on granulated silica or alumina.

Example 3

Co-Precipitation Catalyst Preparation

Mixed-metal oxide catalysts were prepared via co-precipitation from nitrate solutions. In a typical co-precipitation synthesis, a measured amount of the appropriate metal nitrates (Cu, Zn, Zr, Al, Cr, Fe, Ni, Ba) are dissolved in de-ionized water (total metal concentration range from 0.5 to 3 M). The metal-nitrate solution is then precipitated by drop-wise addition into a stirred, equal volume of 4 M aqueous NaOH at room temperature. After addition of all the metal nitrate solution, the suspension is stirred for 12 to 24 hours to ensure complete precipitation of the metal oxides. The precipitated solid is then filtered and washed with excess de-ionized water. The solids are then dried overnight at 110° C., followed by calcination at 220 to 500° C. Catalysts prepared in this manner have CuO loadings between 40 to 80 wt %. The loadings of other metal oxides range from 2 to 40 wt %.

A catalyst binder can be added to the mixed-metal oxide to impart additional mechanical strength. The metal oxide catalyst is ground to a fine powder and then stirred into a colloidal suspension of silica or alumina in water. The resulting suspension is stirred while heating at 80 to 130° C. to dryness. The resulting solid can then be either extruded or pressed, ground, and sieved to appropriate particle sizes. An alternative is to add the colloidal silica or alumina suspension to the 4 M NaOH precipitation solution prior to addition of the metal nitrate solution. Other metal salts, including acetates and carbonates can be used in place of the nitrates.

Example 4

Dehydration, Dehydrogenation, and Dimerization of Ethanol

A portion of the catalysts prepared as described in Examples 1-3 were tested in butanol synthesis reactions after being reduced in a stream of $H_2$ at a temperature between 175 and 240° C. Catalytic performance in liquid phase reactions was then determined in a batch reactor at 180-200° C. and 20-31 atm. The reactor pressure was maintained above the vapor pressure of ethanol at the operating temperature. 4 g of catalyst was used in each reaction, and the batch reactor was charged with 15 mL of ethanol.

Table 1 shows the conversion and selectivity of the catalysts in dehydration and dehydrogenation dimerization reactions conducted in a fixed bed reactor. Conversion ($X_{ethanol}$), butanol selectivity ($S_{butanol}$), and total selectivity ($S_{total}$) were calculated from the composition of the reactor effluent as $$X_{ethanol} = 100\left(\frac{n_{EtOH} - n_{EtOH,0}}{n_{EtOH,0}}\right),$$

$$S_{butanol} = 100\left(\frac{2n_{BuOH}}{n_{EtOH} - n_{EtOH,0}}\right),$$

and $$S_{total} = 100\left(\frac{2n_{EtOAc} + 2n_{BuOH} + 2n_{AcH}}{n_{EtOH} - n_{EtOH,0}}\right),$$

respectively, where $n_{EtOH}$, $n_{BuOH}$, and $n_{AcH}$ represent the molar flow rate of ethanol, butanol (e.g., n-butanol and/or 2-butanol), and acetaldehyde in the reactor effluent (e.g., the product stream comprising the butanol), respectively, and the remaining terms are the same as described above with respect to the conversion of ethanol. Acetaldehyde is an intermediate product in the reaction to make ethyl acetate (and possibly for the reaction to make butanols) and is therefore included in the total selectivity calculation.

TABLE 1

Conversion and selectivity for selected catalysts in a batch reactor operating at 200° C. and 33 atm after 4 hrs of reaction time.

| Catalyst sample | $X_{ethanol}$ | $S_{butanol}$ | $S_{total}$ |
|---|---|---|---|
| Impregnated catalysts | | | |
| CuO on Al$_2$O$_3$ | 21.0 | 9.4 | 96.7 |
| CuO/Al$_2$O$_3$ on ZrO$_2$ | 16.0 | 21.1 | 93.3 |
| CuO/Na$_2$O on SiO$_2$ | 4.8 | 10.1 | 95.9 |
| CuO/ZrO$_2$/Al$_2$O$_3$ on Al$_2$O$_3$ | 19.0 | 16.7 | 94.4 |
| CuO/ZrO$_2$/Al$_2$O$_3$ on SiO$_2$ | 13.7 | 36.5 | 74.7 |
| CuO/ZrO$_2$ on Al$_2$O$_3$ | 17.9 | 24.3 | 92.7 |
| CuO/ZrO$_2$ on SiO$_2$ | 23.3 | 14.3 | 92.4 |
| Co-precipitation catalysts | | | |
| CuO/Cr$_2$O$_3$/BaO | 20.8 | 3.8 | 98.5 |
| CuO/ZrO$_2$/Al$_2$O$_3$ | 17.8 | 2.2 | 97.7 |

From Examples 1 through 4, it can be seen that a high total selectivity to butanol and ethyl acetate can be attained using the conversion catalysts described herein. In particular, the CuO/Al$_2$O$_3$ on ZrO$_2$ and the CuO/ZrO$_2$ on Al$_2$O$_3$ catalyst preparations each can simultaneously produce ethyl acetate and butanol, attain a total selectivity above 90%, and attain a selectivity for butanol above 20%. Based on Examples 1 through 4, it can also be seen that a high total selectivity to butanol and ethyl acetate using the conversion catalysts described herein should enable the use of the system embodiments as illustrated in the Figures of the present disclosure.

Examples 5-8

Examples 5-8 relate to catalysts useful for the production of ethyl acetate in various systems and methods for coproducing butanol and ethyl acetate described in the present application. Additional information regarding the preparation of the catalysts described in Examples 5-8 can be found in U.S. patent application Ser. No. 13/363,858, which is incorporated by reference herein in its entirety.

Example 5

Wet-Impregnation Catalyst Preparation

Various catalysts including CuO/SiO$_2$, CuO/SiO$_2$—Al$_2$O$_3$, CuO/ZnO, CuO/ZrO$_2$, CuO/SiO$_2$—ZrO$_2$, CuO/ZnO/Al$_2$O$_3$, CuO/Cr$_2$O$_3$/BaO, CuO/Cr$_2$O$_3$ and CuO/Al$_2$O$_3$ were prepared via impregnation of the corresponding oxide catalyst support. The preparation involved dissolving 4 grams (g) of Cu(NO$_3$)$_2$.2.5H$_2$O in 30 mL of de-ionized water, which was then added to 30 g of the appropriate oxide support and stirred until well mixed. The impregnated support was then dried in air at 110° C., followed by calcination in air at 450° C. The amount of Cu(NO$_3$)$_2$.2.5H$_2$O was adjusted to achieve a desired final Cu weight loading. Enough water was used to wet the entire oxide support. Copper loadings between 0.5% and 20% by weight were achieved.

Example 6

Co-Impregnation and Sequential Impregnation Catalyst Preparation

Various catalysts including CuO/ZnO/SiO$_2$, CuO/ZrO$_2$/SiO$_2$, CuO/MgO/SiO$_2$, CuO/CaO/SiO$_2$, CuO/SrO/SiO$_2$, CuO/BaO/SiO$_2$, and CuO/Na$_2$O/SiO$_2$ were prepared via co-impregnation and sequential impregnation of a silica catalyst support. For the co-impregnation, measured amounts of Cu(NO$_3$)$_2$.2.5H$_2$O and M(NO$_3$)$_x$.YH$_2$O (M=Zn, ZrO, Mg, Ca, Sr, Ca, or Na; X=1, 2, 4; Y=2-6) were dissolved in de-ionized water. The solution was added to the silica support and stirred until well mixed. The impregnated silica was dried in air at 110° C., followed by calcination in air at 450° C.

For the sequential impregnation, a measured amount of M(NO$_3$)$_x$.YH$_2$O (M=Mg, Ca, Sr, Ca, or Na; X=1 or 2; Y=2-6) was dissolved in de-ionized water. The solution was then added to the silica support and mixed well. The silica was dried at 110° C. and then calcined at 450° C. in air. This procedure was then repeated using Cu(NO$_3$)$_2$.2.5H$_2$O in place of the first metal nitrate. Copper loadings between 0.5% and 20% by weight and an addition metal loading between 0.1% and 10% by weight were achieved.

Example 7

Co-Precipitation Catalyst Preparation

Mixed-metal oxide catalysts were prepared via co-precipitation from nitrate solutions. In the co-precipitation synthesis, a measured amount of the appropriate metal nitrate (Cu, Zn, Zr, Al, Cr, Fe, Ni, Ba, or any combination thereof) were dissolved in de-ionized water (total metal concentration ranges from 1-3 M). The metal-nitrate solution was then precipitated by drop-wise addition into a stirred, equal volume of 4 M aqueous NaOH at room temperature. After addition of all the metal nitrate solution, the suspension was stirred for an additional 12 to 24 hours to ensure complete precipitation of the metals. The precipitated solid was then filtered and washed with excess de-ionized water. The solids were then dried overnight at 110° C. The resulting mixed metal oxide was then pressed, ground, and sieved to recover a catalyst with particle sizes between 450 and 850 μm. Catalysts prepared in this manner had copper oxide loadings between 40% and 80% by weight. The loadings of other metal oxides ranged from 2% to 40% by weight.

In addition to the catalysts prepare above, various catalysts were prepared via co-precipitation and then a binder was incorporated. The catalyst binder was added to the mixed-metal oxide prepared as described above by first grinding the mixed-metal oxide to a fine powder and then stirring it into a colloidal suspension of silica or alumina in water. The resulting suspension was stirred while heating at 80-130° C. to dryness. The resulting solid was then be pressed, ground, and sieved to appropriate particle sizes.

Example 8

Dehydrogenative Dimerization of Ethanol

A portion of the catalysts prepared as described in Examples 5 to 7 were treated with a $Na_2CO_3$ solution by soaking the catalyst in a 0.2 M aqueous solution of $Na_2CO_3$ for 2-24 hrs. The catalyst was then filtered and allowed to dry in air at room temperature. Another portion of the catalysts prepared as described in Examples 3 to 5 were reduced in a hydrogen environment at 175-240° C. for a period of 4-12 hours. These catalysts were then tested in ethanol dehydrogenation reactions. Conversion and selectivity for gas phase reactions were determined from use in a fixed bed reactor operating at 190-240° C. and 1-24 atm. Pure ethanol was fed to the reactor with a weight hourly space velocity (WHSV) between 0.1-1.5 $hr^{-1}$. Conversion and selectivity for liquid phase and mixed liquid/vapor phase reactions were determined a fixed bed reactor, operating at 190-240° C. and at pressures above 25 atm. Liquid phase reactions were also conducted in a batch reactor at 180-200° C. and 20-31 atm (the reactor pressure was maintained above the vapor pressure of ethanol at the operating temperature).

Table 2 shows the conversion and selectivity of the catalysts in a dehydrogenative dimerization reaction conducted in a fixed bed reactor. The conversion of ethanol ($X_{ethanol}$) and "ethyl acetate selectivity" ($S_{ethyl\ acetate}$) were calculated from the composition of the reactor effluent as $$X_{ethanol} = 100 \left( \frac{F_{EtOH,0} - F_{EtOH}}{F_{EtOH,0}} \right)$$

$$S_{ethyl\ acetate} = 100 \left( \frac{2F_{EtOAc} + 2F_{AcH}}{F_{EtOH,0} - F_{EtOH}} \right)$$

where $F_{EtOH}$, $F_{EtOAc}$, and $F_{AcH}$ represent the molar flow rates of ethanol, ethyl acetate, and acetaldehyde in the reactor effluent, respectively, and $F_{EtOH,0}$ represents the molar flow rate of ethanol into the reactor inlet. Acetaldehyde is a reaction intermediate and so was included in the selectivity calculation. As used herein, the ethyl acetate selectivity of the conversion refers to the amount of ethanol that is consumed in the conversion reaction that is converted to ethyl acetate.

TABLE 2

Conversion and Selectivity for selected catalysts in a fixed bed reactor at 220° C. and 1 atm

| Catalyst sample | As prepared/received | | Reduced in $H_2$ | |
| --- | --- | --- | --- | --- |
| | X | S | X | S |
| Pellet catalysts | | | | |
| $CuO/ZnO/Al_2O_3$ | 18.9 | 92.4 | 35.0 | 89.7 |
| $CuO/Cr_2O_3/BaO$ | 43.5 | 89.4 | 36.0 | 74.6 |
| Impregnated catalysts | | | | |
| $CuO/SiO_2$ | 19.6 | 96.2 | 22.5 | 80.9 |
| $CuO/SiO_2$—$Al_2O_3$ | 43.0 | 17.0 | | |
| $CuO/Al_2O_3$ | 50.2 | 47.3 | | |
| $CuO/ZnO$ | 19.7 | 65.5 | | |
| $CuO/ZrO_2$ | 41.5 | 63.4 | | |
| $CuO/SiO_2$—$ZrO_2$ | 40.0 | 59.7 | | |

TABLE 2-continued

Conversion and Selectivity for selected catalysts in a fixed bed reactor at 220° C. and 1 atm

| Catalyst sample | As prepared/received | | Reduced in $H_2$ | |
| --- | --- | --- | --- | --- |
| | X | S | X | S |
| $CuO/MgO/SiO_2$ | 37.9 | 70.0 | 32.1 | 65.7 |
| $CuO/CaO/SiO_2$ | 33.3 | 73.4 | 29.0 | 42.7 |
| $CuO/SrO/SiO_2$ | 25.1 | 77.2 | 31.5 | 69.6 |
| $CuO/BaO/SiO_2$ | 31.0 | 73.2 | 33.6 | 73.6 |
| $CuO/Na_2O/SiO_2$ | 19.4 | 95.9 | | |
| $CuO/ZrO_2/SiO_2$ | 39.1 | 58.7 | 54.0 | 61.6 |
| Co-precipitation catalysts | | | | |
| $CuO/ZnO/ZrO_2/Al_2O_3$ | 8.7 | 83.6 | 21.4 | 72.6 |
| $CuO/ZnO/ZrO_2/Al_2O_3/Na_2CO_3$ | 26.1 | 40.1 | 39.0 | 86.1 |
| $CuO/ZnO/ZrO_2/Cr_2O_3$ | 28.8 | 92.0 | 20.9 | 80.9 |
| $CuO/ZnO/ZrO_2/Cr_2O_3/Na_2CO_3$ | 37.0 | 90.2 | 35.9 | 87.5 |
| $CuO/ZnO/ZrO_2/Fe_2O_3$ | 34.1 | 92.1 | 17.0 | 94.2 |
| $CuO/ZnO/ZrO_2/Fe_2O_3/Na_2CO_3$ | 30.7 | 72.6 | | |
| $CuO/ZnO/ZrO_2/Al_2O_3/Cr_2O_3$ | 24.5 | 88.4 | 18.5 | 79.4 |
| $CuO/ZnO/ZrO_2/Al_2O_3/Cr_2O_3/Na_2CO_3$ | 33.2 | 86.3 | | |

Example 9

Conversion of Ethanol to n-Butanol Using a Ca-Pyrophosphate/Cu Catalyst

A catalyst was prepared by mixing 8 grams of $Ca_2P_2O_7$ with 0.2 g CuO as powders. The catalyst was treated with hydrogen at 220° C. The catalyst (8 grams catalyst) was placed in contact with ethanol at a flow rate of 0.04 ml/min at 260° C. in presence of 15.4 ml/min. co-fed hydrogen. The reaction was for carried out for 4 hours. The observed conversion was calculated to be about 15% and the resulting selectivities are listed in Table 3.

TABLE 3

Selectivities for example 9

| Compound | Selectivity, wt. % |
| --- | --- |
| Acetaldehyde | 27 |
| Acetone | 1.3 |
| 2-Propanol | 0.5 |
| Butyraldehyde | 5.2 |
| 2-Butanone | 1.1 |
| Ethyl Acetate | 0.7 |
| 2-Butanol | 0.5 |
| 1-Butanol | 49.2 |
| 2-Pentanone | 3.7 |
| Ethyl Butyrate | 2.1 |
| Butyl Acetate | 0.7 |
| 4-Hydroxy-2-butanone | 4.6 |
| 1,2-Butanediol | 2.5 |

Example 10

Conversion of Ethanol to n-Butanol Using a Nanoparticulate MgO/Cu Catalyst

A catalyst was prepared by mixing 8 grams of nanoparticulate Nanoactive®MgO (sourced from Nanoscale Materials Corp. of Manhattan, Kans.) with 0.2 grams CuO as powders. The catalyst was treated with hydrogen at 220° C. The catalyst (8 grams catalyst) was placed in contact with ethanol at a flow rate of 0.04 ml/min at 300° C. in the presence of 15.4 ml/min. co-fed hydrogen. The reaction was carried out for 4 hours. The observed conversion was calculated to be about 26% and the resulting selectivities are listed in Table 4.

TABLE 4

Selectivities for example 10

| Compound | Selectivity, wt. % |
|---|---|
| Acetaldehyde | 15.1 |
| Acetone | 2.1 |
| 2-Propanol | 2 |
| Butyraldehyde | 3.6 |
| 2-Butanone | 2.7 |
| Ethyl Acetate | 0.5 |
| 2-Butanol | 2.1 |
| 1-Butanol | 60.9 |
| 2-Pentanone | 8.9 |
| Ethyl Butyrate | 2.1 |
| Butyl Acetate | 0 |
| 4-Hydroxy-2-butanone | 0 |
| 1,2-Butanediol | 0 |

Example 11

Conversion of Ethanol to n-Butanol Using Synthetic Hydrotalcite/Cu Catalyst

A catalyst was prepared by mixing 8 grams of synthetic hydrotalcite with 0.2 grams CuO as powders. The catalyst was treated with hydrogen at 220° C. The catalyst (8 grams catalyst) was placed in contact with ethanol at a flow rate of 0.04 ml/min at 260° C. in the presence of 15.4 ml/min co-fed hydrogen. The reaction was carried out for 4 hours. The observed conversion was calculated to be about 2% and the resulting selectivities are listed in Table 5.

TABLE 5

Selectivities for example 11

| Compound | Selectivity, wt. % |
|---|---|
| Acetaldehyde | 71 |
| Acetone | 0 |
| 2-Propanol | 0 |
| Butyraldehyde | 0 |
| 2-Butanone | 0 |
| Ethyl Acetate | 2.1 |
| 2-Butanol | 0 |
| 1-Butanol | 26.9 |
| 2-Pentanone | 0 |
| Ethyl Butyrate | 0 |
| Butyl Acetate | 0 |
| 4-Hydroxy-2-butanone | 0 |
| 1,2-Butanediol | 0 |

Example 12

Conversion of Ethanol to n-Butanol Using a Mg(OH)$_2$/Cu Catalyst

A catalyst was prepared by mixing 9 grams of Mg(OH)$_2$ with 0.5 grams of CuO as powders. The catalyst was treated with hydrogen at 220° C. The catalyst (8 grams catalyst) was placed in contact with ethanol at a flow rate of 0.04 ml/min at 300° C. without a co-feed of hydrogen. The reaction was carried out for 4 hours. The observed conversion was calculated to be about 64% and the resulting selectivities are listed in Table 6.

TABLE 6

Selectivity for example 12

| Compound | Selectivity, wt. % |
|---|---|
| Acetaldehyde | 57.3 |
| Acetone | 2.4 |
| 2-Propanol | 0 |
| Butyraldehyde | 21.4 |
| 2-Butanone | 0.5 |
| Ethyl Acetate | 0.9 |
| 2-Butanol | 0 |
| 1-Butanol | 13.7 |
| 2-Pentanone | 2.5 |
| Ethyl Butyrate | 1.2 |
| Butyl Acetate | 0 |
| 4-Hydroxy-2-butanone | 0 |
| 1,2-Butanediol | 0 |

Example 13

Conversion of Ethanol to n-Butanol Using a Ca(OH)$_2$ Treated Synthetic Hydrotalcite/Cu Catalyst The catalyst was prepared by mixing 9 grams Ca-hydroxide treated synthetic hydrotalcite with 0.6 grams CuO as powders. The Ca-hydroxide treated hydrotalcite was prepared by mixing a slurry of 3 grams of Ca(OH)$_2$ in 30 ml of water with 20 grams of synthetic hydrotalcite. The mixture was then heated to dryness followed by heating to 300° C. for 2 hours. The catalyst was treated with hydrogen at 220° C.

The catalyst (8 grams catalyst) was placed in contact with ethanol at a flow rate of 0.04 ml/min at 300° C. without a co-feed of hydrogen. The reaction was carried out for 4 hours. The observed conversion was calculated to be about 58% and the resulting selectivities are listed in Table 7.

TABLE 7

Selectivity for example 13

| Compound | Selectivity, wt. % |
|---|---|
| Acetaldehyde | 45.6 |
| Acetone | 1.6 |
| 2-Propanol | 0 |
| Butyraldehyde | 27.2 |
| 2-Butanone | 0 |
| Ethyl Acetate | 1.7 |
| 2-Butanol | 0 |
| 1-Butanol | 21.2 |
| 2-Pentanone | 1.4 |
| Ethyl Butyrate | 0.8 |
| Butyl Acetate | 0 |
| 4-Hydroxy-2-butanone | 0 |
| 1,2-Butanediol | 0 |

Example 14

Conversion of Ethanol to n-Butanol Using a MgO (from Magnesium Basic Carbonate)/Cu Catalyst The catalyst was prepared by mixing 9 grams of MgO prepared from Mg basic carbonate (available from Fisher Scientific of Waltham, Mass.) with 1 gram of CuO as powders. The MgO was prepared by heating commercially available MgCO$_3$.Mg(OH)$_2$ to 450° C. at a heating rate of about 1° C./min. The mixture was held at 450° C. for 2 hours. mixed MgO and CuO catalyst was treated with hydrogen at 220° C.

The catalyst (8 grams catalyst) was placed in contact with ethanol at a flow rate of 0.04 ml/min at 260° C. without a co-feed of hydrogen. The reaction was carried out for 4 hours. The observed conversion was calculated to be about 52% and the resulting selectivities are listed in Table 8.

TABLE 8

Selectivity for example 14

| Compound | Selectivity, wt. % |
|---|---|
| Acetaldehyde | 38.3 |
| Acetone | 1.3 |
| 2-Propanol | 0 |
| Butyraldehyde | 21.2 |
| 2-Butanone | 0.5 |
| Ethyl Acetate | 2.8 |
| 2-Butanol | 0 |
| 1-Butanol | 31.8 |
| 2-Pentanone | 1.7 |
| Ethyl Butyrate | 2.1 |
| Butyl Acetate | 0 |
| 4-Hydroxy-2-butanone | 0 |
| 1,2-Butanediol | 0 |

Example 15

Conversion of Ethanol to n-Butanol Using a MgO (from Magnesium Hydroxide)/Cu Catalyst The catalyst was prepared by mixing 9 grams of MgO prepared from Mg hydroxide (available from Fisher scientific of Waltham, Mass.) with 1 gram of CuO as powders. The MgO was prepared by heating the $Mg(OH)_2$ in an open crucible to 450° C. at a heating rate of about 1° C./min. The $Mg(OH)_2$ was held at 450° C. for about 2 hours. The mixed MgO and CuO catalyst was treated with hydrogen at 220° C.

The catalyst (8 grams catalyst) was placed in contact with ethanol at a flow rate of 0.04 ml/min at 300° C. without a co-feed of hydrogen. The reaction was carried out for 4 hours. The observed conversion was calculated to be about 56% and the resulting selectivities are listed in Table 9.

TABLE 9

Selectivity for example 15

| Compound | Selectivity, wt. % |
|---|---|
| Acetaldehyde | 38.7 |
| Acetone | 1.1 |
| 2-Propanol | 0 |
| Butyraldehyde | 27.5 |
| 2-Butanone | 0.5 |
| Ethyl Acetate | 0.6 |
| 2-Butanol | 0 |
| 1-Butanol | 25.1 |
| 2-Pentanone | 2.1 |
| Ethyl Butyrate | 0.8 |
| Butyl Acetate | 0 |
| 4-Hydroxy-2-butanone | 2.3 |
| 1,2-Butanediol | 1.2 |

Example 16

Conversion of Ethanol to n-Butanol Using a MgO (from Magnesium Hydroxide)/Cu Catalyst Loaded Through a Cu-Salt Precursor The catalyst was prepared by gradually mixing 10 grams of MgO prepared from Mg hydroxide (available from Fisher scientific of Waltham, Mass.) with 1.5 grams of Cu-acetate hydrate as ethanol solution. Once all of the acetate salt was transferred and the ethanol was evaporated, the material was heated to 415° C. to generate the final catalyst. The MgO used in the mixture was prepared by heating $Mg(OH)_2$ in a crucible to 450° C. at a heating rate of about 1° C./min and holding the $Mg(OH)_2$ at 450° C. for 2 hours. The mixed catalyst was treated with hydrogen at 220° C.

The catalyst (8 grams catalyst) was placed in contact with ethanol at a flow rate of 0.04 ml/min at 260° C. without a co-feed of hydrogen. The reaction was carried out for 4 hours. The observed conversion was calculated to be about 55% and the resulting selectivities are listed in Table 10.

TABLE 10

Selectivity for example 16

| Compound | Selectivity, wt. % |
|---|---|
| Acetaldehyde | 53.3 |
| Acetone | 1.2 |
| 2-Propanol | 0 |
| Butyraldehyde | 23.9 |
| 2-Butanone | 0 |
| Ethyl Acetate | 1 |
| 2-Butanol | 0 |
| 1-Butanol | 17.4 |
| 2-Pentanone | 1.7 |
| Ethyl Butyrate | 0.9 |
| Butyl Acetate | 0 |
| 4-Hydroxy-2-butanone | 0 |
| 1,2-Butanediol | 0 |

Example 17

Direct Synthesis of Higher Alcohols from Ethanol

Catalysts were tested for higher alcohol synthesis reactions in a fixed bed reactor operating at about 200-300° C. and about 1-35 atm. Catalysts were reduced in a stream of $H_2$ at a temperature between 175° C. and 240° C. prior to use in reactions.

Table 11 shows the reactor effluent composition using two different supported catalysts at different temperatures. The first catalyst was a mixture of CuO and MgO co-impregnated onto a $SiO_2$ support and the second was CuO, $ZrO_2$ and $Al2O_3$ co-impregnated onto an $Al_2O_3$ support. The reactor effluent composition shown in Table 11 resulted from the use of 5.0 g catalyst with a 0.10 ml/min ethanol feed at 500 psig. As expected, increasing temperature also increased the conversion of ethanol to higher alcohols. Significant amounts of acetaldehyde and butyraldehyde were also observed, but no crotonaldehyde was observed in the reactor effluent. In Table 11, the "hexanols" include both 1-hexanol and 2-ethyl butanol, and the "octanols" include 1-octanol and 2-ethyl hexanol.

TABLE 11

| Catalyst | Temperature (° C.) | Effluent Composition (wt %) | | | |
|---|---|---|---|---|---|
| | | Ethanol | 1-Butanol | Hexanols | Octanols |
| CuO/ MgO on $SiO_2$ | 240 | 88.8 | 4.3 | 1.8 | 1.1 |
| | 260 | 85.4 | 6.3 | 1.9 | 0.8 |
| | 280 | 76.9 | 12.3 | 2.6 | 1.1 |
| | 300 | 68.4 | 14.8 | 4.2 | 1.2 |
| $CuO/ZrO_2$/ $Al_2O_3$ on | 220 | 90.2 | 5.3 | 1.3 | 0.5 |
| | 240 | 84.6 | 8.2 | 2.2 | 0.8 |

TABLE 11-continued

| Catalyst | Temperature (° C.) | Effluent Composition (wt %) | | | |
|---|---|---|---|---|---|
| | | Ethanol | 1-Butanol | Hexanols | Octanols |
| $Al_2O_3$ | 260 | 78.8 | 11.1 | 2.7 | 0.9 |
| | 280 | 56.3 | 19.9 | 7.0 | 2.2 |
| | 300 | 43.0 | 23.0 | 10.1 | 3.5 |

Figure 13:
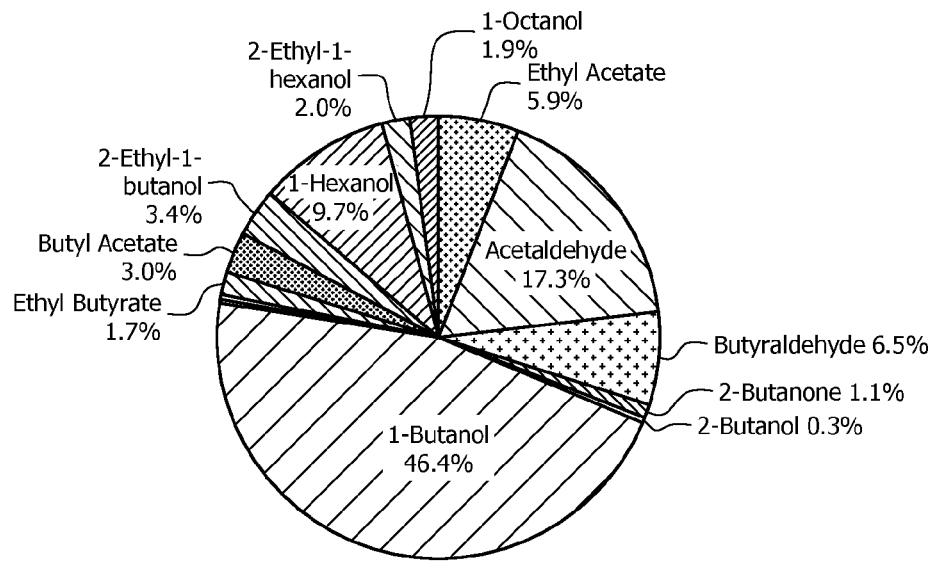
FIG. 13 illustrates a product distribution of higher alcohols according to an embodiment.
Figure 14:
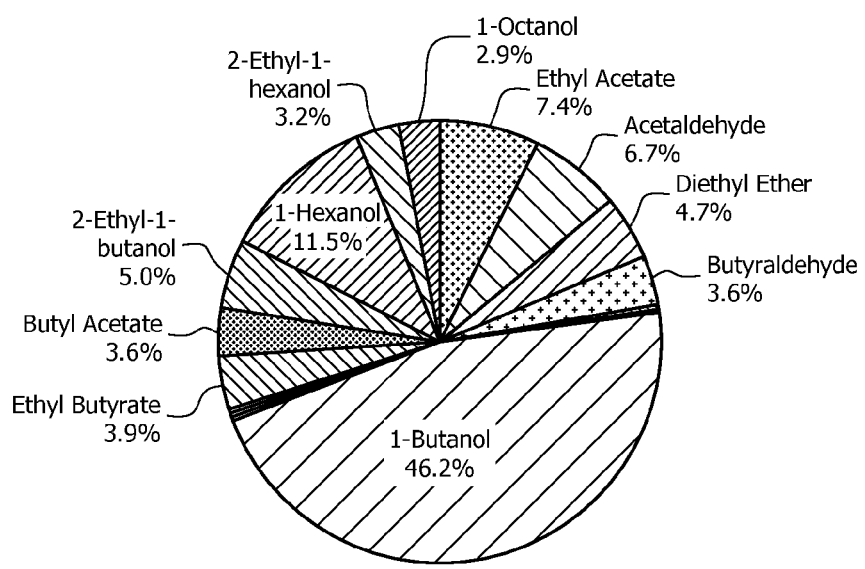
FIG. 14 illustrates another product distribution of higher alcohols according to an embodiment.

FIG. 13 shows a typical product distribution from the CuO/MgO on $SiO_2$ catalyst. Including the intermediates acetaldehyde and butyraldehyde along with all of the product alcohols, the overall reaction selectivity is above 85% (the percent of the total ethanol consumed that is converted into the desired product or reaction intermediates). Other reaction products include mostly esters such as ethyl acetate, butyl acetate, and ethyl butyrate, although some 2-butanone and 2-butanol are also present in the reactor effluent. The product distribution using the $CuO/ZrO_2/Al_2O_3$ on $Al_2O_3$ catalyst, shown in FIG. 14, displays a similar breakdown of reaction byproducts, except a significant amount of diethyl ether is produced over this catalyst.

Example 18

Direct Synthesis of Higher Alcohols from Ethanol

The catalyst was prepared by mixing 10.7 grams of Mg-acetate.$4H_2O$ with 0.6 gram of $Al(OH)(OAc)_2$ and 0.6 g Cu-acetate hydrate. The solids were dissolved in ~150 ml de-ionized water with the addition of 10 ml glacial acetic acid. The solution was loaded on either 15 g Saint Gobain 61138 silica(A) or 15 g WR Grace 2720 alumina(B). The resulted loaded supports were heated to 350° C. at 1° C./min and held at 350° C. for 3 h. The resulting catalysts (5 grams each catalyst) were placed in contact with ethanol at a flow rate of 0.1 ml/min at 260° C. without a co-feed of hydrogen at a pressure of 500 psig. The reaction was carried out for 2 hours. The observed conversion for (A) was calculated to be about 30% and the resulting selectivity is listed in Table 12.

TABLE 12

Selectivity for example 17A

| Compound | Selectivity, wt. % |
|---|---|
| Acetaldehyde | 10.4 |
| Acetone | 0 |
| 2-Propanol | 0 |
| Butyraldehyde | 3.7 |
| 2-Butanone | 1 |
| Ethyl Acetate | 6.8 |
| 2-Butanol | 0 |
| 1-Butanol | 51.9 |
| 2-Pentanone | 1.7 |
| Ethyl Butyrate | 2.8 |
| Butyl Acetate | 2.4 |
| 2-ethyl-1-butanol | 5.5 |
| 1-hexanol | 10.7 |
| 2-ethyl-1-hexanol | 2.4 |
| 1-ocatnol | 1.3 |

When loaded on WR Grace alumina the observed conversion was 31% with observed product distribution selectivity listed in Table 13.

TABLE 13

Selectivity for example 17B

| Compound | Selectivity, wt. % |
|---|---|
| Acetaldehyde | 7.7 |
| Acetone | 0 |
| 2-Propanol | 0 |
| Butyraldehyde | 3.5 |
| 2-Butanone | 0.5 |
| Ethyl Acetate | 9.7 |
| 2-Butanol | 0 |
| 1-Butanol | 55.5 |
| 2-Pentanone | 0 |
| Ethyl Butyrate | 3.6 |
| Butyl Acetate | 2.4 |
| 2-ethyl-1-butanol | 3.2 |
| 1-hexanol | 9.6 |
| 2-ethyl-1-hexanol | 1.7 |
| 1-ocatnol | 1.4 |

Having described numerous systems and methods herein, various embodiments of can include, but are not limited to:

In a first embodiment, a reactive distillation method comprises introducing a feed stream to a reactive distillation column, wherein the feed stream comprises ethanol; contacting the feed stream with a catalyst in the reactive distillation column during a distillation, wherein the feed stream reacts in the presence of the catalyst to produce a reaction product comprising butanol and water; removing butanol during the distillation from the reactive distillation column as a bottoms stream; and removing water during the distillation from the reactive distillation column as an overhead stream.

A second embodiment may include the reactive distillation method of the first embodiment, further comprising: contacting the bottoms stream with a hydrogenation catalyst and hydrogen to hydrogenate at least a portion of a contaminant in the bottoms stream; and separating the hydrogenated portion of the contaminant from the bottoms stream.

A third embodiment may include the reactive distillation method of the second embodiment, wherein the hydrogenation catalyst comprises a Group VIII metal, a Group VI metal, or any combination thereof.

A fourth embodiment may include the reactive distillation method of any of the first to third embodiments, wherein the catalyst comprises a catalyst capable of carrying out a dehydration and dimerization reaction.

A fifth embodiment may include the reactive distillation method of any of the first to fourth embodiments, wherein the catalyst comprises a Guerbet reaction catalyst, a solid base multicomponent oxide catalyst, a solid acid/base bifunctional catalyst, a zeolite with alkali counterions, a magnesium oxide catalyst, an oxide powder catalyst, or any combination thereof.

A sixth embodiment may include the reactive distillation method of any of the first to fifth embodiments, wherein the catalyst comprises a hydroxyapatite Guerbet reaction catalyst, a solid base Guerbet reaction catalyst, or a combination thereof.

A seventh embodiment may include the reactive distillation method of any of the first to sixth embodiments, wherein the catalyst comprises nickel, nickel oxide supported on alumina, or a combination thereof.

An eighth embodiment may include the reactive distillation method of the seventh embodiment, wherein the catalyst has a nickel weight loading of between about 2% and about 20% of the catalyst.

A ninth embodiment may include the reactive distillation method of any of the first to eighth embodiments, wherein the catalyst comprises a catalyst component represented by the formula: M/MgO/Al$_2$O$_3$, wherein M represents palladium, rhodium, nickel, or copper, or oxides thereof.

A tenth embodiment may include the reactive distillation method of any of the first to ninth embodiments, wherein the catalyst comprises a hydroxyapatite represented by the formula: Ca$_{10}$(PO$_4$)$_6$(OH)$_2$, wherein the ratio of calcium to phosphorus (Ca:P) is between about 1.5 and about 1.8.

An eleventh embodiment may include the reactive distillation method of any of the first to tenth embodiments, wherein the catalyst comprises an apatite structure satisfying the formula: M$_a$(M'O$_b$)$_c$X$_2$, wherein M represents calcium, strontium, magnesium, barium, lead, cadmium, iron, cobalt, nickel, zinc, or hydrogen, wherein M' represents phosphorus, vanadium, arsenic, carbon, or sulfur, wherein X represents a fluorine, chlorine, bromine, or a hydroxide, and wherein a is about 10, b is about 3, c is about 6, and the ratio of a to c is between about 1.5 and about 1.8.

A twelfth embodiment may include the reactive distillation method of any of the first to eleventh embodiments, wherein the catalyst comprises a calcium phosphate, a calcium phosphate carbonate, a calcium pyrophosphate, a magnesium phosphate, a magnesium phosphate carbonate, a magnesium pyrophosphate or any combination thereof.

A thirteenth embodiment may include the reactive distillation method of any of the first to twelfth embodiments, wherein the catalyst comprises magnesium oxide, magnesium hydroxide, magnesium phosphate hydrate (Mg$_3$(PO$_4$)$_2$.8H$_2$O), calcium oxide, calcium hydroxide, calcium fluoride, calcium silicate (wollastonite), calcium sulfate dihydrate (gypsum), lithium phosphate, aluminum phosphate, titanium dioxide, fluorapatite (Ca$_{10}$(PO$_4$)$_6$F$_2$), tetracalcium phosphate (Ca$_4$(PO$_4$)$_2$O), hydrotalcite, talc, kaolin, sepiolite, or any combination thereof.

A fourteenth embodiment may include the reactive distillation method of any of the first to thirteenth embodiments, wherein the catalyst comprises at least one catalytic component selected from the group consisting of: copper, copper oxide, barium, barium oxide, ruthenium, ruthenium oxide, rhodium, rhodium oxide, platinum, platinum oxide, palladium, palladium oxide, rhenium, rhenium oxide, silver, silver oxide, cadmium, cadmium oxide, zinc, zinc oxide, zirconium, zirconium oxide, gold, gold oxide, thallium, thallium oxide, magnesium, magnesium oxide, manganese, manganese oxide, aluminum, aluminum oxide, chromium, chromium oxide, nickel, nickel oxide, iron, iron oxide, molybdenum, molybdenum oxide, sodium, sodium oxide, sodium carbonate, strontium, strontium oxide, tin, tin oxide, and any mixture thereof.

A fifteenth embodiment may include the reactive distillation method of any of the first to fourteenth embodiments, wherein the catalyst comprises a support, wherein the support comprises at least one support material selected from the group consisting of: carbon, silica, silica-alumina, alumina, zirconia, titania, ceria, vanadia, nitride, boron nitride, heteropolyacids, hydroxyapatite, zinc oxide, chromia, a zeolite, a carbon nanotube, carbon fullerene, and any combination thereof.

A sixteenth embodiment may include the reactive distillation method of any of the first to fifteenth embodiments, wherein the catalyst comprises copper, and wherein the catalyst has a copper weight loading of between about 0.5% and about 80% of the catalyst.

A seventeenth embodiment may include the reactive distillation method of any of the first to sixteenth embodiments, wherein the catalyst comprises sodium carbonate.

An eighteenth embodiment may include the reactive distillation method of any of the first to seventeenth embodiments, wherein the catalyst is at least partially reduced in the presence of hydrogen.

A nineteenth embodiment may include the reactive distillation method of any of the first to eighteenth embodiments, wherein a conversion of ethanol in the feed stream to butanol is at least about 10%.

A twentieth embodiment may include the reactive distillation method of any of the first to nineteenth embodiments, wherein a selectivity of the conversion of ethanol to butanol is at least about 15%.

A twenty first embodiment may include the reactive distillation method of any of the first to twentieth embodiments, wherein the catalyst comprises a multi-component catalyst.

A twenty second embodiment may include the reactive distillation method of the twenty first embodiment, wherein the multi-component catalyst comprises a first catalyst component and a second catalyst component, wherein the first catalyst component comprises a dehydrogenation catalyst component, and wherein the second catalyst component is configured to convert at least a portion of the ethanol in the feed stream into the reaction product comprising butanol and water.

A twenty third embodiment may include the reactive distillation method of the twenty second embodiments, wherein the first catalyst component comprises less than about 30% by volume of the combined volume of the first catalyst component and the second catalyst component.

A twenty fourth embodiment may include the reactive distillation method of the twenty second or twenty third embodiment, wherein the first catalyst component comprises Cu, Pd, Pt, Cr$_2$O$_3$, PtO$_2$, Cu$_2$Cr$_2$O$_5$, any salt thereof, or any oxide thereof.

A twenty fifth embodiment may include the reactive distillation method of any of the twenty second to twenty fourth embodiments, wherein the second catalyst component comprises magnesium oxide, magnesium hydroxide, magnesium phosphate hydrate (Mg$_3$(PO$_4$)$_2$.8H$_2$O), calcium oxide, calcium hydroxide, calcium fluoride, calcium silicate (wollastonite), calcium sulfate dihydrate (gypsum), lithium phosphate, aluminum phosphate, titanium dioxide, fluorapatite (Ca$_{10}$(PO$_4$)$_6$F$_2$), tetracalcium phosphate (Ca$_4$(PO$_4$)$_2$O), hydrotalcite, talc, kaolin, sepiolite, or any combination thereof.

A twenty sixth embodiment may include the reactive distillation method of any of the first to twenty fifth embodiments, further comprising: removing a side stream from the reactive distillation column; contacting the side stream with a second catalyst, wherein the side stream reacts in the presence of the second catalyst to produce butanol; and reintroducing the butanol produced in the presence of the second catalyst to the reactive distillation column.

A twenty seventh embodiment may include the reactive distillation method of the twenty sixth embodiment, wherein the catalyst comprises a butanol conversion catalyst suitable for use with a feed of ethanol and water and the second catalyst comprises a butanol conversion catalyst suitable for use with a feed of pure or substantially pure ethanol.

A twenty eighth embodiment may include the reactive distillation method of the twenty sixth embodiment, wherein the catalyst comprises a butanol conversion catalyst suitable for use with a feed of pure or substantially pure ethanol and the second catalyst comprises a butanol conversion catalyst suitable for use with a feed of ethanol and water.

A twenty ninth embodiment may include the reactive distillation method of any of the twenty sixth to twenty eighth embodiments, further comprising: adjusting a flow rate of the side stream to maximize butanol production.

A thirtieth embodiment may include the reactive distillation method of any of the twenty sixth to twenty ninth embodiments, further comprising: adjusting a flow rate of the side stream in response to a change in feed composition.

A thirty first embodiment may include the reactive distillation method of any of the first to thirtieth embodiments, wherein a liquid portion of the feed stream reacts in the presence of the catalyst to produce a reaction product comprising butanol and water.

A thirty second embodiment may include the reactive distillation method of any of the first to thirty first embodiments, further comprising introducing a second feed stream comprising hydrogen to the reactive distillation column.

In a thirty third embodiment, a reactive distillation system comprises a reactive distillation column comprising: a catalyst located generally centrally in the column, an ethanol feed in fluid communication with the reactive distillation column and configured to pass ethanol over the catalyst, wherein the catalyst is configured to convert at least a portion of the ethanol feed into butanol in the reactive distillation column; an overhead product water removal passage, and a bottoms product butanol removal passage; a product separation system comprising an inlet configured to receive the bottoms product from the reactive distillation column, a butanol product removal passage, and an ethanol removal passage; and a recycle line coupling the ethanol removal passage from the product separation system and an inlet to the reactive distillation column.

A thirty fourth embodiment may include the reactive distillation system of the thirty third embodiment, further comprising a hydrogenation catalyst positioned to contact a liquid product following passage over the catalyst.

A thirty fifth embodiment may include the reactive distillation system of the thirty third or thirty fourth embodiment, wherein the product separation system further comprises at least one of a lights product removal passage or a heavies product removal passage.

A thirty sixth embodiment may include the reactive distillation system of the thirty third embodiment, wherein the reactive distillation column comprises a batch reactor configured to contact a liquid ethanol feed with the catalyst and remove water during the contacting of the liquid ethanol feed with the catalyst.

A thirty seventh embodiment may include the reactive distillation system of the thirty third embodiment, wherein the reactive distillation column comprises a continuous stirred-tank reactor (CSTR) configured to contact a liquid ethanol feed with the catalyst and remove water during the contacting of the liquid ethanol feed with the catalyst.

A thirty eighth embodiment may include the reactive distillation method of any of the thirty third to thirty seventh embodiments, further comprising introducing a second feed stream comprising hydrogen to the reactive distillation column.

A thirty ninth embodiment may include the reactive distillation method of any of the thirty third to thirty eighth embodiments, wherein the catalyst comprises a multi-component catalyst, wherein the multi-component catalyst comprises a first catalyst component and second catalyst component, wherein the first catalyst component comprises a dehydrogenation catalyst component, and wherein the second catalyst component is configured to convert at least a portion of the ethanol in the feed stream into the reaction product comprising butanol and water.

In a fortieth embodiment, a reactive distillation method comprises introducing a feed stream to a reactive distillation column, wherein the feed stream comprises ethanol; contacting the feed stream with a catalyst in the reactive distillation column during a distillation, wherein the feed stream reacts in the presence of the catalyst to produce a reaction product comprising butanol and water; separating a bottoms stream during the distillation from the reactive distillation column, wherein the bottoms stream comprises butanol and ethanol; separating a recycle stream from the bottoms stream, wherein the recycle stream comprises at least a portion of the ethanol from the bottoms stream; and recycling the recycle stream to the reactive distillation column.

A forty first embodiment may include the reactive distillation method of the fortieth embodiment, further comprising introducing a second feed stream comprising hydrogen to the reactive distillation column.

In a forty second embodiment, a reactive distillation method comprises introducing a first feed stream to a reactive distillation column, wherein the first feed stream comprises ethanol; contacting the feed stream with a catalyst in the reactive distillation column during a distillation, wherein the feed stream reacts in the presence of the catalyst to produce a reaction product comprising butanol, ethyl acetate, water, and hydrogen; removing butanol and ethyl acetate during the distillation from the column as a bottoms product stream; and removing water and hydrogen during the distillation from the column as an overhead product stream.

A forth third embodiment may include the reactive distillation method of the forty second embodiment, wherein the feed stream further comprises water.

A forty fourth embodiment may include the reactive distillation method of the forty second or forty third embodiment, wherein a ratio of butanol to ethyl acetate in the bottoms product stream is increased by increasing a ratio of ethanol to water in the feed stream.

A forty fifth embodiment may include the reactive distillation method of any of the forty second to forty fourth embodiments, further comprising introducing a second feed stream comprising hydrogen to the reactive distillation column.

A forty sixth embodiment may include the reactive distillation method of the forty fifth embodiment, wherein a ratio of butanol to ethyl acetate in the bottoms product stream is decreased by increasing a ratio of ethanol to hydrogen in the feed streams.

A forty seventh embodiment may include the reactive distillation method of any of the forty second to forty sixth embodiments, further comprising introducing the bottoms product stream to a second distillation column to separate the ethyl acetate and from the butanol.

A forty eighth embodiment may include the reactive distillation method of any of the forty second to forty seventh embodiments, further comprising: contacting the bottoms stream with a hydrogenation catalyst and hydrogen to hydrogenate at least a portion of a contaminant in the bottoms stream; and separating the hydrogenated portion of the contaminant from the bottoms stream.

A forty ninth embodiment may include the reactive distillation method of the forty eighth embodiment, wherein the hydrogenation catalyst comprises a Group VIII metal, a Group VI metal, or any combination thereof.

A fiftieth embodiment may include the reactive distillation method of any of the forty second to forty ninth embodiments, wherein the catalyst comprises a catalyst capable of carrying out a dehydration and dimerization reaction, a dehydrogenation and dimerization reaction, or a combination thereof.

A fifty first embodiment may include the reactive distillation method of any of the forty second to fiftieth embodiments, wherein the catalyst comprises at least one catalytic component selected from the group consisting of: copper, copper oxide, barium, barium oxide, ruthenium, ruthenium oxide, rhodium, rhodium oxide, platinum, platinum oxide, palladium, palladium oxide, rhenium, rhenium oxide, silver, silver oxide, cadmium, cadmium oxide, zinc, zinc oxide, zirconium, zirconium oxide, gold, gold oxide, thallium, thallium oxide, magnesium, magnesium oxide, manganese, manganese oxide, aluminum, aluminum oxide, chromium, chromium oxide, nickel, nickel oxide, iron, iron oxide, molybdenum, molybdenum oxide, sodium, sodium oxide, sodium carbonate, strontium, strontium oxide, tin, tin oxide, and any mixture thereof.

A fifty second embodiment may include the reactive distillation method of any of the forty second to fifty first embodiments, wherein the catalyst comprises a support, wherein the support comprises at least one support material selected from the group consisting of: carbon, silica, silica-alumina, alumina, zirconia, titania, ceria, vanadia, boron nitride, heteropolyacids, hydroxyapatite, zinc oxide, chromia, a zeolite, a carbon nanotube, carbon fullerene, and any combination thereof.

A fifty third embodiment may include the reactive distillation method of any of the forty second to fifty second embodiments, wherein the catalyst comprises $CuO/SiO_2$, $CuO/SiO_2$—$Al_2O_3$, $CuO/ZnO$, $CuO/ZrO_2$, $CuO/SiO_2$—$ZrO_2$, $CuO/Al_2O_3$, or any combination thereof.

A fifty fourth embodiment may include the reactive distillation method of any of the forty second to fifty third embodiments, wherein the catalyst comprises $CuO/ZnO/SiO_2$, $CuO/ZrO_2/SiO_2$, $CuO/MgO/SiO_2$, $CuO/CaO/SiO_2$, $CuO/SrO/SiO_2$, $CuO/BaO/SiO_2$, $CuO/ZrO_2/Al_2O_3/SiO_2$, $CuO/Na_2O/SiO_2$, or any combination thereof.

A fifty fifth embodiment may include the reactive distillation method of any of the forty second to fifty fourth embodiments, wherein the catalyst comprises $CuO/ZnO/Al_2O_3$, $CuO/Cr_2O_3/Al_2O_3$, $CuO/ZrO_2/Al_2O_3$, or any combination thereof.

A fifty sixth embodiment may include the reactive distillation method of any of the forty second to fifty fifth embodiments, wherein the catalyst comprises copper, and wherein the catalyst has a copper weight loading of between about 0.5% and about 80% of the catalyst.

A fifty seventh embodiment may include the reactive distillation method of any of the forty second to fifty sixth embodiments, wherein the catalyst comprises copper oxide and alumina disposed on a zirconium dioxide support.

A fifty eighth embodiment may include the reactive distillation method of any of the forty second to fifty seventh embodiments, wherein the catalyst comprises copper oxide and zirconium dioxide disposed on an alumina support.

A fifty ninth embodiment may include the reactive distillation method of any of the forty second to fifty eighth embodiments, wherein a selectivity of the conversion of ethanol to butanol and ethyl acetate is at least about 90% and a selectivity of the conversion of ethanol to butanol is at least about 20%.

A sixtieth embodiment may include the reactive distillation method of any of the forty second to fifty ninth embodiments, wherein the catalyst comprises sodium carbonate.

A sixty first embodiment may include the reactive distillation method of any of the forty second to sixtieth embodiments, wherein the catalyst is at least partially reduced in the presence of hydrogen.

A sixty second embodiment may include the reactive distillation method of any of the forty second to sixty first embodiments, wherein the catalyst comprises a multi-component catalyst.

A sixty third embodiment may include the reactive distillation method of the sixty second embodiment, wherein the multi-component catalyst comprises a first catalyst component and second catalyst component, wherein the first catalyst component comprises a dehydrogenation catalyst component, and wherein the second catalyst component is configured to convert at least a portion of the ethanol in the feed stream into the reaction product comprising butanol and water.

A sixty fourth embodiment may include the reactive distillation method of the sixty second embodiment, wherein the first catalyst component comprises less than about 30% by volume of the combined volume of the first catalyst component and the second catalyst component.

A sixty fifth embodiment may include the reactive distillation method of the sixty third or sixty fourth embodiment, wherein the first catalyst component comprises Cu, Pd, Pt, $Cr_2O_3$, $PtO_2$, $Cu_2Cr_2O_5$, any salt thereof, or any oxide thereof.

A sixty sixth embodiment may include the reactive distillation method of any of the sixty third to sixty fifth embodiments, wherein the second catalyst component comprises magnesium oxide, magnesium hydroxide, magnesium phosphate hydrate ($Mg_3(PO_4)_2 \cdot 8H_2O$), calcium oxide, calcium hydroxide, calcium fluoride, calcium silicate (wollastonite), calcium sulfate dihydrate (gypsum), lithium phosphate, aluminum phosphate, titanium dioxide, fluorapatite ($Ca_{10}(PO_4)_6F_2$), tetracalcium phosphate ($Ca_4(PO_4)_2O$), hydrotalcite, talc, kaolin, sepiolite, or any combination thereof.

A sixth seventh embodiment may include the reactive distillation method of any of the forty second to sixty sixth embodiments, further comprising: removing a side stream from the reactive distillation column, and contacting the side stream with a second catalyst, wherein the side stream reacts in the presence of the second catalyst to produce butanol.

A sixty eighth embodiment may include the reactive distillation method of the sixty seventh embodiment, further comprising: adjusting a flow rate of the side stream to achieve a desired bottoms stream composition.

A sixty ninth embodiment may include the reactive distillation method of the sixty eighth embodiment, wherein adjusting comprises increasing the flow rate of the side stream to increase the production of butanol relative to ethyl acetate.

A seventieth embodiment may include the reactive distillation method of the sixty eighth embodiment, wherein adjusting comprises decreasing the flow rate of the side stream to decrease the production of butanol relative to ethyl acetate.

A seventy first embodiment may include the reactive distillation method of any of the forty second to sixty sixth embodiments, further comprising: removing a side stream from the reactive distillation column, and contacting the side stream with a second catalyst, wherein the side stream reacts in the presence of the second catalyst to produce ethyl acetate.

A seventy second embodiment may include the reactive distillation method of the seventy first embodiment, further comprising: adjusting a flow rate of the side stream to achieve a desired bottoms stream composition.

A seventy third embodiment may include the reactive distillation method of the seventy second embodiment, wherein adjusting comprises increasing the flow rate of the side stream to decrease the production of butanol relative to ethyl acetate.

A seventy fourth embodiment may include the reactive distillation method of the seventy second embodiment, wherein adjusting comprises decreasing the flow rate of the side stream to increase the production of butanol relative to ethyl acetate.

A seventy fifth embodiment may include the reactive distillation method of the seventy second embodiment, wherein adjusting comprises cutting off the flow rate of the side stream to produce pure or substantially pure butanol.

A seventy sixth embodiment may include the reactive distillation method of any of the forty second to seventy fifth embodiment, wherein a liquid portion of the feed stream reacts in the presence of the catalyst to produce a reaction product comprising butanol and water.

In a seventy seventh embodiment, a reactive distillation system comprises: a feed stream comprising ethanol; a reactive distillation column comprising: a catalyst located generally centrally in the column, an ethanol feed in fluid communication with the reactive distillation column and configured to pass ethanol from the feed stream over the catalyst, an overhead product water and hydrogen removal passage, and a bottoms product butanol and ethyl acetate removal passage; a product separation system comprising an inlet configured to receive the bottoms product from the reactive distillation column, a butanol product removal passage, and an ethyl acetate product removal passage.

A seventy eighth embodiment may include the reactive distillation system of the seventy seventh embodiment, further comprising a bottoms ethanol recycle line coupling the ethanol removal passage from the product separation system and an inlet to the reactive distillation column.

A seventy ninth embodiment may include the reactive distillation system of any of the seventy seventh or seventy eighth embodiments, further comprising a separator and an overhead ethanol recycle line, wherein the overhead product water and hydrogen removal passage couples the reactive distillation column to the separator and the overhead ethanol recycle line couples the separator to an inlet to the reactive distillation column.

An eightieth embodiment may include the reactive distillation system of any of the seventy seventh to seventy ninth embodiments, further comprising a hydrogenation catalyst positioned to contact a liquid product following passage over the catalyst.

An eighty first embodiment may include the reactive distillation system of any of the seventy seventh to eightieth embodiments, wherein the product separation system further comprises at least one of a lights product removal passage or a heavies product removal passage.

An eighty second embodiment may include the reactive distillation system of the seventy seventh embodiment, wherein the reactive distillation column comprises a batch reactor configured to contact a liquid ethanol feed with the catalyst and remove water during the contacting of the liquid ethanol feed with the catalyst.

An eighty third embodiment may include the reactive distillation system of the seventy seventh embodiment, wherein the reactive distillation column comprises a continuous stirred-tank reactor (CSTR) configured to contact a liquid ethanol feed with the catalyst and remove water during the contacting of the liquid ethanol feed with the catalyst.

An eighty fourth embodiment may include the reactive distillation method of any of the seventy seventh to eighty third embodiments, further comprising introducing a second feed stream comprising hydrogen to the reactive distillation column.

In an eighty fifth embodiment, a reactive distillation method comprises introducing a feed stream to a reactive distillation column, wherein the feed stream comprises ethanol; contacting the feed stream with a catalyst in the reactive distillation column during a distillation, wherein the feed stream reacts in the presence of the catalyst to produce a reaction product comprising butanol, ethyl acetate, water, and hydrogen; separating a bottoms stream during the distillation from the reactive distillation column, wherein the bottoms stream comprises butanol and ethyl acetate; separating an overhead stream during the distillation from the reactive distillation column, wherein the overhead stream comprises water and ethanol; separating a recycle stream from the overhead stream, wherein the recycle stream comprises at least a portion of the ethanol from the overhead stream; and recycling the recycle stream to the reactive distillation column.

An eighty sixth embodiment may include the reactive distillation method of the eighty fifth embodiment, further comprising: separating at least one byproduct from the recycle stream after separation of the recycle stream from the overhead stream and prior to recycling the recycle stream to the reactive distillation column.

An eighty seventh embodiment may include the reactive distillation method of the eighty fifth or eighty sixth embodiment, further comprising: separating the bottoms stream into a product stream and the recycle stream; and separating the product stream into a byproduct stream and a butanol product stream.

An eighty eighth embodiment may include the reactive distillation method of any of the eighty fifth to eighty seventh embodiments, further comprising introducing a second feed stream comprising hydrogen to the reactive distillation column.

An eighty ninth embodiment may include the reactive distillation method of any of the eighty fifth to eighty eighth embodiments, wherein the catalyst comprises a multi-component catalyst.

A ninetieth embodiment may include the reactive distillation method of the eighty ninth embodiment, wherein the multi-component catalyst comprises a first catalyst component and second catalyst component, wherein the first catalyst component comprises a dehydrogenation catalyst component, and wherein the second catalyst component is configured to convert at least a portion of the ethanol in the feed stream into the reaction product comprising butanol and water.

A ninety first embodiment may include the reactive distillation method of the ninetieth embodiment, wherein the first catalyst component comprises less than about 30% by volume of the combined volume of the first catalyst component and the second catalyst component.

A ninety second embodiment may include the reactive distillation method of the ninetieth or ninety first embodiment, wherein the first catalyst component comprises Cu, Pd, Pt, $Cr_2O_3$, $PtO_2$, $Cu_2Cr_2O_5$, any salt thereof, or any oxide thereof.

A ninety third embodiment may include the reactive distillation method of any of the ninetieth to ninety second embodiments, wherein the second catalyst component comprises magnesium oxide, magnesium hydroxide, magnesium phosphate hydrate ($Mg_3(PO_4)_2 \cdot 8H_2O$), calcium oxide, calcium hydroxide, calcium fluoride, calcium silicate (wollastonite), calcium sulfate dihydrate (gypsum), lithium phosphate, aluminum phosphate, titanium dioxide, fluorapatite ($Ca_{10}(PO_4)_6F_2$), tetracalcium phosphate ($Ca_4(PO_4)_2O$), hydrotalcite, talc, kaolin, sepiolite, or any combination thereof.

In a ninety fourth embodiment, a reactive distillation method comprises: introducing a feed stream to a reactive distillation column, wherein the feed stream comprises one or more alpha hydrogen alcohols; contacting the feed stream with one or more catalysts in the reactive distillation column during a distillation, wherein the feed stream reacts in the presence of the one or more catalysts to produce a reaction product comprising one or more higher alcohols; and removing the higher alcohols during the distillation from the reactive distillation column as a bottoms stream.

A ninety fifth embodiment may include the method of the ninety fourth embodiment, wherein the one or more alpha hydrogen alcohols comprise one or more of ethanol, propanol, or butanol.

A ninety sixth embodiment may include the method of the ninety fourth embodiment, wherein the one or more alpha hydrogen alcohols comprise only ethanol.

A ninety seventh embodiment may include the method of any of the ninety fourth to ninety sixth embodiments, wherein the one or more higher alcohols comprise a $C_6$-$C_{13}$ alcohol.

A ninety eighth embodiment may include the method of any of the ninety fourth to ninety sixth embodiments, wherein the one or more higher alcohols comprise at least one alcohol selected from the group consisting of: 1-hexanol, 2-ethyl-1-butanol, 1-octanol, 2-ethyl-2-hexanol, heptanol, decanol, and dodecanols.

A ninety ninth embodiment may include the reactive distillation method of any of the ninety fourth to ninety eighth embodiments, wherein the catalyst comprises a Guerbet reaction catalyst, a solid base multicomponent oxide catalyst, a solid acid/base bifunctional catalyst, a zeolite with alkali counterions, a magnesium oxide catalyst, an oxide powder catalyst, or any combination thereof.

A one hundredth embodiment may include the reactive distillation method of any of the ninety fourth to ninety ninth embodiments, wherein the catalyst comprises a dual function catalyst.

A one hundred first embodiment may include the reactive distillation method of any of the ninety fourth to one hundredth embodiments, wherein the catalyst comprises a hydroxyapatite Guerbet reaction catalyst, a solid base Guerbet reaction catalyst, or a combination thereof.

A one hundred second embodiment may include the reactive distillation method of any of the ninety fourth to one hundred first embodiments, wherein the catalyst comprises $CuO/SiO_2$, $CuO/SiO_2$—$Al_2O_3$, $CuO/ZnO$, $CuO/ZrO_2$, $CuO/SiO_2$—$ZrO_2$ $CuO/Al_2O_3$, $CuO/MgO$, $CuO/MgO/SiO_2$, $CuO/MgO/Al_2O_3$, $CuO/ZnO/SiO_2$, $CuO/ZrO_2/SiO_2$, $CuO/MgO/SiO_2$, $CuO/CaO/SiO_2$, $CuO/SrO/SiO_2$, $CuO/BaO/SiO_2$, $CuO/ZrO_2/Al_2O_3/SiO_2$ and $CuO/Na_2O/SiO_2$, $CuO/ZnO/Al_2O_3$, $CuO/Cr_2O_3/Al_2O_3$, and $CuO/ZrO_2/Al_2O_3$, or any combination thereof.

A one hundred third embodiment may include the reactive distillation method of the one hundred second embodiment, wherein the catalyst has a copper weight loading of between about 0.5% and about 50% of the catalyst.

A one hundred fourth embodiment may include the reactive distillation method of any of the ninety fourth to one hundred third embodiment, wherein the catalyst comprises a catalyst component represented by the formula: $M/MgO/Al_2O_3$, wherein M represents palladium, rhodium, platinum, silver, gold, nickel, or copper, or oxides thereof.

A one hundred fifth embodiment may include the reactive distillation method of any of the ninety fourth to one hundred fourth embodiments, wherein the catalyst comprises a hydroxyapatite represented by the formula: $Ca_{10}(PO_4)_6(OH)_2$, wherein the ratio of calcium to phosphorus (Ca:P) is between about 1.5 and about 1.8.

A one hundred sixth embodiment may include the reactive distillation method of any of the ninety fourth to one hundred fifth embodiments, wherein the catalyst comprises an apatite structure satisfying the formula: $M_a(M'O_b)_cX_2$, wherein M represents calcium, strontium, magnesium, barium, lead, cadmium, iron, cobalt, nickel, zinc, or hydrogen, wherein M' represents phosphorus, vanadium, arsenic, carbon, or sulfur, wherein X represents a fluorine, chlorine, bromine, or a hydroxide, and wherein a is about 10, b is about 3, c is about 6, and the ratio of a to c is between about 1.5 and about 1.8.

A one hundred seventh embodiment may include the reactive distillation method of any of the ninety fourth to one hundred sixth embodiments, wherein the catalyst comprises a calcium phosphate, a calcium phosphate carbonate, a calcium pyrophosphate, a magnesium phosphate, a magnesium phosphate carbonate, a magnesium pyrophosphate or any combination thereof.

A one hundred eighth embodiment may include the reactive distillation method of any of the ninety fourth to one hundred seventh embodiments, wherein the catalyst comprises magnesium oxide, magnesium hydroxide, magnesium phosphate hydrate ($Mg_3(PO_4)_2 \cdot 8H_2O$), calcium oxide, calcium hydroxide, calcium fluoride, calcium silicate (wollastonite), calcium sulfate dihydrate (gypsum), lithium phosphate, aluminum phosphate, titanium dioxide, fluorapatite ($Ca_{10}(PO_4)_6F_2$), tetracalcium phosphate ($Ca_4(PO_4)_2O$), hydrotalcite, talc, kaolin, sepiolite, or any combination thereof.

A one hundred ninth embodiment may include the reactive distillation method of any of the ninety fourth to one hundred eighth embodiments, wherein the catalyst comprises at least one catalytic component selected from the group consisting of: copper, copper oxide, barium, barium oxide, ruthenium, ruthenium oxide, rhodium, rhodium oxide, platinum, platinum oxide, palladium, palladium oxide, rhenium, rhenium oxide, silver, silver oxide, cadmium, cadmium oxide, zinc, zinc oxide, zirconium, zirconium oxide, gold, gold oxide, thallium, thallium oxide, magnesium, magnesium oxide, manganese, manganese oxide, aluminum, aluminum oxide, chromium, chromium oxide, nickel, nickel oxide, iron, iron oxide, molybdenum, molybdenum oxide, sodium, sodium oxide, sodium carbonate, strontium, strontium oxide, tin, tin oxide, and any mixture thereof.

A one hundred tenth embodiment may include the reactive distillation method of any of the ninety fourth to one hundred ninth embodiments, wherein the catalyst comprises a multi-component catalyst.

A one hundred eleventh embodiment may include the reactive distillation method of the one hundred tenth embodiments, wherein the multi-component catalyst comprises a first catalyst component and a second catalyst component, wherein the first catalyst component is configured to convert at a portion of the ethanol in the feed stream to the ethyl acetate, and wherein the second catalyst component is configured to convert at least a portion of the ethanol in the feed stream into the butanol and water.

A one hundred twelfth embodiment may include the reactive distillation method of any of the ninety fourth to one hundred eleventh embodiments, further comprising: removing a side stream from the reactive distillation column; contacting the side stream with a side reactor catalyst, wherein the side stream reacts in the presence of the side reactor catalyst to produce a higher alcohol; and reintroducing the higher alcohol produced in the presence of the side reactor catalyst to the reactive distillation column.

A one hundred thirteenth embodiment may include the reactive distillation method of any of the ninety fourth to one hundred twelfth embodiments, further comprising: adjusting a pressure of the reactive distillation column to increase higher alcohol production.

A one hundred fourteenth embodiment may include the reactive distillation method of any of the ninety fourth to one hundred thirteenth embodiments, further comprising introducing a second feed stream comprising hydrogen to the reactive distillation column.

In a one hundred fifteenth embodiment, a reactive distillation method comprises: introducing a feed stream to a reactive distillation column, wherein the feed stream comprises ethanol; contacting the feed stream with one or more catalysts during a distillation, wherein the feed stream reacts in the presence of the one or more catalysts to produce a reaction product comprising a $C_6$-$C_{13}$ alcohol; and removing the $C_6$-$C_{13}$ alcohol during the distillation from the reactive distillation column as a bottoms stream.

A one hundred sixteenth embodiment may include the method of the one hundred fifteenth embodiment, wherein the one or more catalysts are disposed in the reactive distillation column.

A one hundred seventeenth embodiment may include the method of the one hundred fifteenth embodiment, wherein the one or more catalysts are disposed in a side reactor in fluid communication with the reactive distillation column.

A one hundred eighteenth embodiment may include the reactive distillation method of the one hundred seventeenth embodiment, further comprising: removing a side stream from the reactive distillation column; contacting the side stream with a side reactor catalyst in the side reactor, wherein the side stream reacts in the presence of the side reactor catalyst to produce the $C_6$-$C_{13}$ alcohol; and reintroducing the $C_6$-$C_{13}$ alcohol produced in the presence of the side reactor catalyst to the reactive distillation column.

A one hundred nineteenth embodiment may include the reactive distillation method of any of the one hundred fifteenth to the one hundred eighteenth embodiments, further comprising: removing the bottoms stream from the reactive distillation column, wherein the feed stream reacts in the presence of the one or more catalysts to produce a reaction product comprising the $C_6$-$C_{13}$ alcohol and butanol, and wherein the bottoms stream comprises the $C_6$-$C_{13}$ alcohol and butanol; separating at least a portion of the $C_6$-$C_{13}$ alcohol from the $C_2$-$C_5$ alcohols; and recycling the $C_2$-$C_5$ alcohols to the reactive distillation column.

A one hundred twentieth embodiment may include the reactive distillation method of any of the one hundred fifteenth to the one hundred nineteenth embodiments, further comprising: adjusting a pressure of the reactive distillation column to increase the $C_6$-$C_{13}$ alcohol production.

In a one hundred twenty first embodiment, a reactive distillation system comprises: a feed stream comprising an alpha hydrogen alcohol, where the alpha hydrogen alcohol is heavier than methanol; a reactive distillation column, wherein the reactive distillation column comprises: one or more catalysts disposed within the reactive distillation column, an alpha hydrogen alcohol feed configured to pass the feed stream comprising the alpha hydrogen alcohol over at least a portion of the one or more catalysts to produce a higher alcohol, wherein the one or more catalysts are configured to cause the alpha hydrogen alcohol to react in the presence of the one or more catalysts to produce the higher alcohol, and wherein the higher alcohol comprises an alcohol that is heavier than the alpha hydrogen alcohol; an overhead product hydrogen removal passage, and a bottoms product higher alcohol removal passage.

A one hundred twenty second embodiment may include the system of the one hundred twenty first embodiment, further comprising: a side reactor in fluid communication with the reactive distillation column, wherein the side reactor comprises a second catalyst; an inlet in fluid communication with the side reactor and the reactive distillation column, and configured to pass a fluid from the reactive distillation column over the second catalyst, and an outlet in fluid communication with the side reactor and the reactive distillation column, and configured to pass the fluid from an outlet of the side reactor to the reactive distillation column.

A one hundred twenty third embodiment may include the reactive distillation system of the one hundred twenty second embodiment, wherein the inlet is coupled to the reactive distillation column below the outlet.

A one hundred twenty fourth embodiment may include the reactive distillation system of the one hundred twenty third embodiment, wherein the fluid is a vapor.

A one hundred twenty fifth embodiment may include the reactive distillation system of the one hundred twenty second embodiment, wherein the inlet is coupled to the reactive distillation column above the outlet.

A one hundred twenty sixth embodiment may include the reactive distillation system of the one hundred twenty second embodiment, wherein the fluid is a liquid.

A one hundred twenty seventh embodiment may include the reactive distillation system of any of the one hundred twenty first to the one hundred twenty sixth embodiments, wherein the reactive distillation system further comprises: a hydrogen feed in fluid communication with the reactive distillation column and configured to pass hydrogen over at least a portion of the one or more catalysts.

A one hundred twenty eighth embodiment may include the reactive distillation system of any of the one hundred twenty first to the one hundred twenty seventh embodiments, wherein the alpha hydrogen alcohol feed comprises a $C_2$-$C_5$ alpha hydrogen alcohol.

A one hundred twenty ninth embodiment may include the reactive distillation system of any of the one hundred twenty first to the one hundred twenty eighth embodiments, wherein the higher alcohol comprises a $C_6$-$C_{13}$ alcohol.

In a one hundred thirtieth embodiment, a method of separating a mixed organic and aqueous phase stream, the method comprising: separating an inlet stream into an overhead stream and a bottoms stream in a separation unit, wherein the inlet stream comprises water, butanol, and an esters, wherein the overhead stream comprises the water and the esters, and wherein the bottoms stream comprises butanol; passing the overhead stream to a decanter; generating, in the decanter, an aqueous phase comprising substantially all of the water and an organic phase comprising the esters; removing the aqueous phase from the decanter as an aqueous stream; removing the organic phase from the decanter as an organics stream; separating the organics stream into a product stream and a recycle stream, wherein the product stream comprises the esters, and wherein the recycle stream comprises the water.

A one hundred thirty first embodiment may include the method of the one hundred thirtieth embodiment, wherein the esters comprises ethyl butyrate.

A one hundred thirty second embodiment may include the method of the one hundred thirtieth or the one hundred thirty first embodiment, wherein the bottoms stream comprises butanol having a purity of at least about 90% butanol by weight.

A one hundred thirty third embodiment may include the method of any of the one hundred thirtieth to the one hundred thirty second embodiments, wherein the separation unit comprises a distillation column.

A one hundred thirty fourth embodiment may include the method of any of the one hundred thirtieth to the one hundred thirty third embodiments, further comprising: recycling the recycle stream into the inlet stream.

In a one hundred thirty fifth embodiment, a method of separating a mixed organic and aqueous phase stream, the method comprises: separating an inlet stream into an overhead stream and a bottoms stream in a separation unit, wherein the inlet stream comprises water, a plurality of higher alcohols, and an esters, wherein the overhead stream comprises the water the esters, and a first portion of the plurality of higher alcohols, and wherein the bottoms stream comprises a second portion of the plurality of higher alcohols; separating the bottoms stream into at least one product stream comprising a first higher alcohol of the first portion of the plurality of higher alcohols; passing the overhead stream to a decanter; generating, in the decanter, an aqueous phase comprising substantially all of the water and an organic phase comprising the esters and the second portion of the plurality of higher alcohols; removing the aqueous phase from the decanter as an aqueous stream; removing the organic phase from the decanter as an organics stream; separating the organics stream into a first stream comprising the esters and a second stream comprising the second portion of the plurality of higher alcohols.

A one hundred thirty sixth embodiment may include the method of the one hundred thirty fifth embodiment, wherein separating the bottoms stream into at least one product stream comprises: separating the bottoms stream into a first product stream comprising butanol and a second product stream comprising the remainder of the first portion of the plurality of higher alcohols.

A one hundred thirty seventh embodiment may include the method of the one hundred thirty fifth embodiment, wherein separating the bottoms stream into at least one product stream further comprises: separating the remainder of the first portion of the plurality of higher alcohols into a third product stream comprising hexanol.

A one hundred thirty eighth embodiment may include the method of the one hundred thirty fifth embodiment, wherein separating the organics stream into a first stream comprising the esters and a second stream comprising the second portion of the plurality of higher alcohols comprises: separating the organics stream into a second overhead stream comprising the esters and water and a second bottoms stream comprising the second portion of the plurality of higher alcohols.

A one hundred thirty ninth embodiment may include the method of the one hundred thirty eighth embodiment, wherein separating the organics stream into a first stream comprising the esters and a second stream comprising the second portion of the plurality of higher alcohols further comprises: passing the second overhead stream to a second decanter; generating, in the second decanter, a second aqueous phase comprising substantially all of the water in the organics stream and a second organic phase comprising the esters; removing the second aqueous phase from the second decanter as a second aqueous stream; removing the second organic phase from the second decanter as a second organics stream; separating the second organics stream into an esters product stream comprising the esters.

A one hundred fortieth embodiment may include the method of the one hundred thirty eighth embodiment, wherein separating the organics stream into a first stream comprising the esters and a second stream comprising the second portion of the plurality of higher alcohols further comprises: separating the second bottoms stream into a third overhead stream and a third bottoms stream, wherein the third overhead stream comprises at least one higher alcohol of the second portion of the plurality of higher alcohols.

A one hundred forty first embodiment may include the method of the one hundred fortieth embodiment, wherein separating the second bottoms stream into a third overhead stream and a third bottoms stream occurs at a pressure greater than about 3 atmospheres.

A one hundred forty second embodiment may include the method of any of the one hundred thirty fifth to the one hundred forty first embodiments, wherein the esters comprises one or more of ethyl acetate or ethyl butyrate.

In a one hundred forty third embodiment, a method of separating an alcohol from ethyl acetate, the method comprises: adding water to an inlet stream to form a combined stream, wherein the inlet stream comprises an alcohol and ethyl acetate; distilling the combined stream to produce an overhead stream and a bottoms stream, wherein the overhead stream comprises a water and the ethyl acetate, and wherein the bottoms stream comprises a majority of the alcohol; condensing the overhead stream; and decanting an aqueous phase stream from an organic phase stream, wherein the aqueous phase stream comprises a majority of the water in the overhead stream, and wherein the organic phase stream comprises a majority of the ethyl acetate in the overhead stream.

In the preceding discussion and in the claims, the terms "including" and "comprising" are used in an open-ended fashion, and thus should be interpreted to mean "including, but not limited to . . . ". At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of.

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the embodiments of the present disclosure. The discussion of a reference herein is not an admission that it is prior art to the present disclosure, especially any reference that may have a publication date after the priority date of this application. The disclosures of all patents, patent applications, and publications cited herein are hereby incorporated by reference, to the extent that they provide exemplary, procedural, or other details supplementary to those set forth herein.

What is claimed is:

1. A reactive distillation method comprising:
   introducing a feed stream to a reactive distillation column, wherein the feed stream comprises one or more alpha hydrogen alcohols;
   contacting the feed stream with one or more catalysts in the reactive distillation column during a distillation, wherein the feed stream reacts in contact with the one or more catalysts to produce a reaction product comprising one or more higher alcohols, wherein the one or more higher alcohols are alcohols having a higher molecular weight than the corresponding one or more alpha hydrogen alcohols in the feed stream, and wherein the one or more higher alcohols comprise a $C_4$-$C_{13}$ alcohol; and
   removing the one or more higher alcohols during the distillation from the reactive distillation column as a bottoms stream.

2. The reactive distillation method of claim 1, wherein the feed stream further comprises water.

3. The method of claim 1, wherein the one or more alpha hydrogen alcohols comprise one or more of ethanol, propanol, or butanol.

4. The method of claim 1, wherein the one or more alpha hydrogen alcohols comprise only ethanol.

5. The method of claim 1, wherein the one or more higher alcohols comprise at least one alcohol selected from the group consisting of: 1-butanol, 1-hexanol, 2-ethyl-1-butanol, 1-octanol, 2-ethyl-2-hexanol, heptanol, decanol, and dodecanols.

6. The reactive distillation method of claim 1, wherein the one or more catalysts comprise a Guerbet reaction catalyst, a solid base multicomponent oxide catalyst, a solid acid/base bifunctional catalyst, a zeolite with alkali counterions, a magnesium oxide catalyst, an oxide powder catalyst, or any combination thereof.

7. The reactive distillation method of claim 1, wherein the one or more catalysts comprise a dual function catalyst.

8. The reactive distillation method of claim 1, wherein the one or more catalysts comprise a hydroxyapatite Guerbet reaction catalyst, a solid base Guerbet reaction catalyst, or a combination thereof.

9. The reactive distillation method of claim 1, wherein the one or more catalysts comprise $CuO/SiO_2$, $CuO/SiO_2$—$Al_2O_3$, $CuO/ZnO$, $CuO/ZrO_2$, $CuO/SiO_2$—$ZrO_2$ $CuO/Al_2O_3$, $CuO/MgO$, $CuO/MgO/SiO_2$, $CuO/MgO/Al_2O_3$, $CuO/ZnO/SiO_2$, $CuO/ZrO_2/SiO_2$, $CuO/MgO/SiO_2$, $CuO/CaO/SiO_2$, $CuO/SrO/SiO_2$, $CuO/BaO/SiO_2$, $CuO/ZrO2/Al_2O_3/SiO_2$ and $CuO/Na_2O/SiO_2$, $CuO/MgO/Al_2O_3/SiO_2$ $CuO/CeO2/MgO/Al_2O_3$, $CuO/ZnO/Al_2O_3$, $CuO/Cr_2O_3/Al_2O_3$, and $CuO/ZrO_2/Al_2O_3$, or any combination thereof.

10. The reactive distillation method of claim 1, wherein the one or more catalysts comprise copper, and wherein the catalyst has a copper weight loading of between about 0.5% and about 80% of the catalyst.

11. The reactive distillation method of claim 1, wherein the one or more catalysts comprise a catalyst component represented by the formula:

$M/MgO/Al_2O_3$, wherein M represents palladium, rhodium, platinum, silver, gold, nickel, or copper, or oxides thereof.

12. The reactive distillation method of claim 1, wherein the one or more catalysts comprise a hydroxyapatite represented by the formula:

$Ca_{10}(PO_4)_6(OH)_2$ wherein the ratio of calcium to phosphorus (Ca:P) is between about 1.5 and about 1.8.

13. The reactive distillation method of claim 1, wherein the one or more catalysts comprise an apatite structure satisfying the formula:

$M_a(M'O_b)_cX_2$, wherein M represents calcium, strontium, magnesium, barium, lead, cadmium, iron, cobalt, nickel, zinc, or hydrogen, wherein M' represents phosphorus, vanadium, arsenic, carbon, or sulfur, wherein X represents a fluorine, chlorine, bromine, or a hydroxide, and
wherein a is about 10, b is about 3, c is about 6, and the ratio of a to c is between about 1.5 and about 1.8.

14. The reactive distillation method of claim 1, wherein the one or more catalysts comprise a calcium phosphate, a calcium phosphate carbonate, a calcium pyrophosphate, a magnesium phosphate, a magnesium phosphate carbonate, a magnesium pyrophosphate, magnesium oxide, magnesium hydroxide, magnesium phosphate hydrate ($Mg_3(PO_4)_2.8H_2O$), calcium oxide, calcium hydroxide, calcium fluoride, calcium silicate (wollastonite), calcium sulfate dihydrate (gypsum), lithium phosphate, aluminum phosphate, titanium dioxide, fluorapatite ($Ca_{10}(PO_4)_6F_2$), tetracalcium phosphate ($Ca_4(PO_4)_2O$), hydrotalcite, talc, kaolin, sepiolite, or any combination thereof.

15. The reactive distillation method of claim 1, wherein the one or more catalysts comprise at least one catalytic component selected from the group consisting of: copper, copper oxide, barium, barium oxide, ruthenium, ruthenium oxide, rhodium, rhodium oxide, platinum, platinum oxide, palladium, palladium oxide, rhenium, rhenium oxide, silver, silver oxide, cadmium, cadmium oxide, zinc, zinc oxide, zirconium, zirconium oxide, gold, gold oxide, thallium, thallium oxide, magnesium, magnesium oxide, manganese, manganese oxide, aluminum, aluminum oxide, chromium, chromium oxide, nickel, nickel oxide, iron, iron oxide, molybdenum, molybdenum oxide, sodium, sodium oxide, sodium carbonate, strontium, strontium oxide, tin, tin oxide, and any mixture thereof.

16. The reactive distillation method of claim 1, wherein the one or more catalysts comprise a multi-component catalyst, wherein the multi-component catalyst comprises a first catalyst component and second catalyst component, wherein the first catalyst component comprises a dehydrogenation catalyst component, and wherein the second catalyst component is configured to convert at least a portion of the one or more alpha hydrogen alcohols in the feed stream into the reaction product comprising the one or more higher alcohols and water.

17. The reactive distillation method of claim 1, wherein the one or more catalysts comprise a support, wherein the support comprises at least one support material selected from the group consisting of: carbon, silica, silica-alumina, alumina, zirconia, titania, ceria, vanadia, nitride, boron nitride, heteropolyacids, hydroxyapatite, zinc oxide, chromia, a zeolite, a carbon nanotube, carbon fullerene, and any combination thereof.

18. The reactive distillation method of claim 1, further comprising:
removing a side stream from the reactive distillation column;
contacting the side stream with a side reactor catalyst, wherein the side stream reacts in the presence of the side reactor catalyst to produce at least one of the one or more higher alcohols; and
reintroducing the at least one of the one or more higher alcohols produced in the presence of the side reactor catalyst to the reactive distillation column.

19. The reactive distillation method of claim 18, wherein the side stream comprises a vapor, and wherein contacting the side stream with the side reactor catalyst comprises contacting the vapor with the side reactor catalyst.

20. The reactive distillation method of claim 18, wherein the side stream comprises a liquid, and wherein contacting the side stream with the side reactor catalyst comprises contacting the liquid with the side reactor catalyst.

21. The reactive distillation method of claim 18, wherein the feed stream further reacts in contact with the one or more catalysts to produce a reaction product comprising ethyl acetate, wherein the method further comprising:
adjusting a flow rate of the side stream; and
increasing a production of the one or more higher alcohols relative to a production of the ethyl acetate in the bottoms stream.

22. The reactive distillation method of claim 1, further comprising:
removing a plurality of side streams from the reactive distillation column;
introducing each of the plurality of side streams into a corresponding plurality of side reactors, wherein each of the plurality of side reactors comprise at least one side reactor catalyst;
contacting each of the plurality of side streams with the at least one side reactor catalyst in the corresponding plurality of side reactors, wherein each of the plurality of side streams reacts in the presence of the one or more side reactor catalyst to produce a higher alcohol; and
reintroducing the higher alcohol produced in the presence of the side reactor catalyst from each of the plurality of side reactors to the reactive distillation column.

23. The reactive distillation method of claim 1, further comprising:
increasing a pressure of the reactive distillation column; and
increasing a molecular weight of the one or more higher alcohols in the bottoms product.

24. The reactive distillation method of claim 1, further comprising introducing a second feed stream comprising hydrogen to the reactive distillation column.

25. The reactive distillation method of claim 1, further comprising:
removing the bottoms stream from the reactive distillation column, wherein the one or more higher alcohols comprise one or more $C_6$-$C_{13}$ alcohols, and butanol;
separating at least a portion of the one or more $C_6$-$C_{13}$ alcohols from one or more $C_2$-$C_5$ alcohols; and
recycling the one or more $C_2$-$C_5$ alcohols to the reactive distillation column.

26. The reactive distillation method of claim 1, wherein the reactive distillation column comprises a continuous stirred-tank reactor (CSTR).

27. The reactive distillation method of claim 1, further comprising:
separating an inlet stream into an overhead stream and a bottoms stream in a separation unit, wherein the bottoms stream comprises water, the one or more higher alcohols, and an esters, wherein the overhead stream comprises the water and the ester, wherein the one or more higher alcohols comprise butanol, and wherein the second bottoms stream comprises butanol;
passing the overhead stream to a decanter;
generating, in the decanter, an aqueous phase comprising substantially all of the water and an organic phase comprising the esters;
removing the aqueous phase from the decanter as an aqueous stream;
removing the organic phase from the decanter as an organics stream;
separating the organics stream into a product stream and a recycle stream, wherein the product stream comprises the esters, and wherein the recycle stream comprises the water.

28. The reactive distillation method of claim 27, wherein the esters comprises one or more of ethyl butyrate, ethyl acetate and butyl acetate.

29. The reactive distillation method of claim 27, wherein the separation unit comprises a plurality of distillation columns.

30. The reactive distillation method of claim 1, further comprising:
separating the bottoms stream into an overhead strewn and a second bottoms stream in a separation unit, wherein the bottoms stream comprises water, of the one or more higher alcohols, and one or more esters, wherein the overhead stream comprises the water, the one or more esters, and a first portion of the one or more higher alcohols, and wherein the second bottoms stream comprises a second portion of the one or more higher alcohols;
separating the second bottoms stream into at least one product stream comprising a first higher alcohol of the first portion of the one or more higher alcohols;
passing the overhead stream to a decanter;
generating, in the decanter, an aqueous phase comprising substantially all of the water and an organic phase comprising the one or more esters and the second portion of the one of more higher alcohols;
removing the aqueous phase from the decanter as an aqueous stream;
removing the organic phase from the decanter as an organics stream; and
separating the organics stream into a first stream comprising the one or more esters and a second stream comprising the second portion of the one or more higher alcohols.

31. The reactive distillation method of claim 30, wherein separating the second bottoms stream into at least one product stream comprises:
separating the second bottoms stream into a first product stream comprising butanol and a second product stream comprising the remainder of the first portion of the one or more higher alcohols.

32. The reactive distillation method of claim 30, wherein separating the bottoms stream into at least one product stream further comprises:
separating the remainder of the first portion of the one or more higher alcohols into a third product stream comprising hexanol.

33. The reactive distillation method of claim 30, wherein separating the organics stream into a first stream comprising the one or more esters and a second stream comprising the second portion of the one or more higher alcohols comprises:

separating the organics stream into a second overhead stream comprising the one or more esters and water and a third bottoms stream comprising the second portion of the one or more higher alcohols.

34. The reactive distillation method of claim 33, wherein separating the organics stream into a first stream comprising the one or more esters and a second stream comprising the second portion of the one or more higher alcohols further comprises:

passing the second overhead stream to a second decanter;

generating, in the second decanter, a second aqueous phase comprising substantially all of the water in the organics stream and a second organic phase comprising the esters;

removing the second aqueous phase from the second decanter as a second aqueous stream;

removing the second organic phase from the second decanter as a second organics stream;

separating the second organics stream into an esters product stream comprising the one or more esters.

35. The reactive distillation method of claim 33, wherein separating the organics stream into a first stream comprising the one or more esters and a second stream comprising the second portion of the one or more higher alcohols further comprises;

separating the third bottoms stream into a third overhead stream and a fourth bottoms stream, wherein the third overhead stream comprises at least one higher alcohol of the second portion of the one or more higher alcohols.

36. The reactive distillation method of claim 35, wherein separating the third bottoms stream into a third overhead stream and a fourth bottoms stream occurs at a pressure greater than about 3 atmospheres.

37. The reactive distillation method of claim 30, wherein separating the organics stream into the first stream comprising the one or more esters and the second stream comprising the second portion of the one or more higher alcohols occurs in a distillation system, wherein the distillation system comprises a distillation column and at least one rectifier or stripper in fluid communication with the distillation column.

38. A reactive distillation method of claim 1, wherein the bottoms stream comprises water, the one or more higher alcohols, and one or more butyl esters comprising butyl acetate, wherein the method further comprises:

distilling the bottoms stream to produce an overhead stream and a second bottoms stream, wherein the overhead stream comprises at least a portion of the water and the butyl acetate, and wherein the bottoms stream comprises a majority of the one or more higher alcohols;

condensing the overhead stream; and decanting an aqueous phase stream from an organic phase stream, wherein the aqueous phase stream comprises a majority of the water in the overhead stream, and wherein the organic phase stream comprises a majority of the butyl acetate in the overhead stream.

39. The reactive distillation method of claim 18, wherein the side reactor catalyst is disposed within one or more side reactors, and wherein the amount of side reactor catalyst in the one or more side reactors is greater than an amount of the one or more catalysts in the reactive distillation column.

40. The reactive distillation method of claim 1, further comprising:

removing the bottoms stream from the reactive distillation column, wherein the one or more higher alcohols comprise one or more $C_6$-$C_{13}$ alcohols;

separating at least a portion of the one or more $C_6$-$C_{13}$ alcohols from a remaining portion of the bottoms stream; and recycling at least a portion of the remaining portion of the bottoms stream to the reactive distillation column.

41. The reactive distillation method of claim 1, wherein the one or more alpha hydrogen alcohols comprise ethanol, and wherein the one or more higher alcohols comprise butanol.

* * * * *

UNITED STATES PATENT AND TRADEMARK OFFICE
CERTIFICATE OF CORRECTION

PATENT NO. : 9,018,427 B2
APPLICATION NO. : 14/183273
DATED : April 28, 2015
INVENTOR(S) : Sagar B. Gadewar et al.

It is certified that error appears in the above-identified patent and that said Letters Patent is hereby corrected as shown below:

In the claims:

Claim 3, Column 75, Line 30, replace "The method of claim 1" with --The reactive distillation method of claim 1--.
Claim 4, Column 75, Line 33, replace "The method of claim 1" with --The reactive distillation method of claim 1--.
Claim 5, Column 75, Line 35, replace "The method of claim 1" with --The reactive distillation method of claim 1--.
Claim 27, Column 78, Line 1, replace "an inlet stream" with --the bottoms stream--.
Claim 27, Column 78, Lines 1-2, replace "and a bottoms stream" with --and a second bottoms stream--.
Claim 27, Column 78, Line 4, replace "and an esters," with --and an ester,--.
Claim 30, Column 78, Line 28, replace "an overhead strewn" with --an overhead stream--.

Signed and Sealed this
Twenty-ninth Day of September, 2015

Michelle K. Lee
*Director of the United States Patent and Trademark Office*